United States Patent [19]
Guthridge et al.

[11] Patent Number: 5,976,853
[45] Date of Patent: Nov. 2, 1999

[54] GROWTH FACTOR INDUCIBLE SERINE/THREONINE PHOSPHATASE FIN13

[75] Inventors: Mark A. Guthridge; Claudio Basilico, both of New York, N.Y.

[73] Assignee: New York University Medical Center, New York, N.Y.

[21] Appl. No.: 08/822,701

[22] Filed: Mar. 21, 1997

Related U.S. Application Data

[60] Provisional application No. 60/013,792, Mar. 21, 1996.

[51] Int. Cl.$^6$ .............................. C12N 9/16; C07H 21/04
[52] U.S. Cl. ....................... 435/196; 435/195; 435/325; 435/252.3; 435/252.33; 435/235.1; 435/320.1; 536/23.1; 536/23.2; 536/23.5
[58] Field of Search ................................. 435/196, 252.3, 435/252.33, 325, 320.1, 195, 235.1; 536/23.1, 23.2, 23.5

[56] References Cited

PUBLICATIONS

Hunter, 1995, *Cell,* 80:225–236.
Wilson et al., 1994, *Nature* 368:32–8.
Scherens et al., 1993, *Yeast* 9:1355–71.
Terasawa et al. 1993 *Arch. Biochem. Biophys.* 307:342–9.
Basilico and Moscatelli, 1992, *Adv. Cancer Res.,* 59:115–165.
Lanahan et al., 1992, *Mol. Cell. Biol.,* 12:3919–3929.
Mann et al., 1992, *Biochem. Biophys. Acta* 1130:100–4.
Wenk et al., 1992, *FEBS Lett.* 297:135–8.
Gomez and Cohen, 1991, *Nature,* 353:170–173.
Ito et al., 1990, *Oncogene,* 5:1755–1760.
Lim et al., 1989, *Mol. Cell. Biol.,* 9:1790–1793.
Ryseck, R.P., et al., 1989, *Exp. Cell Res.,* 180:266–275.
Chavrier et al., 1988, *EMBO J.,* 7:29–35.
Lemaire et al., 1988, *Proc. Natl. Acad. Sci. U.S.A.,* 85:4691–4695.
Stein, R., et al., 1988, *Deve. Biol.,* 127:316–325.
Delli Bovi and Basilico, 1987, *Proc. Natl. Acad. Sci. USA* 84:5660.
Carter, TC, 1951, *J. Genet.* 50:277–99.
Hillier et al. (1995) EMBL Entry: Accession # R53331.
Wang et al. (1995) *J. Biol. Chem.* 270:25607–12.
Qin et al. (1996) *FASEB J.* 10:A1251.
Huang et al. (1996) EMBL Entry: Accession # U81159.
Guthridge et al. (1996) *Oncogene* 12:1267–78.
Klumpp et al. (1994) *J. Biol. Chem.* 269:32774–80.
Wenk et al. (1995) *Eur. J. Cell Biol.* 68:377–86.
Kitamura et al. (1992) *Jap. J. Can. Res.* 83:66–71.
Mumby et al. (1993) *Phys. Rev.* 73:673–99.
Peruski, Jr. et al. (1993) *Adv. Prot. Phosphatases.*

*Primary Examiner*—Robert A. Wax
*Assistant Examiner*—Nashaat T. Nashed
*Attorney, Agent, or Firm*—Klauber & Jackson

[57] ABSTRACT

A novel serine/threonine phosphatase, FIN13, which includes a collagen-homology domain, an acidic box domain, a catalytic domain, and a putative nuclear translocation sequence. The present invention further relates to the modulation of cellular proliferation, by regulating the activity of the novel serine/threonine phosphatase. Thus, the invention provides the phosphatase, nucleic acids encoding the phosphatase, oligonucleotides specific for such nucleic acids, antibodies to the phosphatase, and methods for increasing (or decreasing) the activity of the phosphatase to inhibit (or enhance) cellular proliferation and, thus, tissue growth. Various diagnostic and therapeutic aspects of the invention particularly relate to detection and treatment of hyperproliferative disorders, neoplasms, and tumors. In specific examples, FIN13 is expressed in proliferating cells, notably gern cells of the testes. Increased levels of expression of FIN13 in transfected cells results in a decrease in the cell growth rate.

16 Claims, 14 Drawing Sheets

FIG. 1A

```
GGCACGAGGAAGGCCTACAAGGCAAGCTTCAGAAGGCTTTACAAGATGCCTTCTTG      60
GCTATTGATGCCAAGCTGACCAGAGAGAAGTCATTAAGGAACTGGCCCAGATTGCAGGG  120
AGACCCACTGAAGATGAGGATGATAAAGACAAAGTAGCCAGATGAGGATGATGTGACAAT 180
GAGGAGGCTGCATTGTTGCATGAAGAGCTACCATGACTATTGAAGAGCTGCTGACGCGA  240
                M  T  I  E  E  L  L  T  R                      9

TATGGGCAGAACTGTCAGAAGTCTCCCCACACCAAATCTGGAATTGGGACAGGCGAT    300
 Y  G  Q  N  C  Q  K  V  P  P  H  T  K  S  G  I  G  T  G  D    29

GAACCAGGGCCCCAGGGCCTCAATGGGGAGGCTGGACCTGAGGACCCATCTAGGGAAACT 360
 E  P  G  P  Q  G  L  N  G  E  A  G  P  E  D  P  S  R  E  T    49

CCTTCCCAGGAAAATGCCCCACAAAGGCCACACAGCCTTTCCTCCAACTCGGAA       420
 P  S  Q  E  N  G  P  T  A  K  G  H  T  G  F  S  S  N  S  E    69

CATGGGACTGAGGCCAGGCCAAATTAGTGAGCCCGTACTGCTACCGGTGAGGCTGACCT  480
 H  G  T  E  A  G  Q  I  S  E  P  G  T  A  T  G  E  A  G  P    89

TCCTGCTCTTCAGCCTCTGACAAGCTGCCTCGAGTTGCTAAGTCCAAGTTCTTTGAGAC  540
 S  C  S  S  A  S  D  K  L  P  R  V  A  K  S  K  F  F  E  D    109

AGTGAAGATGAATCAGATGAGGTGGAAGAGGATGACAGTGAGGAATGACAGTGAGTGAG  600
 S  E  D  E  S  D  E  V  E  E  E  D  D  S  E  E  C  S  E      129

GACGAGGACGGCTACAGCAGTGATGATGAAGAGATGATGGTCCCTGGAATGGAAGGCAAGAAGAG 660
 D  E  D  G  Y  S  S  E  E  A  E  N  E  E  D  E  D  D  T  E    149

GAGGCTGAAGAGGATGATGATGAAGAAATGATGGTCCCTGGAATGGAAGGCAAAGAAGAG 720
 E  A  E  E  D  D  D  E  E  M  M  V  P  G  M  E  G  K  E  E    169

CCTGGTTCTGACAGTGGCACAACAGCGGTGGTGGCTCTGATCAGAGGGAAGCAGTTGATT  780
 P  G  S  D  S  G  T  T  A  V  V  A  L  I  R  G  K  Q  L  I    189

GTGGCCAATGCAGGAGACTCTCGCTGTGTGTCCGAGGCTGGCAAAGCTTTAGATATG     840
 V  A  N  A  G  D  S  R  C  V  V  S  E  A  G  K  A  L  D  M    209

TCCTATGACCACAAACCAGGAGGATGAAGTGGAGCTGGCACGCATCAAGAATGCTGTGGC  900
 S  Y  D  H  K  P  E  D  E  V  E  L  A  R  I  K  N  A  G  G    229
```

FIG. 1B

```
AAGGTCACCATGGATGACGAGTCAATGGAGGCCTCAACCTCTCCAGGCCATTGGAGAC        960
K  V  T  M  D  D  E  S  M  E  A  S  T  L  S  R  A  I  G  D        249

CACTTCTACAAGAGAAACAAAACTGCACCCCAGAACAGAGATGATTCTGCCCTTCCT        1020
H  F  Y  K  R  N  K  N  L  P  P  Q  E  Q  M  I  S  A  L  P        269

GACATCAAGGTGCTGACTCTCACTGATGACCATGAATTCATGGTCATTGCTGTGACGGC      1080
D  I  K  V  L  T  L  T  D  D  H  E  F  M  V  I  A  C  D  G        289

ATCTGGAATGTGATGAGCAGCCAGGAGGTTGTAGACTTTATTCAATCAAAGATCAGTCAA     1140
I  W  N  V  M  S  S  Q  E  V  V  D  F  I  Q  S  K  I  S  Q        309

CGTGATGAAAACGGGGAGCTTCGGTTATGTCATTGTGGAAGAGCTGCTGGATCAG          1200
R  D  E  N  G  E  L  R  L  L  S  S  I  V  E  E  L  L  D  Q        329

TGCCTGGCGCCAGACACTTCTGGGATGTACAGGGTGACAACATGACTGCATCATC          1260
C  L  A  P  D  T  S  G  D  T  G  C  D  N  M  T  C  I  I          349

ATTTGCTTCAAGCCCCGAAACACAGTAGAGCTTCAGGCAGAGAGTGGCAAGAGAAACTG     1320
I  C  F  K  P  R  N  T  V  E  L  Q  A  E  S  G  K  R  K  L        369

GAGGAGGCACTGTCCACGGAGGGGCTGAAGACACCGGCAACAGTGACAAAAAGAAGGCC     1380
E  E  A  L  S  T  E  G  A  E  D  T  G  N  S  D  K  K  K  A        389

AAGAGGGACTAGTGGTCAACCGACCCTGCCCATGTGACTGTTTCTGAGCCCTTGGAC        1440
K  R  D                                                           392

CCGAGACTGAGTTTGTCCTTGTCCTTAGCCTTAGCAGTGGGTATGAGGTGTGCAGGGG       1500
GCTGGGTGGCTTTCCTCAGCCCATTACAAAGAGAGGCCCCCACCCGCCCGCCGGGCAGC     1560
CTGGGAGGCTCGCTCGTCTGTCTCTCCTTAAGCCTCCTTACTCTCCTTGGGCTCATCGACTATCGG      1620
TTCTGTGCCTGCTGTGTGTCTGTGTGTTGGAGGGAAGGACTGGCGGCTCTGTGACCCCTAGCCTTG     1680
TGAACACTTTATTTAAGGACATTCTTTTTTATTGGCGGCTCTGTGACCCCTAGCCGCTTG          1740
CACCCGCTCTCGTGTACACTTTCAAGCAACACTTTTTCAGACTAAAGGCCAAACAAA             1800
GCTAAAAAAAAAAAAAAAAAAAAAA                                             1824
```

FIN13 cDNA sequence and putative protein translation.

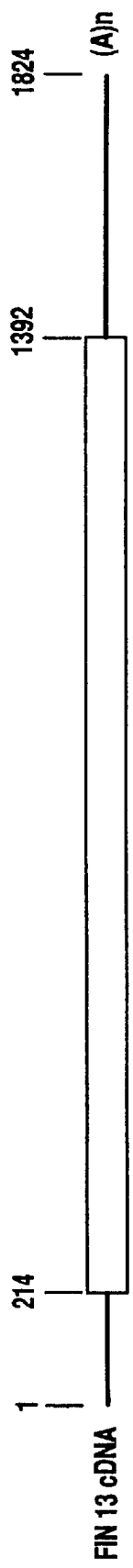
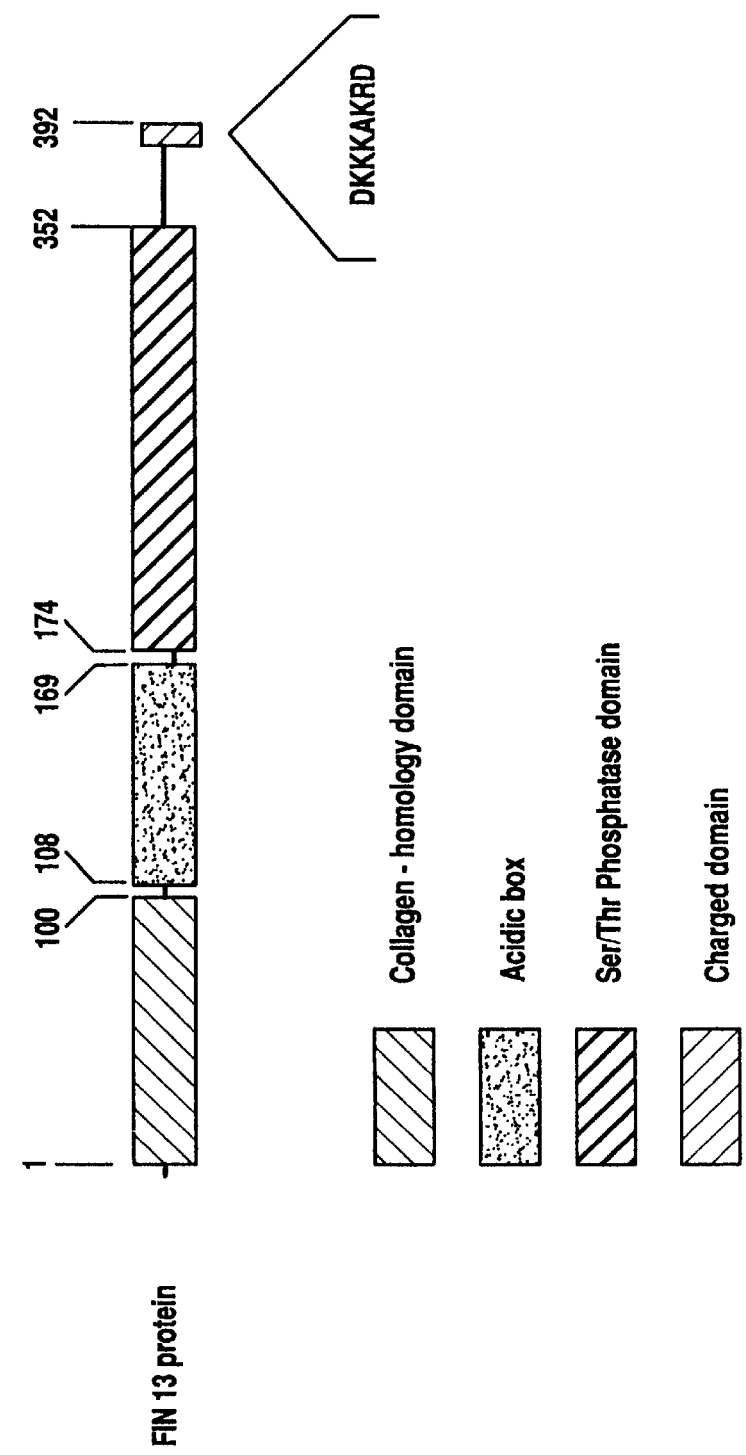

FIG.3A

```
              1                                                                    50
Mouse         ..........  ..........  ..........  ..........  ........MG  AFLDKPKTEK
Rat           ..........  ..........  ..........  ..........  ........MG  AFLDKPKMEK
Yeast         ..........  ..........  ..........  ..........  .....MSNHS  EILERPET..
Leishmania    ..........  ..........  ..........  ..........  ........MG  IPLPKPVMTQ
FIN13         MTIEELLTRY  GQNCQKVPPH  TKSGIGTGDE  ..........  PGPQGLNGEA  GPEDPSRETP 51                                                                   100
Mouse         HNAHGAGNGL  RYGLSSMQG.  ..........  .WRVEMEDAH  TAVVGIPHGL  DNWSFFAVYD
Rat           HNAQGQGNGL  RYGLSSMQG.  ..........  .WRVEMEDAH  TAVIGLPSGL  ETWSFFAVYD
Yeast         ...PYDITY   RVGVAENKNS  KFRRTMEDVH  TYVKNFASRL  D.WGYFAVFD
Leishmania    LQERYGNAIF  RCGSNCVNG.  .YRETMEDAH  ....LTYLT   DSWGFFGVFD
FIN13         SQENGPTAKG  HTGFSSNSE.  ...HGTEAGQ  ISEPGTATGE  AGPSCSSASD 101                                                                  150
Mouse         GHAGSRVANY  CSTHLLEHIT  TNEDFRAADK  SGSALEP...  .SVESVKTG
Rat           GHAGSQVAKY  CCEHLLDHIT  NNQDFK....  .GSAGAP...  .SVENVKNGI
Yeast         GHAGIQASKW  CGKHLHTIIE  QNILADETRD  VRDVLND...  .SFLAIDEEI
Leishmania    GHVNDQCSQY  LERAWRSAIE  KE........  ..........  .SIPMTDERM
FIN13         KLPRVAKSKF  FEDSEDESDE  VEEEEDDSEE  CSEDEDGYSS  EEAENEEDED 151                                                                  200
Mouse         RTGFLKIDEY  MRNFSDLRNG  MDRSGSTA..  .VGVMVSPTH  MYFI.NCGDS
Rat           RTGFLEIDEH  MRVMSEKKHG  ADRSGSTA..  .VGVLISPQH  TYFI.NCGDS
Yeast         NTKLVGNSGC  TAAVCVLRWE  LPDSVSDD..  .SMDLAQHQR  KLYTANVGDS
Leishmania    KELALRIDQ.  .....EWMDS  GREGGSTGTF  FVALKEGNKV  HLQVGNVGDS
FIN13         DTEEAEEDDD  EEMMVPGMEG  KEEPGSDSGT  TAVVALIRGK  QLIVANAGDS
```

FIG. 3B

```
           201
Mouse      RAVLCRNGQV CFSTQDHKPC NPVEKERIQN AGGSV.MIQR VNGSLAVSRA
Rat        RGLLCRNRKV HFFTQDHKPS NPLEKERIQN AGGSV.MIQR VNGSLAVSRA
Yeast      RIVLFRNGNS IRLTYDHKAS DTLEMQRVEQ AGGLI.MKSR VNGMLAVTRS
Leishmania RVVACIDGVC VPLTEDHKPN NEGERQRIEN CAGRV.ENNR VDGSLAVSRA
FIN13      RCVVSEAGKA LDMSYDHKPE DEVELARIKN AGGKVTMDGR VNGGLNLSRA
                                                              250

251                                                300
Mouse      LGDYDYKCVD GKGPTEQLVS PEPEVYEIVR AEEDE.FVVL ACDGIWDV.M
Rat        LGDFDYKCVH GKGPTEQLVS PEPEVHDIER SEEDDQFIIL ACDGIWDV.M
Yeast      LGDKFFDSLV VGSPFTTSVE ITSE...... .....DKFLIL ACDGLWDV.I
Leishmania FGDREYK.LG SGSQLEQKVI ALADVQHKDF TFDSNDFVLL CCDGVFEGNF
FIN13      IGDHFYKRNK NLPPQEQMIS ALPDIKVLTL T.DDHEFMVI ACDGIWNV.M 301                                                350
Mouse      SNEELCEFVK SRLEVSDD.. ....LENVCN WVVDTCLHKG SR........DN
Rat        GNEELCDFVR SRLEVTDD.. ....LEKVCN EVVDTCLYKG SR........DN
Yeast      DDQDACELIK DITEPNEA.. ......AK VLVRYALENG TT........DN
Leishmania PNEEVVAYVK QQLETCND.. ....LAEVAG RVCEEAIERG SR........DN
FIN13      SSQEVVDFIQ SKISQRDENG ELRLLSSIVE ELLDQCLAPD TSGDGTGCDN 351                                                400
Mouse      MSVVLVCFS. .NAPKVSEE. .......... .......... ....AVKRDS
Rat        MSVILICFP. .NAPKVSAE. .......... .......... ....AVKKEA
Yeast      VTVMVVFL*. .......... .......... .......... ..........
Leishmania ISCMIVQFK. .DGSDYAAEP HTTVVPGPFS APRNSGFRKA YESMADKGNT
FIN13      MTCIIICFKP RNTVELQAES GKRKLEEALS TEGAEDTGNS DKKKAKRD*.
```

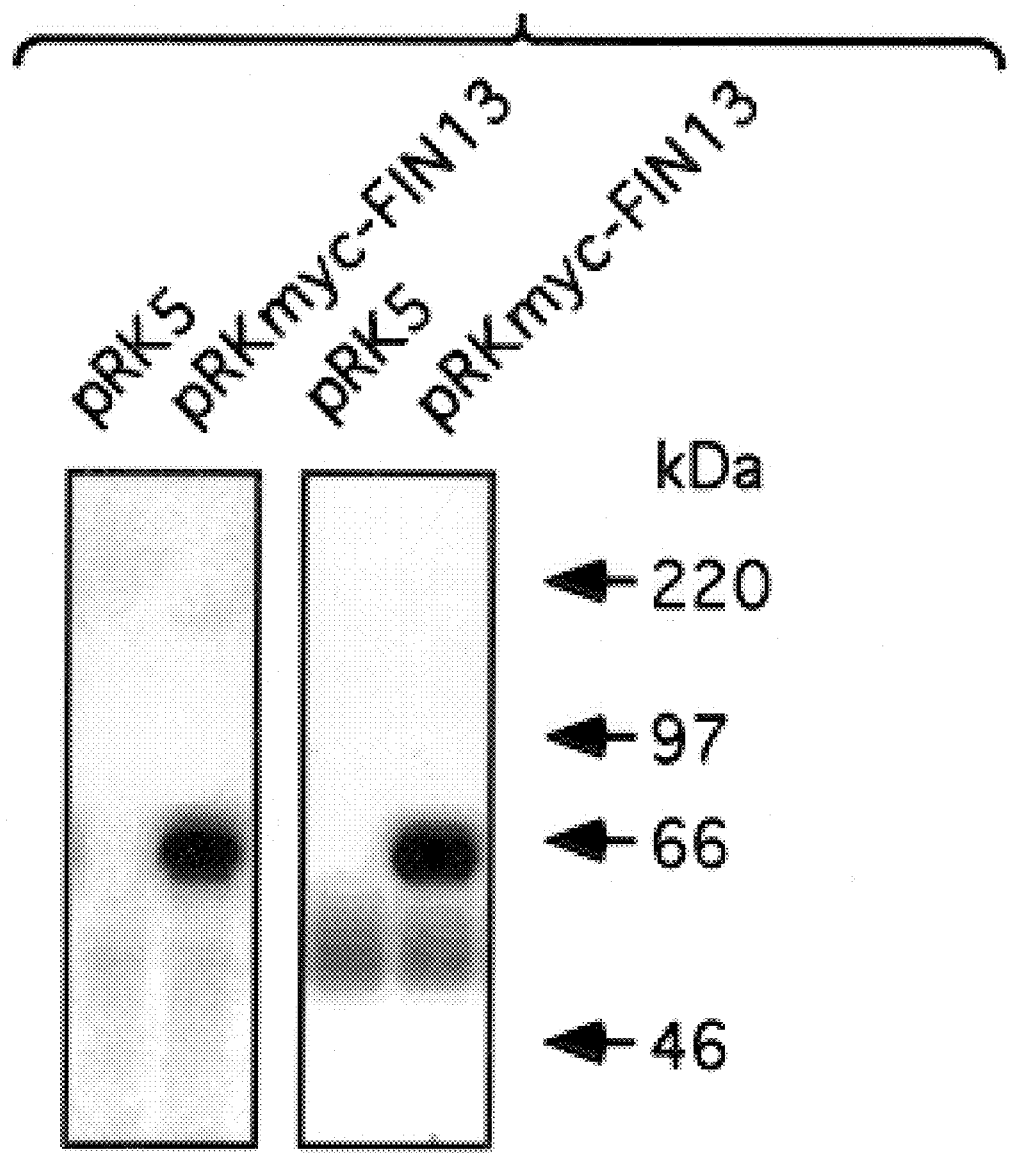

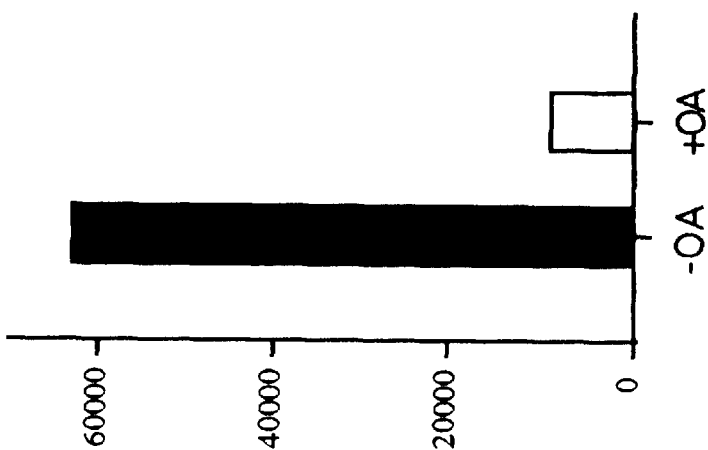
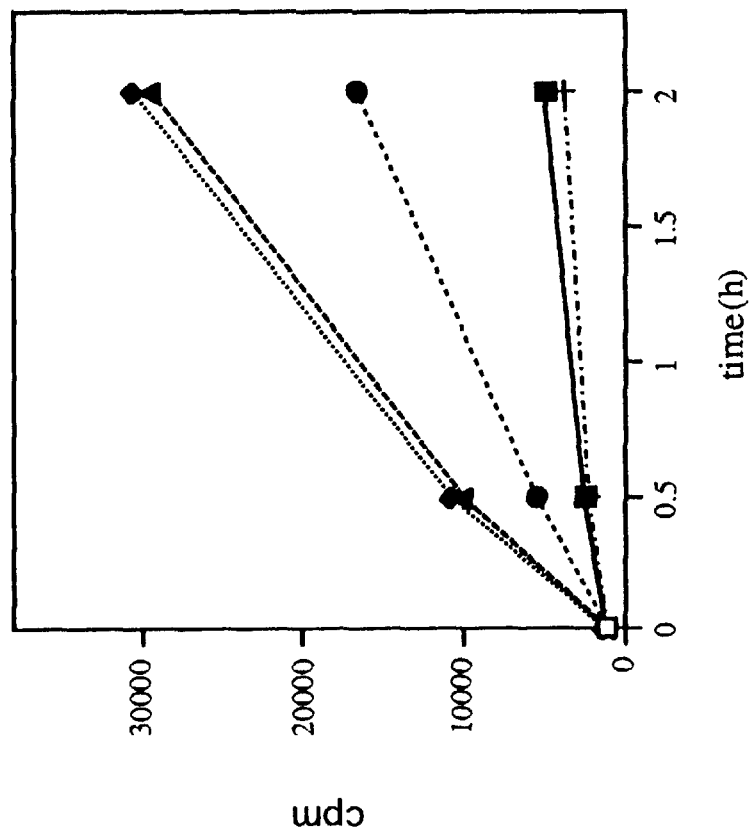

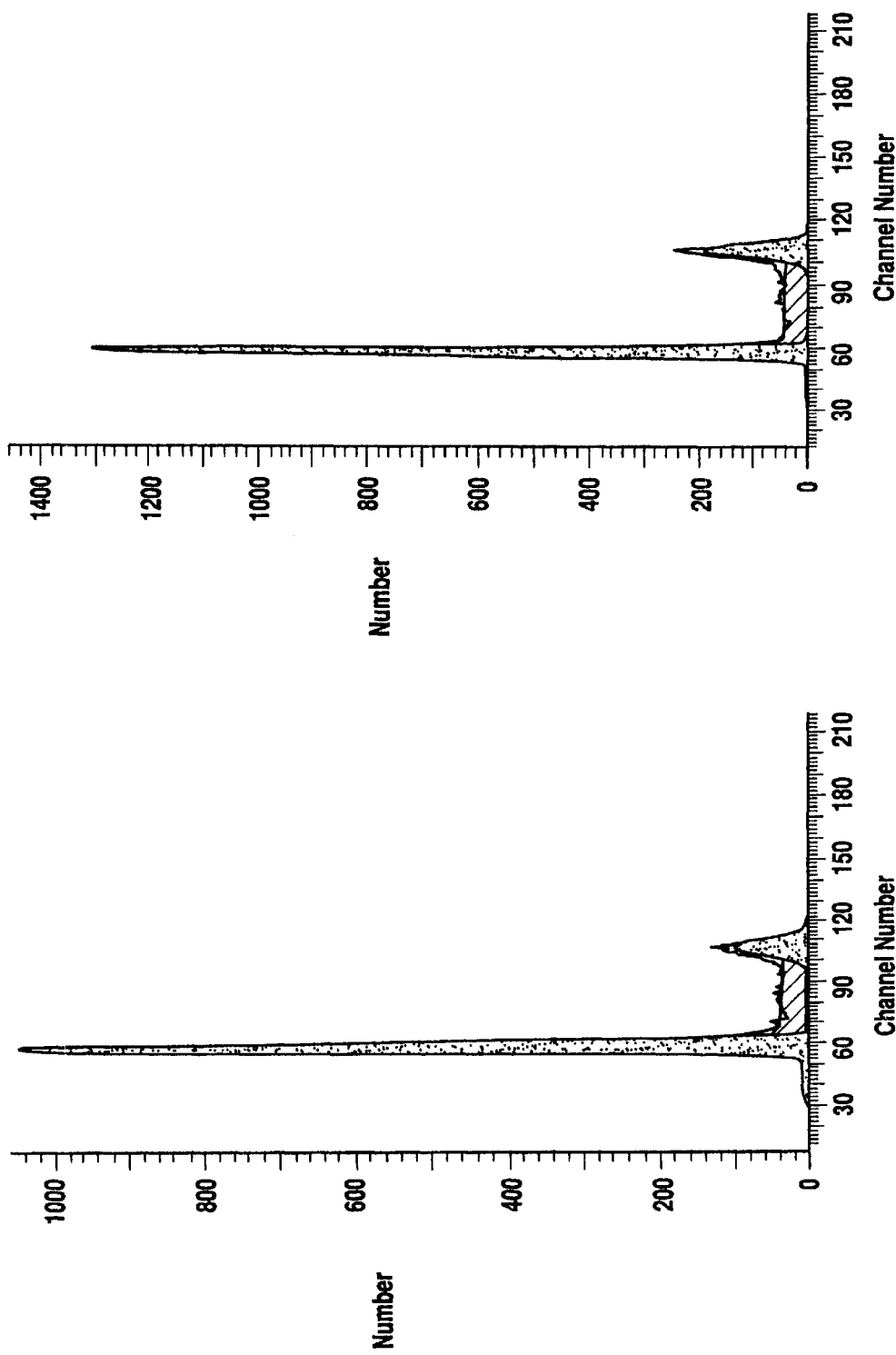

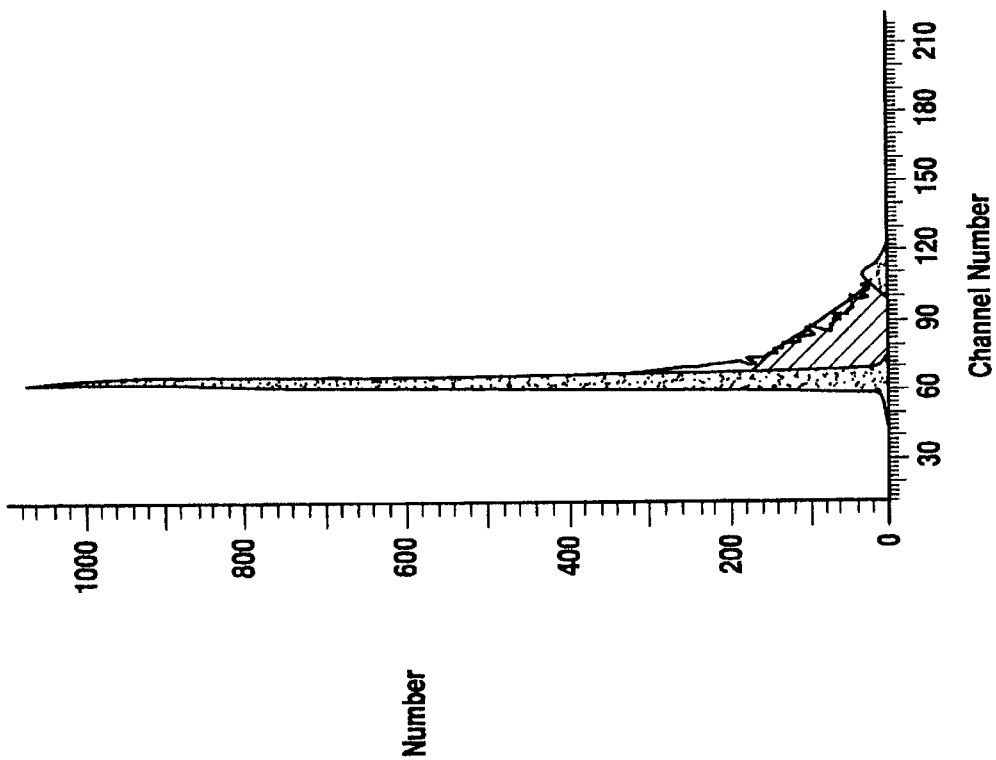

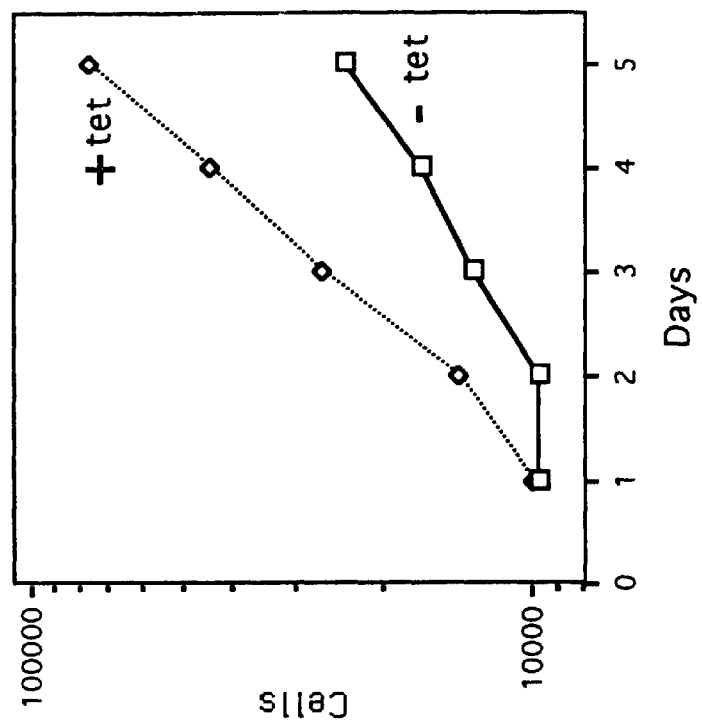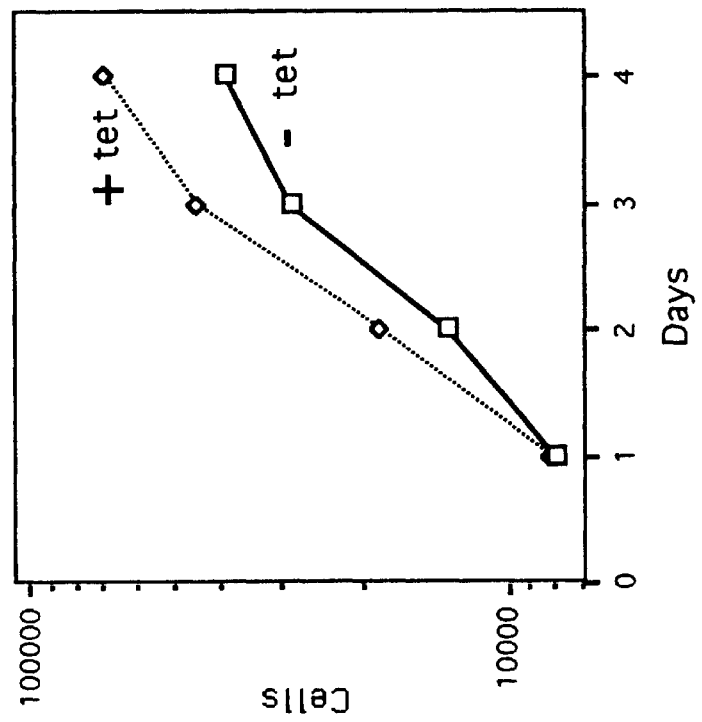

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1824 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GGCACGAGGA AGGCCTACAA GGAAGGCAAG CTTCAGAAGG CTTTACAAGA TGCCTTCTTG      60

GCTATTGATG CCAAGCTGAC CACAGAGGAA GTCATTAAGG AACTGGCCCA GATTGCAGGG     120

AGACCCACTG AAGATGAGGA TGATAAAGAC AAAGTAGCAG ATGAGGATGA TGTGGACAAT     180

GAGGAGGCTG CATTGTTGCA TGAAGAGGCT ACCATGACTA TTGAAGAGCT GCTGACGCGA     240

TATGGGCAGA ACTGTCAGAA GGTCCCTCCC CACACCAAAT CTGGAATTGG GACAGGCGAT     300
```

```
GAACCAGGGC CCCAGGGCCT CAATGGGGAG GCTGGACCTG AGGACCCATC TAGGGAAACT      360

CCTTCCCAGG AAAATGGCCC CACAGCCAAA GGCCACACAG GCTTTTCCTC CAACTCGGAA      420

CATGGGACTG AGGCAGGCCA AATTAGTGAG CCCGGTACTG CTACCGGTGA GGCTGGACCT      480

TCCTGCTCTT CAGCCTCTGA CAAGCTGCCT CGAGTTGCTA AGTCCAAGTT CTTTGAGGAC      540

AGTGAAGATG AATCAGATGA GGTGGAGGAA GAGGAGGATG ACAGTGAGGA ATGTAGTGAG      600

GACGAGGACG GCTACAGCAG TGAGGAGGCA GAGAACGAGG AAGACGAGGA TGACACGGAG      660

GAGGCTGAAG AGGATGATGA TGAAGAGATG ATGGTCCCTG GAATGGAAGG CAAAGAAGAG      720

CCTGGTTCTG ACAGTGGCAC AACAGCGGTG GTGGCTCTGA TCAGAGGGAA GCAGTTGATT      780

GTGGCCAATG CAGGAGACTC TCGCTGTGTG GTGTCCGAGG CTGGCAAAGC TTTAGATATG      840

TCCTATGACC ACAAACCAGA GGATGAAGTG GAGCTGGCAC GCATCAAGAA TGCTGGTGGC      900

AAGGTCACCA TGGATGGACG AGTCAATGGA GGCCTCAACC TCTCCAGGGC CATTGGAGAC      960

CACTTCTACA AGAGAAACAA AAACTTGCCA CCCCAGGAAC AGATGATTTC TGCCCTTCCT     1020

GACATCAAGG TGCTGACTCT CACTGATGAC CATGAATTCA TGGTCATTGC TTGTGACGGC     1080

ATCTGGAATG TGATGAGCAG CCAGGAGGTT GTAGACTTTA TTCAATCAAA GATCAGTCAA     1140

CGTGATGAAA ACGGGGAGCT TCGGTTATTG TCATCCATTG TGGAAGAGCT GCTGGATCAG     1200

TGCCTGGCGC CAGACACTTC TGGGGATGGT ACAGGGTGTG ACAACATGAC GTGCATCATC     1260

ATTTGCTTCA AGCCCCGAAA CACAGTAGAG CTTCAGGCAG AGAGTGGCAA GAGGAAACTG     1320

GAGGAGGCAC TGTCCACGGA GGGGGCTGAA GACACCGGCA ACAGTGACAA AAAGAAGGCC     1380

AAGAGGGACT AGTGGTCAAC CGGACCCTGC CCATGTGGAC TGTTTTCTGA GCCCTTGGAC     1440

CCGAGACTGA GTTTTGTCCT TGTCCTTTAG CCTTAGCAGT GGGTATGAGG TGTGCAGGGG     1500

GCTGGGTGGC TTTCCTCAGC CCATTACAAA GAGGGCCCCC CACCCCCCCC ACGCGGCAGC     1560

CTGGGAGGCT CTGCTGTCCT CTTAAGCCTC CTTACTCTCC TTGGGCTCAT CGACTATCGG     1620

TTCTGTGCCT GTGCTCTGTT GTGTTGGAGG GAAGGACTGG TAGTTCTGAT TTTTACTCTG     1680

TGAACACTTT ATTTAAGGAC ATTCTTTTTT ATTGGCGGCT CTGTGACCCC TAGCCGCTTG     1740

CACCCGCTCT CTGTTGTACA CTTTCAAGCA ACACTTTTTC AGACTAAAGG CCAAACAAAA     1800

GCTAAAAAAA AAAAAAAAAA AAAA                                            1824
```

(2) INFORMATION FOR SEQ ID NO:2:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO:2:

```
Met Thr Ile Glu Glu Leu Leu Thr Arg Tyr Gly Gln Asn Cys Gln Lys
1               5                   10                  15

Val Pro Pro His Thr Lys Ser Gly Ile Gly Thr Gly Asp Glu Pro Gly
            20                  25                  30

Pro Gln Gly Leu Asn Gly Glu Ala Gly Pro Glu Asp Pro Ser Arg Glu
        35                  40                  45

Thr Pro Ser Gln Glu Asn Gly Pro Thr Ala Lys Gly His Thr Gly Phe
    50                  55                  60
```

```
Ser Ser Asn Ser Glu His Gly Thr Glu Ala Gly Gln Ile Ser Glu Pro
 65              70                  75                  80

Gly Thr Ala Thr Gly Glu Ala Gly Pro Ser Cys Ser Ser Ala Ser Asp
             85                  90                  95

Lys Leu Pro Arg Val Ala Lys Ser Lys Phe Phe Glu Asp Ser Glu Asp
            100                 105                 110

Glu Ser Asp Glu Val Glu Glu Glu Asp Asp Ser Glu Glu Cys Ser
            115                 120                 125

Glu Asp Glu Asp Gly Tyr Ser Ser Glu Ala Glu Asn Glu Glu Asp
130                 135                 140

Glu Asp Asp Thr Glu Glu Ala Glu Glu Asp Asp Glu Glu Met Met
145                 150                 155                 160

Val Pro Gly Met Glu Gly Lys Glu Glu Pro Gly Ser Asp Ser Gly Thr
            165                 170                 175

Thr Ala Val Val Ala Leu Ile Arg Gly Lys Gln Leu Ile Val Ala Asn
            180                 185                 190

Ala Gly Asp Ser Arg Cys Val Val Ser Glu Ala Gly Lys Ala Leu Asp
            195                 200                 205

Met Ser Tyr Asp His Lys Pro Glu Asp Glu Val Glu Leu Ala Arg Ile
210                 215                 220

Lys Asn Ala Gly Gly Lys Val Thr Met Asp Gly Arg Val Asn Gly Gly
225                 230                 235                 240

Leu Asn Leu Ser Arg Ala Ile Gly Asp His Phe Tyr Lys Arg Asn Lys
                245                 250                 255

Asn Leu Pro Pro Gln Glu Gln Met Ile Ser Ala Leu Pro Asp Ile Lys
            260                 265                 270

Val Leu Thr Leu Thr Asp Asp His Glu Phe Met Val Ile Ala Cys Asp
            275                 280                 285

Gly Ile Trp Asn Val Met Ser Ser Gln Glu Val Val Asp Phe Ile Gln
            290                 295                 300

Ser Lys Ile Ser Gln Arg Asp Glu Asn Gly Glu Leu Arg Leu Leu Ser
305                 310                 315                 320

Ser Ile Val Glu Glu Leu Leu Asp Gln Cys Leu Ala Pro Asp Thr Ser
                325                 330                 335

Gly Asp Gly Thr Gly Cys Asp Asn Met Thr Cys Ile Ile Cys Phe
            340                 345                 350

Lys Pro Arg Asn Thr Val Glu Leu Gln Ala Glu Ser Gly Lys Arg Lys
            355                 360                 365

Leu Glu Glu Ala Leu Ser Thr Glu Gly Ala Glu Asp Thr Gly Asn Ser
370                 375                 380

Asp Lys Lys Lys Ala Lys Arg Asp
385                 390
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "Synthesized
            oligonucleotide"

(iii) HYPOTHETICAL: NO (iv) ANTI-SENSE: NO (xi) SEQUENCE DESCRIPTION: SEQ ID NO:3:

GAGGAATTCT CGAGCTCTAG AC                                                22

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "Synthesized
            oligonucleotide"

(iii) HYPOTHETICAL: NO (iv) ANTI-SENSE: NO (xi) SEQUENCE DESCRIPTION: SEQ ID NO:4:

GTCTAGAGCT CGAGAAT                                                      17

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GCTACCATGA                                                              10

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: mRNA (iii) HYPOTHETICAL: YES (iv) ANTI-SENSE: NO (xi) SEQUENCE DESCRIPTION: SEQ ID NO:6:

GCCRCCAUGG                                                              10

(2) INFORMATION FOR SEQ ID NO:7:

(i) SEQUENCE CHARACTERISTICS:
        (A) LENGTH: 309 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(vi) ORIGINAL SOURCE:

(A) ORGANISM: Mus musculus (xi) SEQUENCE DESCRIPTION: SEQ ID NO:7:

```
Met Gly Ala Phe Leu Asp Lys Pro Lys Thr Glu Lys His Asn Ala His
 1               5                  10                  15
Gly Ala Gly Asn Gly Leu Arg Tyr Gly Leu Ser Ser Met Gln Gly Trp
                20                  25                  30
Arg Val Glu Met Glu Asp Ala His Thr Ala Val Val Gly Ile Pro His
                35                  40                  45
Gly Leu Asp Asn Trp Ser Phe Phe Ala Val Tyr Asp Gly His Ala Gly
 50                  55                  60
Ser Arg Val Ala Asn Tyr Cys Ser Thr His Leu Leu Glu His Ile Thr
 65                  70                  75                  80
Thr Asn Glu Asp Phe Arg Ala Ala Asp Lys Ser Gly Ser Ala Leu Glu
                85                  90                  95
Pro Ser Val Glu Ser Val Lys Thr Gly Arg Thr Gly Phe Leu Lys Ile
                100                 105                 110
Asp Glu Tyr Met Arg Asn Phe Ser Asp Leu Arg Asn Gly Met Asp Arg
                115                 120                 125
Ser Gly Ser Thr Ala Val Gly Val Met Val Ser Pro Thr His Met Tyr
 130                 135                 140
Phe Ile Asn Cys Gly Asp Ser Arg Ala Val Leu Cys Arg Asn Gly Gln
 145                 150                 155                 160
Val Cys Phe Ser Thr Gln Asp His Lys Pro Cys Asn Pro Val Glu Lys
                165                 170                 175
Glu Arg Ile Gln Asn Ala Gly Gly Ser Val Met Ile Gln Arg Val Asn
                180                 185                 190
Gly Ser Leu Ala Val Ser Arg Ala Leu Gly Asp Tyr Asp Tyr Lys Cys
                195                 200                 205
Val Asp Gly Lys Gly Pro Thr Glu Gln Leu Val Ser Pro Glu Pro Glu
 210                 215                 220
Val Tyr Glu Ile Val Arg Ala Glu Glu Asp Glu Phe Val Val Leu Ala
 225                 230                 235                 240
Cys Asp Gly Ile Trp Asp Val Met Ser Asn Glu Glu Leu Cys Glu Phe
                245                 250                 255
Val Lys Ser Arg Leu Glu Val Ser Asp Asp Leu Glu Asn Val Cys Asn
                260                 265                 270
Trp Val Val Asp Thr Cys Leu His Lys Gly Ser Arg Asp Asn Met Ser
                275                 280                 285
Val Val Leu Val Cys Phe Ser Asn Ala Pro Lys Val Ser Glu Glu Ala
                290                 295                 300
Val Lys Arg Asp Ser
305
```

(2) INFORMATION FOR SEQ ID NO:8:

(i) SEQUENCE CHARACTERISTICS:
      (A) LENGTH: 306 amino acids
      (B) TYPE: amino acid
      (C) STRANDEDNESS: single
      (D) TOPOLOGY: linear (ii) MOLECULE TYPE: protein (iii) HYPOTHETICAL: NO (v) FRAGMENT TYPE:

(vi) ORIGINAL SOURCE:

(A) ORGANISM: Rattus (xi) SEQUENCE DESCRIPTION: SEQ ID NO:8:

```
Met Gly Ala Phe Leu Asp Lys Pro Lys Met Glu Lys His Asn Ala Gln
 1               5                  10                  15

Gly Gln Gly Asn Gly Leu Arg Tyr Gly Leu Ser Ser Met Gln Gly Trp
             20                  25                  30

Arg Val Glu Met Glu Asp Ala His Thr Ala Val Ile Gly Leu Pro Ser
         35                  40                  45

Gly Leu Glu Thr Trp Ser Phe Phe Ala Val Tyr Asp Gly His Ala Gly
     50                  55                  60

Ser Gln Val Ala Lys Tyr Cys Cys Glu His Leu Leu Asp His Ile Thr
65                  70                  75                  80

Asn Asn Gln Asp Phe Lys Gly Ser Ala Gly Ala Pro Ser Val Glu Asn
                 85                  90                  95

Val Lys Asn Gly Ile Arg Thr Gly Phe Leu Glu Ile Asp Glu His Met
            100                 105                 110

Arg Val Met Ser Glu Lys Lys His Gly Ala Asp Arg Ser Gly Ser Thr
        115                 120                 125

Ala Val Gly Val Leu Ile Ser Pro Gln His Thr Tyr Phe Ile Asn Cys
    130                 135                 140

Gly Asp Ser Arg Gly Leu Leu Cys Arg Asn Arg Lys Val His Phe Phe
145                 150                 155                 160

Thr Gln Asp His Lys Pro Ser Asn Pro Leu Glu Lys Glu Arg Ile Gln
                165                 170                 175

Asn Ala Gly Gly Ser Val Met Ile Gln Arg Val Asn Gly Ser Leu Ala
            180                 185                 190

Val Ser Arg Ala Leu Gly Asp Phe Asp Tyr Lys Cys Val His Gly Lys
        195                 200                 205

Gly Pro Thr Glu Gln Leu Val Ser Pro Glu Pro Glu Val His Asp Ile
    210                 215                 220

Glu Arg Ser Glu Glu Asp Asp Gln Phe Ile Ile Leu Ala Cys Asp Gly
225                 230                 235                 240

Ile Trp Asp Val Met Gly Asn Glu Glu Leu Cys Asp Phe Val Arg Ser
                245                 250                 255

Arg Leu Glu Val Thr Asp Asp Leu Glu Lys Val Cys Asn Glu Val Val
            260                 265                 270

Asp Thr Cys Leu Tyr Lys Gly Ser Arg Asp Asn Met Ser Val Ile Leu
        275                 280                 285

Ile Cys Phe Pro Asn Ala Pro Lys Val Ser Ala Glu Ala Val Lys Lys
    290                 295                 300

Glu Ala
305
```

(2) INFORMATION FOR SEQ ID NO:9:

(i) SEQUENCE CHARACTERISTICS:
        (A) LENGTH: 281 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(vi) ORIGINAL SOURCE:

(A) ORGANISM: Saccharomyces cerevisiae (xi) SEQUENCE DESCRIPTION: SEQ ID NO:9:

```
Met Ser Asn His Ser Glu Ile Leu Glu Arg Pro Glu Thr Pro Tyr Asp
1               5                   10                  15

Ile Thr Tyr Arg Val Gly Val Ala Glu Asn Lys Asn Ser Lys Phe Arg
            20                  25                  30

Arg Thr Met Glu Asp Val His Thr Tyr Val Lys Asn Phe Ala Ser Arg
        35                  40                  45

Leu Asp Trp Gly Tyr Phe Ala Val Phe Asp Gly His Ala Gly Ile Gln
    50                  55                  60

Ala Ser Lys Trp Cys Gly Lys His Leu His Thr Ile Ile Glu Gln Asn
65              70                  75                  80

Ile Leu Ala Asp Glu Thr Arg Asp Val Arg Asp Val Leu Asn Asp Ser
                85                  90                  95

Phe Leu Ala Ile Asp Glu Glu Ile Asn Thr Lys Leu Val Gly Asn Ser
            100                 105                 110

Gly Cys Thr Ala Ala Val Cys Val Leu Arg Trp Glu Leu Pro Asp Ser
        115                 120                 125

Val Ser Asp Ser Met Asp Leu Ala Gln His Gln Arg Lys Leu Tyr
    130                 135                 140

Thr Ala Asn Val Gly Asp Ser Arg Ile Val Leu Phe Arg Asn Gly Asn
145                 150                 155                 160

Ser Ile Arg Leu Thr Tyr Asp His Lys Ala Ser Asp Thr Leu Glu Met
            165                 170                 175

Gln Arg Val Glu Gln Ala Gly Gly Leu Ile Met Lys Ser Arg Val Asn
        180                 185                 190

Gly Met Leu Ala Val Thr Arg Ser Leu Gly Asp Lys Phe Phe Asp Ser
    195                 200                 205

Leu Val Val Gly Ser Pro Phe Thr Thr Ser Val Glu Ile Thr Ser Glu
    210                 215                 220

Asp Lys Phe Leu Ile Leu Ala Cys Asp Gly Leu Trp Asp Val Ile Asp
225             230                 235                 240

Asp Gln Asp Ala Cys Glu Leu Ile Lys Asp Ile Thr Glu Pro Asn Glu
            245                 250                 255

Ala Ala Lys Val Leu Val Arg Tyr Ala Leu Glu Asn Gly Thr Thr Asp
        260                 265                 270

Asn Val Thr Val Met Val Val Phe Leu
    275                 280
```

(2) INFORMATION FOR SEQ ID NO:10:

(i) SEQUENCE CHARACTERISTICS:
        (A) LENGTH: 314 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(vi) ORIGINAL SOURCE:
        (A) ORGANISM: Leishmania (xi) SEQUENCE DESCRIPTION: SEQ ID NO:10:

```
Met Gly Ile Pro Leu Pro Lys Pro Val Met Thr Gln Leu Gln Glu Arg
1               5                   10                  15
```

```
Tyr Gly Asn Ala Ile Phe Arg Cys Gly Ser Asn Cys Val Asn Gly Tyr
                20                  25                  30

Arg Glu Thr Met Glu Asp Ala His Leu Thr Tyr Leu Thr Asp Ser Trp
            35                  40                  45

Gly Phe Phe Gly Val Phe Asp Gly His Val Asn Asp Gln Cys Ser Gln
        50                  55                  60

Tyr Leu Glu Arg Ala Trp Arg Ser Ala Ile Glu Lys Glu Ser Ile Pro
65                  70                  75                  80

Met Thr Asp Glu Arg Met Lys Glu Leu Ala Leu Arg Ile Asp Gln Glu
                85                  90                  95

Trp Met Asp Ser Gly Arg Glu Gly Gly Ser Thr Gly Thr Phe Phe Val
                100                 105                 110

Ala Leu Lys Glu Gly Asn Lys Val His Leu Gln Val Gly Asn Val Gly
            115                 120                 125

Asp Ser Arg Val Val Ala Cys Ile Asp Gly Val Cys Val Pro Leu Thr
        130                 135                 140

Glu Asp His Lys Pro Asn Asn Glu Gly Glu Arg Gln Arg Ile Glu Asn
145                 150                 155                 160

Cys Ala Gly Arg Val Glu Asn Asn Arg Val Asp Gly Ser Leu Ala Val
                165                 170                 175

Ser Arg Ala Phe Gly Asp Arg Glu Tyr Lys Leu Gly Ser Gly Ser Gln
                180                 185                 190

Leu Glu Gln Lys Val Ile Ala Leu Ala Asp Val Gln His Lys Asp Phe
            195                 200                 205

Thr Phe Asp Ser Asn Asp Phe Val Leu Leu Cys Cys Asp Gly Val Phe
        210                 215                 220

Glu Gly Asn Phe Pro Asn Glu Glu Val Val Ala Tyr Val Lys Gln Gln
225                 230                 235                 240

Leu Glu Thr Cys Asn Asp Leu Ala Glu Val Ala Gly Arg Val Cys Glu
                245                 250                 255

Glu Ala Ile Glu Arg Gly Ser Arg Asp Asn Ile Ser Cys Met Ile Val
                260                 265                 270

Gln Phe Lys Asp Gly Ser Asp Tyr Ala Ala Glu Pro His Thr Thr Val
            275                 280                 285

Val Pro Gly Pro Phe Ser Ala Pro Arg Asn Ser Gly Phe Arg Lys Ala
        290                 295                 300

Tyr Glu Ser Met Ala Asp Lys Gly Asn Thr
305                 310
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE:

(xi) SEQUENCE DESCRIPTION: SEQ ID NO:11:

```
Val Ser Arg Lys Arg Pro Arg Pro
1               5
```

(2) INFORMATION FOR SEQ ID NO:12:

(i) SEQUENCE CHARACTERISTICS:
     (A) LENGTH: 7 amino acids
     (B) TYPE: amino acid
     (C) STRANDEDNESS: single
     (D) TOPOLOGY: linear (ii) MOLECULE TYPE: peptide (iii) HYPOTHETICAL: NO (v) FRAGMENT TYPE:

(xi) SEQUENCE DESCRIPTION: SEQ ID NO:12:

```
Pro Lys Lys Lys Arg Lys Val
1               5
```

(2) INFORMATION FOR SEQ ID NO:13:

(i) SEQUENCE CHARACTERISTICS:
     (A) LENGTH: 27 amino acids
     (B) TYPE: amino acid
     (C) STRANDEDNESS: single
     (D) TOPOLOGY: linear (ii) MOLECULE TYPE: peptide (iii) HYPOTHETICAL: NO (v) FRAGMENT TYPE: C-terminal (xi) SEQUENCE DESCRIPTION: SEQ ID NO:13:

```
Lys Arg Lys Leu Glu Glu Ala Leu Ser Thr Glu Gly Ala Glu Asp Thr
1               5                   10                  15
Gly Asn Ser Asp Lys Lys Lys Ala Lys Arg Asp
            20                  25
```

(2) INFORMATION FOR SEQ ID NO:14:

(i) SEQUENCE CHARACTERISTICS:
     (A) LENGTH: 32 base pairs
     (B) TYPE: nucleic acid
     (C) STRANDEDNESS: single
     (D) TOPOLOGY: linear (ii) MOLECULE TYPE: other nucleic acid
     (A) DESCRIPTION: /desc = "Synthesized
         oligonucleotide"

(iii) HYPOTHETICAL: NO (iv) ANTI-SENSE: NO (xi) SEQUENCE DESCRIPTION: SEQ ID NO:14:

```
GAGAGGATCC CATGACTATT GAAGAGCTGC TG                          32
```

(2) INFORMATION FOR SEQ ID NO:15:

(i) SEQUENCE CHARACTERISTICS:
     (A) LENGTH: 35 base pairs
     (B) TYPE: nucleic acid
     (C) STRANDEDNESS: single
     (D) TOPOLOGY: linear (ii) MOLECULE TYPE: other nucleic acid
     (A) DESCRIPTION: /desc = "Synthesized
         oligonucleotide"

(iii) HYPOTHETICAL: NO (iv) ANTI-SENSE: NO (xi) SEQUENCE DESCRIPTION: SEQ ID NO:15:

```
CTCTCGCGGC CGCGTCCCTC TTGGCCTTCT TTTTG                                      35

(2) INFORMATION FOR SEQ ID NO:16:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO:16:

TCGAGGCCAC CATGACTATT GAAGAGCTGC TGACGCGATA T                               41

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO:17:

TGCCCATATC GCGTCAGCAG CTCTTCAATA GTCATGGTGG CC                              42

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO:18:

CGATGCCACC ATGGAACAGA AACTGATTTC CGAAGAAGAT CTGAT                           45
```

GROWTH FACTOR INDUCIBLE SERINE/ THREONINE PHOSPHATASE FIN13

PRIORITY CLAIM

The present application is a non-provisional application that claims priority pursuant to 35 U.S.C. § 119(e) to provisional application Ser. No. 60/013792, filed Mar. 21, 1996 which is incorporated herein by reference in its entirety.

The research leading to the present invention was supported, in part, by Public Health Service Grant CA42568 from the National Cancer Institute, and National Institutes of Health Grant No. H600734. Accordingly, the Government may have certain rights in the invention.

FIELD OF THE INVENTION

The present invention relates to the modulation of cellular proliferation by regulating the activity of a novel serine/threonine phosphatase. Thus, the invention provides the phosphatase, nucleic acids encoding the phosphatase, oligonucleotides specific for such nucleic acids, antibodies to the phosphatase, and methods for increasing (or decreasing) the activity of the phosphatase to inhibit (or enhance) cellular proliferation and, thus, tissue growth. Various diagnostic and therapeutic aspects of the invention particularly relate to detection and treatment of hyperproliferative disorders, neoplastics, and tumors.

BACKGROUND OF THE INVENTION

The molecular mechanisms by which basic fibroblast growth factor (bFGF) and K-FGF stimulate a wide range of biological responses in normal and transformed tissues are not well understood. Although bFGF and K-FGF are proposed to serve multiple roles in normal and transformed tissues, the mechanisms by which bFGF/K-FGF exert their effects are largely undetermined. Identification of the genes induced by bFGF and K-FGF is critical for understanding the mechanisms regulating the biological activities of these growth factors in normal and neoplastic tissues.

Biological Activities of bFGF and K-FGF bFGF and K-FGF simulate a wide range of biological responses in normal and transformed cells. Although the biological properties of the FGF family of polypeptides are well described in the literature (Basilico and Moscatelli, 1992, *Adv. Cancer Res.*, 59:115–165; Burgess and Maciag, 1989, *Annu. Rev. Biochem.*, 58:575–606; Hearn, 1991, *Bailliere's Clin. Endo. Metab.*, 5:571–593; Yoshida et al., 1991, *Annals N.Y. Acad. Sci.*, 638:27–37), these background discussions will focus on the activities of bFGF and K-FGF. bFGF is a potent mitogen for a wide range of cell types in vitro and stimulates neovascularization in vivo (Basilico and Moscatelli, supra; Burgess and Maciag, supra). The mitogenic and angiogenic activities of bFGF are thought to reflect a possible wound healing role for the growth factor (Burgess and Maciag, supra). For example, bFGF is proposed to be important in stimulating muscle regeneration following ischemic injury (Guthridge et al., 1992, *Growth Factors*, 6:53–63). Other biological activities have been ascribed for this growth factor. The ability of bFGF to promote long-term neuronal survival and neurite outgrowth in vitro suggests possible neurotrophic functions in the central nervous system (Burgess and Maciag, supra). In vitro studies have also demonstrated that bFGF not only stimulates porcine and rat granulosa cell proliferation but also attenuates their FSH-mediated differentiation and thus may serve mitogenic and non-mitogenic roles in collicular ontogeny (Hearn, supra). Indeed, the modulation of bFGF mRNA levels in the rat ovary correlates with the occurrence of granulosa cell proliferation and corpus luteum vascularization (Guthridge et al., 1992, *Growth Factors*, 7:15–25). It has also been proposed that bFGF has a fundamental role in regional specification and cellular differentiation in the developing embryo. Exogenous bovine bFGF can induce mesoderm formation in ectoderm explants from early Xenopus embryos similar to the mesodermal structures induced in vivo (Basilico and Moscatelli, supra; Burgess and Maciag, supra).

Although K-FGF has not been as extensively studied as bFGF, both growth factors exhibit overlapping biological activities. K-FGF is a potent mitogen in vitro and simulates neovascularization in vivo (Yoshida et al., supra). The physiological expression of K-FGF appears to be restricted to embryonic tissues and mesoderm inducing activity in Xenopus embryos has also been observed for K-FGF (Basilico and Moscatelli, supra).

In addition to the diverse functions proposed for bFGF and KFGF in normal tissues, there is evidence to suggest that the mitogenic and angiogenic properties of these growth factors may promote the persistent and autologous growth of transformed tissues. An ever-increasing number of malignant tissues and tumor-derived cell lines have been identified as synthesizing bFGF mRNA or polypeptides (Schweigerer, 1988, *Klin Wochenschr*, 66:340–345), and the acquisition of constitutive bFGF mRNA expression is thought to contribute to the unregulated angiogenesis and persistent autocrine stimulation of cell proliferation in malignant melanomas (Basilico and Moscatelli, 1992, supra). While the prevalence of K-FGF mRNA expression in transformed tissues has not been fully determined, K-FGF mRNA has been detected in human and mouse germ cell tumors (Yoshida et al., supra) and human and mouse mammary tumors (Basilico and Moscatelli, supra). Transfection of NIH 3T3 cells with vectors that constitutively express K-FGF cDNAs induces morphological transformation in vitro (Basilico and Moscatelli, supra). Furthermore, these K-FGF transformed cells induced the formation of highly vascularized tumors when injected subcutaneously in immunocompetent mice indicating that the K-FGF gene has high transforming potential (Basilico and Moscatelli, supra).

Despite the broad range of biological activities attributed to bFGF and K-FGF and their proposed roles in such clinically significant processes as wound healing, follilculogenesis, formation of the corpus luteum, embryogenesis and tumorigenesis, the mechanisms by which bFGF/K-FGF exert their effects are largely undetermined.

Mechanisms of bFGF and K-FGF Stimulation

The cellular actions of the FGFs are exerted through binding with cell surface receptors which results in the transfer of appropriate signals to the nucleus leading to the pleiotropic response required to modulate cell proliferation and differentiation. A complex picture is emerging in which ligand-receptor interaction at the cell surface activates a number of signaling cascades which in turn activates the genetic program required to mediate the cellular response. Identification of the genes induced by bFGF and K-FGF are critical for understanding the mechanisms regulating the diverse biological activities of these growth factors in normal and transformed tissues.

The first genes to be activated following growth factor stimulation are the immediate-early genes and include known or putative transcription factors. The most widely studied of these growth factor-responsive genes are c-fos, c-jun, and c-myc. Depending on the cell line, activation of c-fos transcription has been observed following a wide range of stimuli including bFGF, platelet-derived growth factor (PDGF), epidermal growth factor (EGF), nerve growth factor (NGF), tumor necrosis factor-α, transforming growth factor-β (TGF-β) and cAMP (Angel, P. and Karin, M., 1991, *Biochem. Biophys. Acta*, 1072:129–157). The transcription of c-jun and c-myc are also induced by a wide variety of factors such as bFGF, EGF, NGF, PDGF, TGF-β, and insulin in a variety of cell types (Ito et al., 1990, *Oncogene*, 5:1755–1760; Li et al., 1990, *J. Biol. Chem.*, 265:1556–1562; Kelly et al., 1983, *Cell*, 35:603–610). The expression of other immediate-early and later genes such as TIS genes (Lim et al., 1989, *Mol. Cell. Biol.*, 9:1790–1793), Krox-24/Egr-1/Zif-268/NGFl-A and Krox-20/Egr-2 (Ito et al., supra; Sukhatme et al., 1987, *Oncogene Res.*, 1:343–355; Lemaire et al., 1988, *Proc. Natl. Acad. Sci. U.S.A.*, 85:4691–4695; Chavrier et al., 1988, *EMBO J.*, 7:29–35) are also induced by a wide variety of growth factors.

It has been suggested that these growth factor-responsive genes play a pivotal role in growth regulation and cellular differentiation, however, current understanding of the diverse range of cellular responses reported for growth factors such as the FGFs presents an intriguing paradox. Growth factor-receptor binding is a highly specific interaction which often activates a specific cellular response. Although it may be anticipated that the diverse biological activities of polypeptide growth factors are mediated by multiple convergent and non-convergent pathways that activate both common and unique cellular genes, expression of genes uniquely induced by the FGFs has not been identified.

A number of studies have reported that heterologous growth factors which stimulate different responses in a given cell type activate the transcription of equivalent sets of genes. An example of this apparent lack of specificity is evident in the growth factor response of the rat pheochromocytoma cell line, PC-12. NGF and bFGF induce growth arrest of PC12 cells which then differentiate into sympathetic neuron-like cells, whilst EGF is mitogenic for PC-12 cells and does not induce differentiation (Bartel et al., 1989, *Genes Dev.*, 3:304–313). Despite the disparate biological effects of NGF and bFGF when compared to EGF, each growth factor activates a similar set of immediate-early genes which include c-fos, c-jun, jun-B and Zif/268 (Bartel et al., supra). That there are no discernable differences in the transcriptional programs activated by these growth factors in PC-12 cells would indicate that other, as yet undiscovered genes, are differentially activated according to the mitogenic/differentiative nature of the signal. The ability of bFGF and K-FGF to evoke a wide range of cellular responses, often unique with respect to the activities of other polypeptide growth factors, would indicate the following: the specialized activity of polypeptide growth factors is contingent upon their ability to activate a specific genetic program which culminates in a unique cellular response. Furthermore, signal transduction pathways must operate to activate the transcription of growth factor specific genes, other than those of the fos, jun and myc families, that are crucial in mediating the specific cellular response to growth factor stimulation. Gene expression specifically activated by the FGFs has not been systematically explored and remains to be elucidated.

More recently, support for the existence of growth factor-specific inducible genes has been reported. NGF and bFGF induce differentiation of PC12 cells and also specifically activate transcription of the SCG10 gene. However, induction of SCG10 expression does not occur in response to EGF, which is mitogenic for PC12 cells (Stein, R., et al., 1988, *Dev. Biolo.*, 127:316–325). SCG10 exhibits neural specific expression and may be important in mediating the neurotrophic activities of NGF and bFGF. Other studies have reported that the expression of N51 in NIH 3T3 cells is specifically induced by PDGF and not significantly by EGF and bFGF (Ryseck, R. P., et al., 1989, *Exp. Cell Res.*, 180:266–275). While the function of the N51 protein remains uncertain, it is proposed to be a secretory cytosine.

The known diverse biological properties of bDFGF and K-FGF evidence the potential to satisfy many of the requirements of tumorigenesis. These properties include the ability to stimulate cell proliferation and angiogenesis. Although physiological requirements exist for these processes in wound healing, female reproductive competence, and embryogenesis, the mechanisms by which bFGF and K-FGF direct normal and aberrant cell behavior remains largely undetermined. Clearly, the challenge is to determine the genes regulated by these growth factors in normal and transformed tissues. The identification of genes specifically induced by bFGF and K-FGF in transformed cells will enable a better understanding of cellular transformation and the factors that govern malignant cell replication. Such an understanding of how bFGF and K-FGF-induced genes interdigitate with cellular response elements and mediate normal and aberrant cellular behavior may have exciting clinical implications for the development of treatment regimes for neoplastic pathologies.

Thus, there is a need in the art to characterize bFGF and K-FGF-induced genes and their gene products.

There is a further need to identify the roles these genes and their encoded proteins play in tumorigenesis.

The present invention addresses these and similar needs in the art by the identification and characterization of a novel FGF-inducible serine/threonine phosphatase.

The citation of any reference herein should not be construed as an admission that such reference is available as prior art to the invention.

SUMMARY OF THE INVENTION

The present invention is broadly directed to an isolated FIN13 serine/threonine phosphatase having a collagen-homology domain, an acidic box domain, a serine/threonine phosphatase domain, and a charged domain characteristic of a putative nuclear localization sequence. In a specific embodiment, FIN13 has an amino acid sequence as depicted in FIG. 1 (SEQ ID NO:2).

FIN13 is expressed as a result of cellular growth. The present inventors have found that FIN13 inhibits growth, and thus appears to play a role in regulating growth and cellular proliferation. Thus, the present invention advantageously provides a materials capable of modulating uncontrolled cell growth. Indeed, FIN13 is an excellent candidate as a tumor suppressor protein.

The invention further relates to a polypeptide domain fragment of FIN13. For example, in one aspect the invention provides a fragment of FIN13 comprising a serine/threonine phosphatase catalytic domain. In a specific embodiment, the serine/threonine phosphatase catalytic domain of the invention is characterized by having: 46% sequence identity with a type 2C phosphatase catalytic domain from *S. cerevisiae*; 45% sequence identity with a type 2C phosphatase catalytic domain from *C. elegans*; 38% sequence identity with a type 2C phosphatase catalytic domain from rat; 36% sequence identity with a type 2C phosphatase catalytic domain from rabbit; and 35% sequence identity with a type 2C phosphatase catalytic domain from murine PP2C1 phosphatase. In a more specific embodiment, the fragment has an amino acid sequence as depicted in FIG. 1 (SEQ ID NO:2) from about residue number 174 to about residue number 352, with numbering beginning with methionine-1.

In another embodiment of fragments of FIN13, the fragment is a collagen-homology domain of approximately 100 amino acid residues. In a specific embodiment, the collagen-homology domain is characterized by having: 29% sequence identity over 104 amino acids with mouse alpha-2 (IV) collagen; and 29% sequence identity over 108 amino acids with chicken alpha-3 (IX) collagen. In a more specific embodiment, the collagen-homology domain has an amino acid sequence as depicted in FIG. 1 (SEQ ID NO:2) from about residue number 1 to about residue number 100, with numbering beginning with methionine-1.

Another aspect of the fragments of the invention relates to a fragment of FIN13 comprising a central acidic box rich in aspartic acid and glutamic acid residues. Preferably, this fragment has sequence similarity to the acidic domain of transcription factors, such as UBF-1. In a specific embodiment, the acidic box domain has an amino acid sequence as depicted in FIG. 1 (SEQ ID NO:2) from about residue number 108 to about residue number 169, with numbering beginning with methionine-1.

The invention further provides proteins consisting of any combination of the foregoing domains, e.g., the collagen-homology domain with the acidic box domain, the collagen-homology domain or the acidic box domain with the catalytic domain, or any of the foregoing with a nuclear translocation peptide.

The present invention further relates to a chimeric protein comprising the protein or fragment thereof. In specific embodiments, infra, such a chimeric protein consists of maltose binding protein or poly-histidine with FIN13 or the catalytic domain of FIN13. However, the invention specifically contemplates chimeric proteins comprising a targeting moiety, preferably an intracellular targeting moiety, with FIN13.

Naturally, in addition to the isolated protein and fragments thereof, the invention provides a purified nucleic acid encoding a FIN13 serine/threonine kinase having a collagen-homology domain, an acidic box, a serine/threonine phosphatase domain, and a charged domain characteristic of a putative nuclear localization sequence, or a fragment thereof having at least 15 nucleotides. In a specific embodiment, the nucleic acid encodes FIN13 having an amino acid sequence as depicted in FIG. 1 (SEQ ID NO:2). In a more specific embodiment, the nucleic acid has a nucleotide sequence as depicted in FIG. 1 (SEQ ID NO:1) from nucleotide 214 to nucleotide 389. The invention further provides 5' and 3' non-coding sequences, as depicted in FIG. 1 and SEQ ID NO:1.

The present invention further provides nucleic acids encoding a fragment of FIN13, particularly the serine/threonine phosphatase catalytic domain, in which case in a specific embodiment the nucleic acid has a nucleotide sequence as depicted in FIG. 1 (SEQ ID NO:1) from nucleotide 732 to nucleotide 1269; the collagen-homology domain of approximately 100 amino acid residues, in which case in a specific embodiment the nucleic acid has a nucleotide sequence as depicted in FIG. 1 (SEQ ID NO:1) from nucleotide 214 to nucleotide 513; and the acidic box domain rich in aspartic acid and glutamic acid residues, in which case in a specific embodiment the nucleic acid has a sequence as depicted in FIG. 1 (SEQ ID NO:1) from nucleotide 538 to nucleotide 720.

In a specific embodiment, the purified nucleic acid is DNA. The DNA may be provided in a recombinant DNA vector. Preferably, the DNA vector is an expression vector, wherein the DNA encoding the FIN13 is operatively associated with an expression control sequence, whereby transformation of a host cell with the expression vector provides for expression of FIN13, or a fragment thereof as set forth above. Thus, the invention further provides a transformed host cell comprising the DNA vector. In a specific embodiment, the host cell is a bacterial cell. In another specific embodiment, the host cell is a mammalian cell.

The invention further provides a recombinant virus comprising the DNA expression vector. The recombinant virus may be selected from the group consisting of a retrovirus, herpes simplex virus (HSV), papillomavirus, Epstein Barr virus (EBV), adenovirus, and adeno-associated virus (AAV).

Corollary to the recombinant DNA expression vectors, the invention provides a method for producing a FIN13 comprising expressing the expression vector in a recombinant host cell of the invention under conditions that provide for expression of the FIN13. The methods of expression of the invention may be practiced, for example, in a bacterium, or in a mammalian cell.

The nucleic acids of the invention also provide a method for increasing the level of expression of a FIN13. Accordingly, an expression vector may be introduced into a host in vivo under conditions that provide for expression of the FIN13. In one embodiment, the expression vector is a viral expression vector. In another embodiment, the expression vector is a naked DNA expression vector.

The invention further provides a method for treating a disease or disorder associated with uncontrolled cellular proliferation in a mammal, comprising increasing the level of FIN13 in cells demonstrating uncontrolled proliferation, wherein the FIN13 serine/threonine kinase has a collagen-homology domain, an acidic box, a serine/threonine phosphatase domain, and a charged domain characteristic of a putative nuclear localization sequence. In one embodiment, the level of FIN13 is increased by administration of FIN13. In another embodiment, the level of FIN13 is increased by administration of a recombinant expression vector to the cells demonstrating uncontrolled proliferation, which expression vector provides for expression of the FIN13 in vivo. In one embodiment, the expression vector is a viral expression vector; alternatively, the expression vector is a naked DNA expression vector.

In addition to therapeutic aspects, the present invention provides oligonucleotides and antibodies for detection of FIN13, and diagnosis of conditions associated with increased or decreased levels of FIN13 expression.

Thus, in one aspect, the invention provides an oligonucleotide of greater than 20 nucleotides which hybridizes under stringent conditions to the nucleic acid encoding FIN13. Preferably, the oligonucleotide hybridizes under conditions wherein the $T_m$ is greater than 60° C. More preferably, the oligonucleotide hybridizes at a $T_m$ of greater than 65° C. In another embodiment, the oligonucleotide hybridizes at 40% formamide, with 5× or 6× SCC. In a specific embodiment, exemplified infra, the oligonucleotide is an antisense oligonucleotide that hybridizes to fin13 mRNA.

In another aspect, the invention provides an antibody specific for FIN13. The antibody may be polyclonal or monoclonal. In a specific embodiment, exemplified infra, the antibody is a rabbit polyclonal antibody generated against a FIN13 fusion protein. In a specific embodiment, the antibody is labeled, e.g., with a label selected from the group consisting of a radioisotope, an enzyme, a chelating agent, a fluorophore, a chemiluminescent molecule, and a particle.

The oligonucleotides and antibodies of the invention can be used to detect the presence or level of FIN13, or nucleic acids encoding it, in a biological sample. In one embodiment, the invention provides a method for detecting FIN13 in a biological sample comprising contacting a biological sample with an antibody specific for FIN13 under conditions that allow for antibody binding to antigen; and detecting formation of reaction complexes comprising the antibody and FIN13 in the sample. The detection of formation of reaction complexes indicates the presence of FIN13 in the sample. The level of FIN13 can be quantitated by evaluating the amount of reaction complexes formed, wherein the amount of reaction complexes corresponds to the level of FIN13 in the biological sample. Alternatively, a method for detecting FIN13 mRNA in a biological sample comprises contacting a biological sample with an oligonucleotide of the invention under conditions that allow for hybridization with mRNA; and detecting hybridization of the oligonucleotide to mRNA in the sample. The detection of hybridization indicates the presence of Fin13 mRNA in the sample. The level of expression of fin13 mRNA can be determined by evaluating the quantity of oligonucleotide hybridized, wherein the quantity of oligonucleotide hybridized corresponds to the level of FIN13 in the biological sample.

Thus, a primary object of the invention is to provide a novel protein involved in modulation of cell growth, particularly cell growth associated with fibroblast growth factor or other growth factors.

Another object of the invention is to provide a nucleic acid, preferably a DNA molecule, coding for such a protein.

Still another object of the invention is to modulate cell growth by agonizing or antagonizing the activity of the protein.

These and other objects of the present invention will be better understood by reference to the following Drawings and the Detailed Description of the Invention.

BRIEF DESCRIPTION OF THE DRAWINGS

FIGS. 1A–C. FIN13 cDNA sequence and putative protein translation.

FIG. 2. Schematic representation of FIN13 domains. (A) cDNA structure. (B) Protein structure.

FIG. 3. Comparison of FIN13 sequence to various serine/threonine kinases. The FIN13 sequence was compared to mouse (SEQ. ID NO: 7), rat (SEQ ID NO: 8), yeast (SEQ ID NO: 9), and leishmania (SEQ ID NO: 10) kinase proteins.

FIG. 6. Phosphatase activity and expression of FIN13 in mammalian cells. HeLa cells transfected with either pRK5 vector or pRKmyc-FIN13 (expressing myc-FIN13) and harvested 24 h later, were lysed in lysis buffer and cleared extracts (100 mg) were immunoprecipitated with either anti-myc antibodies (9E10) or anti-FIN13 antiserum (630). IPs were then divided and subjected to either Western analysis for the detection of FIN13 expression or a phosphatase assay. For the detection of FIN13 (A), ¼ of the IP was boiled in sample buffer and loaded onto a 10% polyacrylamide gel, electrophoresed and transferred to a nitrocellulose filter. Western blot analysis was performed using the 630 antiserum at 1:500 as described in Materials and Methods. For analysis of phosphatase activity (B), the ability of myc-FIN13 immunoprecipitates (⅛ of IP) to dephosphorylate $^{32}$P-labelled casein was examined in vitro in the presence of okadaic acid and $MnCl_2$ as described in Materials and Methods. Transfections: pRK5—solid squares and circles; pRKmyc-FIN13—solid diamonds and triangles. Immunoprecipitations: 9E10—solid squares and diamonds; 630—solid circles and triangles. The IP from pRKmyc-FIN13 transfected HeLa cells using the 9E10 antibody was also subjected to a phosphatase assay in the presence of 10 mM EDTA (+). (C) Protein phosphatase 2A was incubated for 2 h in the absence (–OA) or presence (+OA) of okadaic acid. Note the difference in scale of the y-axis between (B) and (C).

DETAILED DESCRIPTION OF THE INVENTION

Figure 4:
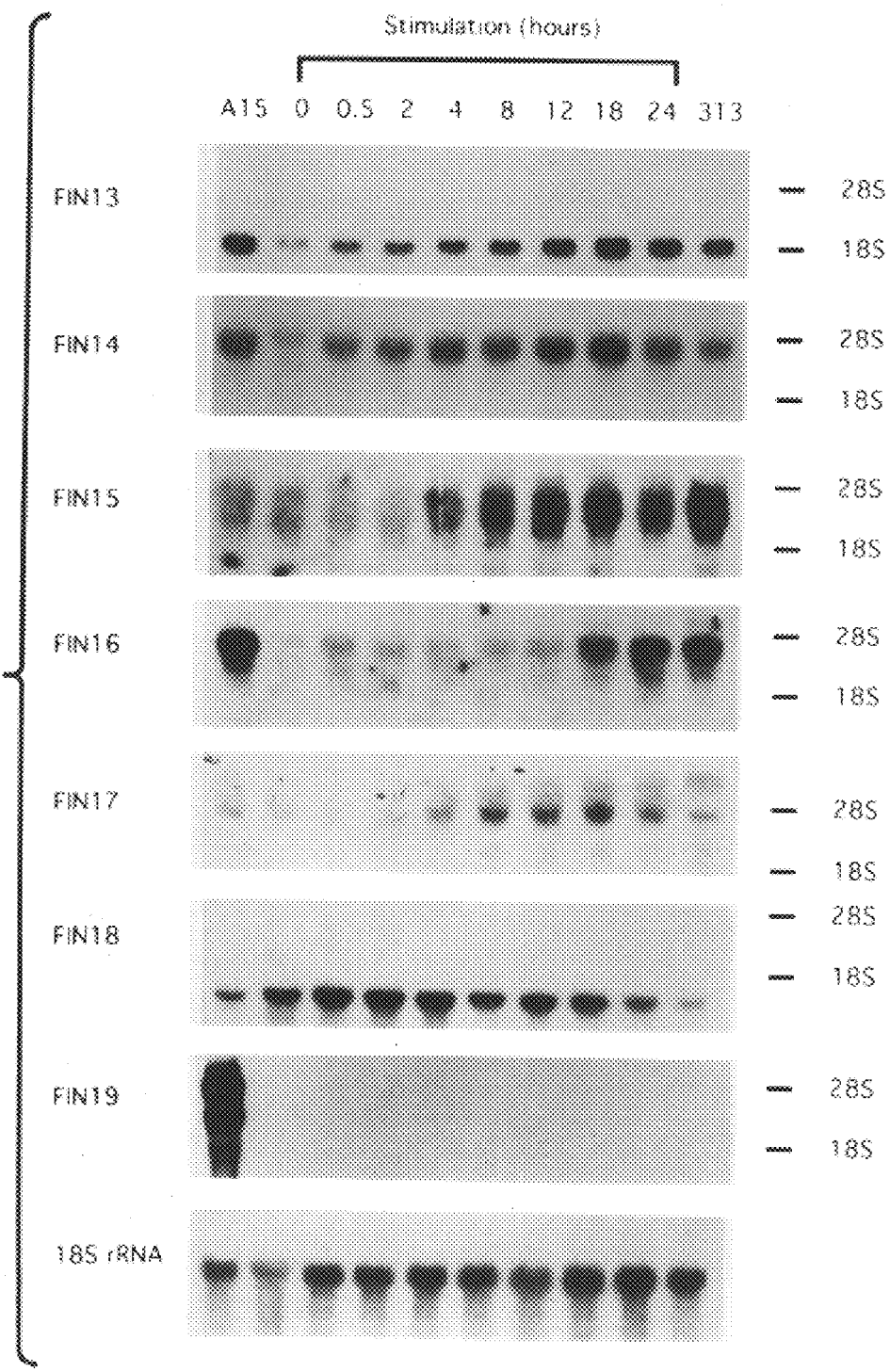
FIG. 4. Regulation of FIN13 (and other FINs) mRNA in rerponse to FGF-4. NIH 3T3 cells were starved for 48 h in DMEM/0.5% CS and stimulated for the indicated times up to 24 h with 100 ng/ml FGF-4. A15 cells and NIH 3T3 cells growing asynchronously in the presence of DMEM/10% CS are indicated as A15 and 3T3 respectively. Total RNA (6 $\mu$g) was examined by Northern analysis $^{32}$P-labelled cDNAs for the indicated FIN genes shown on the left. The position of 28S and 18s rRNA are indicated on the right.

The invention provides a novel FGF-inducible serine/threonine kinase, termed herein FIN13 (the FGF-inducible protein), including biologically active fragments thereof.

The present invention is based, in part, on the identification of genes induced by bFGF and K-FGF by subtractive hybridization (Sambrook et al., 1989, *Molecular cloning: A laboratory Manual*, 2nd ed., Cold Spring Harbor laboratory Press, pp. 10.40–10.50). Of particular importance are the genes that are directly induced by bFGF and K-FGF rather than those genes that encode factors having a general role in cell replication such as DNS synthesis. Thus, the genes induced within the first 10 hours of growth factor stimulation were examined. This analysis led to the identification of FIN13, which can be induced by using either fibroblast growth factor 4 (FGF-4) or serum to stimulate mouse cells. The sequence of the cDNA reveals a novel type 2C serine/threonine phosphatase. DNA homology with know 2C phosphatases occurs only with the catalytic domain of several type 2C phosphatases. The gene maps to the luxate locus on mouse chromosome 5. FIN13 expressed as a fusion protein in bacteria demonstrated activity of type 2C but not of type 2A or 2B phosphatases.

FIN13 expression occurs in mouse embryos. FIN13 mRNA is also expressed in adult mouse testis, to a much lesser extent in ovary, kidney, uterus of a pregnant mouse, and placenta and only minutely in other tissues. Treatment with DES increases expression of fin13 mRNA in ovaries. FIN13 is also expressed in three murine tumors and a murine carcinoma cell line. FIN13 appears to localize to germ cells in testis, indicating a role in cell proliferation/differentiation. FIN13 may function as a negative growth regulator as overexpression correlates with decreased growth of cells and stably transfected cells that overexpress have not been obtainable. FIN13 also negatively affects cellular transformation although this appears transient.

For purposes of the present description, the term "isolated" means at the least removed from a natural cellular location. Preferably, FIN13 is purified, so that it comprises at least 50%, preferably at least 75%, and more preferably at least 90% of protein (in the case of a nucleic acid, of nucleic acids) in a sample.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

In a specific embodiment, the term about means within about 20%, preferably within about 10%, and more preferably within about 5%, of the value modified.

FIN13 Serine/Threonine Phosphatase

According to the invention, the novel serine/threonine phosphatase of the invention comprises an N-terminal collagen-homology domain of about 100 amino acid residues, an acidic box domain characteristic of transcription activators having about 60 amino acid residues, a catalytically active phosphatase domain of about 180 amino acid residues similar to type 2C phosphatases, and a highly charged domain characteristic of a nuclear localization sequence. These domains may be linked by stretches of from 5 to 40 amino acid residues. Although in a specific embodiment, the FIN13 protein is a murine FIN13 protein, the present invention contemplates any animal FIN13, preferably mammalian or avian, and most preferably human. A FIN13 from any other species can be recognized by homology with the murine FIN13 exemplified herein, and particularly by the presence of the series of domains identified for FIN13 that clearly distinguish this protein from any other 2C phosphatase. In a specific embodiment, FIN13 has the domain structure shown in FIG. 2B. In a more specific embodiment, FIN13 has the amino acid sequence depicted in FIG. 1 (SEQ ID NO:2).

The term "collagen-homology" domain is used herein to refer to the fragment of FIN13 that exhibits weak sequence similarity to a range of collagens. The collagen-homology domain of FIN13 is unique: no other type 2C serine/threonine phosphatases are known to contain such a domain. Thus, the collagen-homology domain is believed to contribute to the functional specificity, i.e., regulatory specificity, of FIN13.

The term "acidic box" domain is used herein to refer to the fragment of FIN13 that comprises a high density of aspartic acid and glutamic acid residues. Such domains are found on transcription factors, such as UBF-1. Although the acidic box of FIN13 may share some sequence similarity with acidic boxes from transcription factors, it is the presence of a high density of acidic amino acid residues regardless of the specific sequences that confers protein functionability. Like the collagen-homology domain, the acidic box domain is believed to contribute to the functional specificity of FIN13.

The term "serine/threonine phosphatase" domain is used herein to refer to the fragment of FIN13 that is homologous to type 2C serine/threonine catalytic domains from other species and murine proteins. The level of sequence identity of the catalytic domain is discussed above, and in the Examples, infra. It bears noting that while the FIN13 phosphatase catalytic domain of the invention shares 35% sequence identity with another murine type 2C phosphatase, murine PP2C1 phosphatase, there is about 60% sequence similarity (which accounts for conservative amino acid substitutions) between these proteins.

Accordingly, in addition to the full length FIN13 as described above, the present invention provides FIN13 fragments comprising one or more of the structural domains: the collagen-homology domain, the acidic box domain, and the catalytic domain. Thus, the present invention provides a collagen-homology domain of FIN13, an acidic domain of FIN13, and a catalytic domain of FIN13. Indeed, in a specific embodiment illfra, the inventors have expressed a recombinant phosphatase catalytic domain fragment of FIN13. This fragment is functionally active, i.e., it catalyzes dephosphorylation. In addition, recombinant proteins consisting of the collagen-homology domain and the acidic box domain, the collagen-homology domain and the catalytic domain, and the acidic box domain and the catalytic domain are contemplated by the present invention.

Both the collagen-homology domain and the acidic box domain, whether obtained as separate FIN13 fragments or as a FIN13 fragment comprising both domains, are of significant interest in modulating the activity of endogenous FIN13, e.g., by agonizing or antagonizing the activity of FIN13. Since these fragments, either separately or together, are likely to confer much of the functional specificity of FIN13, a polypeptide consisting of one or both of these domains would be expected to modulate FIN13 activity. In one embodiment, the fragment might bind to a FIN13 target, thus competitively inhibiting endogenous FIN13 catalytic activity. In another embodiment, a polypeptide comprising the collagen-homology domain or the acidic box domain, or both, can be used to identify the presence of a target of endogenous FIN13, e.g., as may be demonstrated in a binding assay.

Similarly, a construct comprising either the collagen-binding domain or the acidic box domain and the catalytic domain may be used to increase or decrease the catalytic activity of endogenous FIN13. For example, by providing for unregulated targeting of the FIN13 catalytic domain, such a construct could increase FIN13-mediated control of cellular proliferation.

In addition to the FIN13 protein and polypeptide fragments, the invention contemplates chimeric proteins with FIN13 or a fragment thereof. An FIN13 fusion protein comprises at least a functionally active portion of a non-FIN13 protein (termed herein the "fusion partner") joined via a peptide bond to at least a functionally active portion of an FIN13 polypeptide. The non-FIN13 sequences can be amino- or carboxyl-terminal to the FIN13 sequences. In specific embodiments, infra, FIN13 and the catalytic domain polypeptide fragment of FIN13 are expressed as fusion proteins, in which the fusion partner is maltose binding protein or poly-histidine. However, the present invention contemplates fusion to any protein (or polypeptide), including marker proteins such as lacZ, signal peptides for extracellular or periplasmic expression, and different nuclear localization peptides, to mention but a few possibilities. The invention further contemplates joining FIN13, or a polypeptide fragment domain thereof, with a different protein to create a hybrid fusion protein having different target specificity, particularly targeting for intracellular translocation, catalytic activity, or other combinations of properties from the FIN13 or fragment of the invention with the fusion partner. A recombinant DNA molecule encoding such a fusion protein comprises a sequence encoding at least a functionally active portion of a non-FIN13 protein joined in-frame to the FIN13 coding sequence, and preferably encodes a cleavage site for a specific protease, e.g., thrombin or Factor Xa, preferably at the FIN13-non-FIN13 juncture. In a specific embodiment, the fusion protein is expressed in *Escherichia coli*.

Genes Encoding FIN13 Proteins

The present invention contemplates isolation of a gene encoding a FIN13 protein of the invention, including a full length, or naturally occurring form of FIN13, and any antigenic fragments thereof from any animal, particularly mammalian or avian, and more particularly human, source. As used herein, the term "gene" refers to an assembly of nucleotides that encode a polypeptide, and includes cDNA and genomic DNA nucleic acids.

Thus, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication, i.e., capable of replication under its own control.

A cell has been "transfected" by exogenous or heterologous DNA when such DNA has been introduced inside the cell. A cell has been "transformed" by exogenous or heterologous DNA when the transfected DNA expresses mRNA, which preferably is translated into a protein. Usually, expression of such a protein effects a phenotypic or functional change in the cell. However, the protein may be expressed without significantly effecting the cell, e.g., in the instance of fermentation of transformed cells for production of a recombinant polypeptide. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA, and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1%

SDS, 0.25% milk, and no formamide; or 30% formamide, 5× SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; more preferably at least about 15 nucleotides; most preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

As used herein, the term "oligonucleotide" refers to a nucleic acid, generally of at least 18 nucleotides, that is hybridizable to a genomic DNA molecule, a cDNA molecule, or an mRNA molecule encoding fin13. Oligonucleotides can be labeled, e.g., with $^{32}P$-nucleotides or nucleotides to which a label, such as biotin, has been covalently conjugated (see the discussion, supra, with respect to labeling polypeptides). In one embodiment, a labeled oligonucleotide can be used as a probe to detect the presence of a nucleic acid encoding FIN13. In another embodiment, oligonucleotides (one or both of which may be labeled) can be used as PCR primers, either for cloning full length or a fragment of fin13, or to detect the presence of nucleic acids encoding fin13. In a further embodiment, an oligonucleotide of the invention can form a triple helix with a fin13 DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of", "operably associated with", or "operatively associated with" transcriptional and translational (i.e.expression) control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7. Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding FIN13, whether genomic DNA or cDNA, can be isolated from any source, particularly from a human cDNA or genomic library. Methods for obtaining FIN13 gene are well known in the art, as described above (see, e.g., Sambrook et al., 1989, supra).

Accordingly, any animal cell potentially can serve as the nucleic acid source for the molecular cloning of a fin13 gene. The DNA may be obtained by standard procedures known in the art from cloned DNA (e.g., a DNA "library"), and preferably is obtained from a cDNA library prepared from tissues with high level expression of the protein (e.g., a cDNA library derived from bFGF, K-FGF, or FGF-4 stimulated cells, since these are the cells that evidence highest levels of expression of FIN13), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired fin13 gene may be accomplished in a number of ways. For example, if an amount of a portion of a fin13 gene or its specific RNA, or a fragment thereof, is available and can be purified and labeled, the generated DNA fragments may be screened by nucleic acid hybridization to the labeled probe (Benton and Davis, 1977, *Science* 196:180; Grunstein and Hogness, 1975, *Proc. Natl. Acad. Sci. U.S.A.* 72:3961). For example, a set of oligonucleotides corresponding to the cDNA for the FIN13 protein can be prepared and used as probes for DNA encoding FIN13, as was done in a specific example, infra, or as primers for cDNA or mRNA (e.g., in combination with a poly-T primer for RT-PCR). Preferably, a fragment is selected that is highly unique to FIN13 of the invention. Those DNA fragments with substantial sequence similarity to the probe will hybridize. As noted above, the greater the degree of sequence similarity, the more stringent hybridization conditions can be used. In a specific embodiment, low stringency hybridization conditions (50° C., 50% formamide, 5× SSC, 5× Denhardts solution) can be used to identify a homologous fin13 gene, preferably a human fin15 gene, using a murine FIN13 cDNA probe.

Further selection can be carried out on the basis of the properties of the gene, e.g., if the gene encodes a protein product having the isoelectric, electrophoretic, amino acid composition, uniquely characteristic set of structural domains, or partial amino acid sequence of FIN13 protein as disclosed herein. Thus, the presence of the gene may be detected by assays based on the physical, chemical, or immunological properties of its expressed product. For example, the rabbit polyclonal antibody to murine FIN13, described in detail infra, may be used to confirm expression of FIN13. In another aspect, a protein that has an apparent molecular weight of 60 or 70 kDa, and which is biochemically determined to have a highly acidic region and serine/threonine phosphatase activity, is a good candidate for FIN13.

The present invention also relates to cloning vectors containing genes encoding fragments consisting of the specific FIN13 domains describe above, analogs, and derivatives of FIN13 of the invention, that have the same or homologous functional activity as FIN13, and homologs thereof from other species. The production and use of derivatives and analogs related to FIN13 are within the scope of the present invention. For example, a fragment corresponding to the catalytic domain exhibits enzymatic activity. In a specific embodiment, the derivative or analog is functionally active, i.e., capable of exhibiting one or more functional activities associated with a full-length, wild-type FIN13 of the invention. In another embodiment, FIN13 containing a different putative nuclear targeting peptide can be used to modulate the activity of FIN13. In another aspect, a FIN13 protein of the invention can be prepared by substituting a catalytic domain from another protein, such as murine PP2C1 protein, for that found in FIN13.

FIN13 derivatives can be made by altering encoding nucleic acid sequences by substitutions, additions or deletions that provide for functionally equivalent molecules. Preferably, derivatives are made that have enhanced or increased functional activity relative to native FIN13.

Due to the degeneracy of nucleotide coding sequences, other DNA sequences which encode substantially the same amino acid sequence as a fin13 gene may be used in the practice of the present invention. These include but are not limited to allelic genes, homologous genes from other species, and nucleotide sequences comprising all or portions of fin13 genes which are altered by the substitution of different codons that encode the same amino acid residue within the sequence, thus producing a silent change. Likewise, the FIN13 derivatives of the invention include, but are not limited to, those containing, as a primary amino acid sequence, all or part of the amino acid sequence of a FIN13 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Substitutions of glu for asp and visa versa, or "switching" acid amino acid residues with other residues, while retaining the total number of acidic residues in the acidic domain, are expected to retain the functional activity of that domain.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding FIN13 derivatives and analogs of the invention can be produced by various methods known in the art. The manipulations which result in their production can occur at the gene or protein level. For example, the cloned FIN13 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of FIN13, care should be taken to ensure that the modified gene remains within the same translational reading frame as the FIN13 gene, uninterrupted by translational stop signals, in the gene region where the desired activity is encoded.

Additionally, the FIN13-encoding nucleic acid sequence can be mutated in vitro or in viva, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated FIN13 gene product. Any technique for mutagenesis known in the art can be used, including but not limited to, in vitro site-directed mutagenesis (Hutchinson, C., et al., 1978, *J. Biol. Chem.* 253:6551; Zoller and Smith, 1984, *DNA* 3:479–488; Oliphant et al., 1986, *Gene* 44:177; Hutchinson et al., 1986, *Proc. Natl. Acad. Sci. U.S.A.* 83:710), use of TAB® linkers (Pharmacia), etc. PCR techniques are preferred for site directed mutagenesis (see Higuchi, 1989, "Using PCR to Engineer DNA", in PCR *Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2 μ plasmid.

The present invention extends to the preparation of antisense nucleotides, including ribozymes, that may be used to detect the presence of mRNA coding for FIN13 or interfere with the expression of FIN13 at the translational level. This approach utilizes antisense nucleic acid and ribozymes to hybridize to fin13 mRNA, which can block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (see Marcus-Sekura, 1988, *Anal. Biochem.* 172:298). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro (Marcus-Sekura, 1988, supra; Hambor et al., 1988, *J. Exp. Med.* 168:1237). Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988, *J. Am. Med. Assoc.* 260:3030). Because they are sequence-specific, only mRNAs with particular sequences are inactivated.

Investigators have identified two types of ribozymes, Tetrahymena-type and "hammerhead"-type (Hasselhoff and Gerlach, 1988). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding FIN13 described and enabled herein may thus be used to prepare antisense molecules that hybrizize to and ribozymes that cleave mRNAs for FIN13, thus inhibiting expression of the gene encoding FIN13, which may alter the control of proliferation of cells, possibly resulting in greater cellular proliferation.

Expression of FIN13 Proteins

The nucleotide sequence coding for FIN13, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding FIN13 of the invention is operably associated with a promoter in an expression vector of the invention. Both cDNA and genomic sequences can be cloned and expressed under control of such regulatory sequences. An expression vector also preferably includes a replication origin, unless the vector is intended for homologous recombination.

The necessary transcriptional and translational signals can be provided on a recombinant expression vector, or they may be supplied by the native gene encoding FIN13 and/or its flanking regions.

As pointed out above, potential chimeric partners for FIN13 include substitute catalytic domains, or a different nuclear targeting domain.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant FIN13 protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding FIN13 is cultured in an appropriate cell culture medium under conditions that provide for expression of FIN13 by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of FIN13 protein may be controlled by any promoter/enhancer element known in the art, but these regulatory elements must be functional in the host selected for expression. Promoters which may be used to control FIN13 gene expression include, but are not limited to, the SV40 early promoter region (Benoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. U.S.A.* 78:1441–1445), the regulatory sequences of the metallothionein gene (Brinster et al., 1982, *Nature* 296:39–42); prokaryotic expression vectors such as the β-lactamase promoter (Villa-Kamaroff, et al., 1978, *Proc. Natl. Acad. Sci. U.S.A.* 75:3727–3731), or the tac promoter (DeBoer, et al., 1983, *Proc. Natl. Acad. Sci. U.S.A.* 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58), alpha 1-antitrypsin gene control region which is active in the liver (Kelsey et al., 1987, *Genes and Devel.* 1:161–171), beta-globin gene control region which is active in myeloid cells (Mogram et al., 1985, *Nature* 315:338–340; Kollias et al., 1986, *Cell* 46:89–94), myelin basic protein gene control region which is active in oligodendrocyte cells in the brain (Readhead et al., 1987, *Cell* 48:703–712), myosin light chain-2 gene control region which is active in skeletal muscle (Sani, 1985, *Nature* 314:283–286), and gonadotropic releasing hormone gene control region which is active in the hypothalamus (Mason et al., 1986, *Science* 234:1372–1378).

Expression vectors containing a nucleic acid encoding a FIN13 of the invention can be identified by four general approaches: (a) PCR amplification of the desired plasmid DNA or specific mRNA, (b) nucleic acid hybridization, (c) presence or absence of selection marker gene functions, (d) analysis with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding FIN13 is inserted within the "selection marker" gene sequence of the vector, recombinants containing the FIN13 insert can be identified by the absence of the FIN13 gene function. In the fourth approach, recombinant expression vectors can be identified by digestion with appropriate restriction enzymes, followed by molecular weight analysis of resulting digestion products (fragments). In the fifth approach, recombinant expression vectors can be identified by assaying for the functional, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., 1988, *Gene* 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufinan, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. Expression in yeast can produce a glycosylated product. Expression in eukaryotic cells can increase the likelihood of "native" folding of a heterologous protein. Moreover, expression in mammalian cells can provide a tool for reconstituting, or constituting, FIN13 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun (biolistics), or a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990).

Antibodies to FIN13

According to the invention, FIN13 protein produced recombinantly or by chemical synthesis, and fragments or other derivatives or analogs thereof, including fusion proteins, may be used as an immunogen to generate antibodies that recognize the FIN13 protein. Such antibodies are referred to a specific for FIN13, or characterized by specific binding to FIN13. Such antibodies include but are not limited to polyclonal, monoclonal, chimeric, single chain, Fab fragments, and an Fab expression library. In specific embodiments, infra, a FIN13-poly-histidine fusion protein, and a FIN13-maltose binding protein (MBP) fusion protein were used as antigens. The anti-FIN13 antibodies of the invention may be cross reactive, e.g., they may recognize FIN13 from different species. Polyclonal antibodies have greater likelihood of cross reactivity. Alternatively, an antibody of the invention may be specific for a single form of FIN13, such as murine FIN13. Preferably, such an antibody is specific for human FIN13.

Various procedures known in the art may be used for the production of polyclonal antibodies to FIN13 protein a recombinant FIN13 or derivative or analog thereof. For the production of antibody, various host animals can be immunized by injection with the FIN13 protein, or a derivative (e.g., fragment or fusion protein) thereof, including but not limited to rabbits, mice, rats, sheep, goats, etc. In one embodiment, the FIN13 protein, or more preferably a fragment thereof, can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum.

For preparation of monoclonal antibodies directed toward the FIN13 protein, or fragment, analog, or derivative thereof, any technique that provides for the production of antibody molecules by continuous cell lines in culture may be used. These include but are not limited to the hybridoma technique originally developed by Kohler and Milstein (1975, *Nature* 256:495–497), as well as the trioma technique, the human B-cell hybridoma technique (Kozbor et al., 1983, *Immunology Today* 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.* 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, *J. Bacteriol.* 159–870; Neuberger et al., 1984, *Nature* 312:604–608; Takeda et al., 1985, *Nature* 314:452–454) by splicing the genes from a mouse antibody molecule specific for a FIN13 protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce FIN13 protein-specific single chain antibodies. An additional embodiment of the invention utilizes the techniques described for the construction of Fab expression libraries (Huse et al., 1989, *Science* 246:1275–1281) to allow rapid and easy identification of monoclonal Fab fragments with the desired specificity for a FIN13 protein, or its derivatives, or analogs. Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a FIN13 protein, one may assay generated hybridomas for a product which binds to a FIN13 protein fragment containing such epitope. For selection of an antibody specific to a FIN13 protein from a particular species of animal, one can select on the basis of positive binding with FIN13 protein expressed by or isolated from cells of that species of animal.

According to the invention, the antibodies specific for FIN13 can be labeled. Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotonmetric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Other labels for use in the invention include magnetic beads or magnetic resonance imaging labels.

In another embodiment, a phorphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthphosphate. In addition to metabolic (or biosynthetic) labeling with $[^{35}S]$-methionine, the invention further contemplates labeling with $[^{14}C]$-amino acids and $[^3H]$-amino acids (with the tritium substituted at non-labile positions).

The foregoing antibodies can be used in methods known in the art relating to the localization and activity of the FIN13 protein, e.g., for Western blotting, imaging FIN13 protein in situ, measuring levels thereof in appropriate physiological samples, immunohistochemistry, etc.

In a specific embodiment, antibodies that agonize or antagonize the activity of FIN13 protein can be generated.

Detection of FIN13 and Implications Thereof

According to the invention, the presence or amount of FIN13 may be a useful indicator of cellular activation, particularly cellular growth. Accordingly, the present invention provides for establishing cellular growth by detecting the presence or measuring the amount of FIN13 protein or mRNA in sample. The diagnostic methods can be used to detect a fin13 gene or mRNA, or FIN13 protein, in a biological sample from an individual. The biological sample can be a biological fluid comprising cells, such as but not limited to, blood, interstitial fluid, plural effusions, urine, cerebrospinal fluid, and the like. Preferably, FIN13 is detected in blood, which is readily obtained. Alternatively, FIN13 can be detected from cellular sources, such as, but not limited to, tissue biopsies, adipocytes, testes, heart, and the like. For example, cells can be obtained from an individual by biopsy and lysed, e.g., by freeze-thaw cycling, or treatment with a mild cytolytic detergent such as, but not limited to, TRITON X-100®, digitonin, NONIDET P (NP)-40®, saponin, and the like, or combinations thereof (see, e.g., International Patent Publication WO 92/08981, published May 29, 1992). In yet another embodiment, samples containing both cells and body fluids can be used (see ibid.).

In another embodiment, a lower level or lack of FIN13 expression in a sample proliferating cell compared to a normal proliferating cell may be indicative of uncontrolled cell growth of the sample cell. Thus, the invention contemplates a method for detecting uncontrolled proliferation in a sample cell comprising detecting the level of mammalian FIN13 in a cell undergoing increased cell growth, and comparing the level of FIN13 detected with the level in a normal cell undergoing cell growth, wherein a lower level of FIN13 in the sample cell than in the normal cell indicates uncontrolled proliferation. The level of FIN13 can be detected by detecting mRNA or FIN13 protein, the latter by immunoassay or biochemistry, as described infra. Detection of decreased FN13 expression in a proliferating cell may indicate tumorigenesis or lysplasia.

The present invention includes an assay system which may be prepared in the form of a test kit for the quantitative analysis of the extent of the presence of the FIN13, or to identify drugs or other agents that may mimic or block their activity. The system or test kit may comprise a labeled component, such as an antibody or oligonucleotide specific for FIN13 protein or mRNA, respectively. Preferably, an assay kit of the invention also comprises a positive control reagent, either FIN13 protein or fin13 mRNA, for confirming assay performance, and, if desired, for quantitation.

In one embodiment, the present invention provides for the detection of expression of FIN13 or mRNA encoding FIN13. For example, an antisense oligonucleotide of the invention can be used in standard Northern hybridization analysis to detect the presence, and in some instances quantitate the level of expression, of FIN13 mRNA. An oligonucleotide of the invention may also be used to detect mutations in the FIN13 mRNA or gene, by high stringency hybridization analysis with a mutant specific probe (or a wild-type specific probe) with detection of hybridization or lack thereof indicating whether the gene is mutated. For example, hybridization of a wild-type specific probe indicates no mutation, and lack of hybridiation indicates a mutation. The reverse would be true for a mutation-specific probe. The techniques for preparing labeled oligonucleotides and using them to analyze gene expression or mutations are well known in the art.

Alternatively, oligonucleotides of the invention can be used as PCR primers to amplify FIN13 mRNA (e.g., by reverse transcriptase-PCR), or FIN13 genes. The amplified mRNA can be quantified, or either amplified mRNA or genomic DNA can be analyzed for mutations. Mutations in the amplified DNA can be detected by creation or deletion of restriction fragment length polymorphisms (RFLPs) not found in the native gene or cDNA, hybridization with a mutation specific probe (or lack of hybridization with a wild-type specific probe), as well as by other techniques.

In yet another embodiment, deletion or translocation of the fin13 gene in tumor cells would indicate a role of FIN13 in tumor suppression. Thus, deletion or translocation of fin13 would be indicative of a tumor.

Identification of such mutations may provide a molecular explanation for uncontrolled proliferation, as well as indicate that the cell has been transformed, e.g., into a tumor cell.

The presence or level of FIN13 protein can be measured using by immunoassay using an antibody of the invention. Various immunoassay techniques are known in the art, e.g., as described in the "Antibody" section above. In a specific embodiment, infra, a rabbit polyclonal antiserum detects FIN13. In an immunoassay, an antibody may be introduced into a biological sample. After the antibody has had an opportunity to react with sites within the sample, the resulting product mass may be examined by known techniques, which may vary, e.g., with the nature of the label attached.

Finally, biochemical or immunochemical/biochemical (e.g., immunoprecipitation) techniques can be used to detect the presence and or level of FIN13. For example, in one embodiment, a cell may be metabolically labeled (as described in the "Antibody" section, supra, and the Examples, infra), the cell lysed and analyzed by PAGE, and the presence of a 60 kDA or 70 kDa band, or both, evaluated. Furthermore, the band can be quantitated by densitometry. Alternatives to metabolic labeling include Western analysis, silver staining, Coomassie blue staining, etc. In another embodiment, the presence and level of FIN13 activity can be detected enzymatically, e.g., by testing the catalytic activity of a cellular extract or isolated protein corresponding to FIN13.

Therapeutic Aspects of FIN13

Based on the data developed in the Examples, infra, particularly the observation that increased levels of expression of FIN13 are associated with inhibition of cell growth, FIN13 may be employed as a growth regulatory factor, and more preferably, as a tumor suppressor. Thus, according to the invention, FIN13, or an expression vector encoding FIN13, can be administered to a subject in need of treatment for uncontrolled cellular proliferation in order to agonize FIN13 activity to regulate and inhibit the proliferation. Alternatively, where an increase in cell growth is desired, e.g., in immune cells of an immunocompromised individual or a subject undergoing bone marrow transplantation, an antagonist of FIN13 (such as an antisense nucleic acid or a ribozyme) may be desired to antagonize FIN13 activity. The methods of administration described herein can be employed to agonize or antagonize FIN13 activity.

Accordingly, in one aspect the present invention is directed to the treatment of tumors, particularly solid tumors, by increasing FIN13 activity in tumor cells to control cellular proliferation and tumor growth. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment, dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine*, 2d Ed., J. B. Lippincott Co., Philadelphia.

The present invention is also directed to treatment of non-malignant tumors and other disorders involving inappropriate cell or tissue growth by administering a therapeutically effective amount of FIN13 of the invention. The invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also contemplated.

In yet another embodiment, the present invention is directed to transient inhibition of germ cell proliferation for contraception. For example, by increasing the level of FIN13 in dividing cells in testes, sperm production can be decreased and the male rendered temporarily infertile. This infertility may be reversed by terminating the FIN13 treatment.

Various mechanisms are available for increasing FIN13 activity in cells, e.g., direct administration of a construct (chimeric or via chemical derivitization or crosslinking) of FIN13 with a targeting molecule (e.g., transferrin, a hormone, a growth factor, or a target cell-specific antibody) to a subject in need of treatment, or by gene therapy approaches to increase expression of FIN13 in proliferating cells in situ.

A subject in whom administration of FIN13 is an effective therapeutic regiment for an dysproliferative disease is preferably a human, but can be any animal. Thus, as can be readily appreciated by one of ordinary skill in the art, the methods and pharmaceutical compositions of the present invention are particularly suited to administration to any animal, particularly a mammal, including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Preferably, a composition of the invention for treatment of a dysproliferative disease or disorder is provided in a pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state goverment or listed in the U.S. Pharmacopeia or other generally recognized pharmacopela for use in animals, and more particularly in humans, although a pharmaceutically acceptable carrier of the invention may share the attributes of such an approved carrier without itself having been approved. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. According to the invention, where regulation of cellular proliferation is desired, a therapeutically effective amount of a pharmaceutical composition of the invention will reduce the rate of cell growth or tissue, including tumor, growth. A therapeutically effective amount and treatment regimen can be developed for an individual by an ordinary skilled physician, taking into account the age, sex, size, and physical well being of the patient; the course and extent of the disease or disorder; previous, concurrent, or subsequent treatment regimens and the potential for drug interactions; all of which parameters are routinely considered by a physician in prescribing administration of a pharmaceutical agent.

The instant invention provides for conjugating targeting molecules to FIN13, DNA vectors (including viruses) encoding FIN13, and carriers (i.e., liposomes) for targeting to a desired cell or tissue, e.g., a tumor. "Targeting molecule" as used herein shall mean a molecule which, when administered in vivo, localizes to desired location(s).

In various embodiments, the targeting molecule can be a peptide or protein, antibody, lectin, carbohydrate, or steroid. In one embodiment, the targeting molecule is a protein or peptide ligand of an internalized receptor on the target cell. In a specific embodiment, the targeting molecule is a peptide comprising the well known RGD sequence, or variants thereof that bind RGD receptors on the surface of cells such as cancer cells, e.g., human ova that have receptors that recognize the RGD sequence. Other ligands include, but are not limited to, transferrin, insulin, amylin, and the like. Receptor internalization is preferred to facilitate intracellular delivery of FIN13 protein.

In another embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the FIN13 via the reduced sulfhydryl.

Antibodies for use as targeting molecule are specific for cell surface antigen. In one embodiment, the antigen is a receptor. For example, an antibody specific for a receptor on cancer cells, such as melanoma cells, can be used.

This invention further provides for the use of other targeting molecules, such as lectins, carbohydrates, proteins and steroids.

Administration of Targeted FIN13

According to the invention, a therapeutic composition comprising delivery of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of FIN13 is indicated to inhibit or regulate growth of a tumor, it may be introduced by injection into the tumor or into tissues surrounding the tumor.

In another embodiment, the therapeutic compound can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid). To reduce its systemic side effects and increase cellular penetration, this may be a preferred method for introducing FIN13.

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. *Ref. Bioined. Eng.* 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., a tumor, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of a tumor.

Other controlled release systems are discussed in the review by Langer (Science 249:1527–1533 (1990)).

Gene Therapy

In one embodiment, a gene encoding an FIN13 protein or polypeptide domain fragment thereof is introduced in vivo or ex vivo in a nucleic acid vector.

Viral vectors commonly used for in vivo or ex vivo targeting and therapy procedures are DNA-based vectors and retroviral vectors. Methods for constructing and using viral vectors are known in the art (see, e.g., Miller and Rosman, *Bio Techniques* 7:980–990 (1992)). DNA vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, tumor tissue can be specifically targeted. Examples of particular vectors include, but are not limited to, a defective herpes virus 1 (HSV1) vector (Kaplitt et al., 1991, *Molec. Cell. Neurosci.* 2:320–330), an attenuated adenovirus vector, such as the vector described by Stratford-Perricaudet et al. (1992, *J. Clin. Invest.* 90:626–630), and a defective adeno-associated virus vector (Samulski et al., 1987, *J. Virol.* 61:3096–3101; Samulski et al., 1989, *J. Virol.* 63:3822–3828).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, *Nature Medicine* (1995)). In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; International Patent Publication No. WO 95/07358, published Mar. 16, 1995, by Dougherty et al.; and Kuo et al., 1993, *Blood* 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al., 1987, *Proc. Natl. Acad. Sci. U.S.A.* 84:7413–7417; see Mackey, et al., 1988, *Proc. Natl. Acad. Sci. U.S.A.* 85:8027–8031)). The use of cationic lipids may promote encapsulation of negatively charged nucleic acids, and also promote fusion with negatively charged cell membranes (Feigner and Ringold, 1989, *Science* 337:387–388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in viva as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, biolostics (use of a gene gun), or use of a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990).

The present invention may be better understood by reference to the following Examples, which are provided by way of exemplification and are in no way limiting.

EXAMPLE 1

ISOLATION OF A NOVEL FGF-INDUCIBLE GENE

This Example describes isolation of a number of cDNAs, the expression of whose corresponding RNAs is induced by FGF-4 (K-FGF) in murine NIH 3T3 fibroblasts. The cDNAs (FIN, for FGF-inducible) were isolated using a strategy of subtractive hybridization designed to yield "late" genes which compared transformed 3T3 cells that constitutively produce FGF-4 with their normal counterpart. The 21 independent cDNAs isolated were found to correspond to known genes (FIN1–12), or novel genes (FIN13–21). Expression of the FIN genes is induced in response to FGF-4 as well as to serum in NIH 3T3 cells with delayed kinetics, with maximum stimulation occurring 12–18 h after growth factor treatment. Induction requires protein synthesis and is mostly transcriptional. FIN1–12 encode a broad range of previously described genes, some of which are proposed to have an important role in cell proliferation. The novel clones include a serine-threonine phosphatase (FIN13). The distribution of expression of the novel FIN clones in adult mouse tissues was highly restricted, although most were expressed in embryos. While expression of novel FIN cDNAs was strongly regulated in NIH 3T3 cells, induction of differentiation in PC-12 cells by FGF-4 (as well as NGF) did not result in significant induction of expression, suggesting that most of the FIN genes are proliferation-specific. Chromosomal localization of novel FIN clones indicated that each segregated independently to separate mouse chromosomes.

Materials and Methods

Cell culture. Mouse NIH 3T3 cells and A15 cells were cultured in Dulbecco's modified Eagle's medium (DMEM) containing 10% calf serum (CS). A15 cells are a NIH 3T3 cell line transformed with a human genomic fragment of the FGF-4 gene and have been previously described (Delli Bovi and Basilico, 1987, *Proc. Natl. Acad. Sci. USA* 84:5660). Rat pheochromocytoma PC12 cells were cultured in DMEM containing 10% heat inactivated horse serum (HS) (Gemini Bioproducts), 5% fetal bovine serum (FBS) (Gemini Bioproducts). For stimulation with growth factors, NIH 3T3 cells were grown to 60–80% confluence, starved for 48 h in DMEM containing 0.5% CS and then stimulated with 50 ng/ml recombinant human FGF-4 or 10% CS for up to 24 h. Where indicated 10 µg/ml cycloheximide was added simultaneously with the growth factor. PC12 cells were starved for 48 h in DMEM containing 4.9 g/l glucose, 0.1% HS and 5% FBS for up to 24 h. For FGF-4 or NGF stimulations, medium was changed and fresh growth factor added 48 h after the initial growth factor stimulation. Greater than 90% of PC12 cells had differentiated after 96 h or FGF-4 or NGF treatment as determined by the induction of neurite-like processes. FGF-4 induced shorter and less abundant processes compared to NGF.

RNA isolation. Total RNA was harvested from guanidine isothiocyanate (GIT) lysed cultured cells by centrifugation through a cushion of $CsCl_2$ using standard procedures (Chirgwin et al., 1979, Biochem. J., 18:5294–5299). RNA was isolated from mouse tissues and embryos by first extraction in phenol/chloroform (P/C) and then chloroform prior to centrifugation through $CsCl_2$. Poly A+ RNA was enriched by twice selection on an oligo (DT)-cellulose (Sigma) column.

cDNA library preparation. A cDNA library was made from the FGF-4 transformed A15 cell line in lambda Zap II (Stratagene) essentially as described in the suppliers' instructions except that, (1) 600 U of M-MLV Superscript II RNAse H– reverse transcriptase (RT) (Gibco-BRL) was used to reverse transcribe 5 µg Poly A+ RNA; (2) second strand synthesis was achieved using 67 U DNA polymerase I, 4 U RNAse H with the addition of 20 U E. coli DNA ligase and 150 µM β-nicotinamide adenine dinucleotide; and (3) cDNAs cgreater than 400 base pairs (bp) were fractionated on a CL-4B spin column and ligated in EcoRI/XhoI digested UniZap XR for 2 days at 4° C. The ligation reaction was packaged in vitro using Gigapack II Gold packaging extracts (Stratagene) and the resulting library contained greater than $1.3 \times 10^4$ recombinants.

Biotinylation of RNA. Photobiotinylation was carried out as previously described (Sive and St. John, 1988, Nucl. Acids. Res. 16:10937) with some modifications. Briefly, heat denatured poly A+ RNA (50 µg) isolated from NIH3T3 cells growing in DMEM/10% CS was added to an equivalent amount (w/w) of photoreactive biotin (Boehringer Mannheim) and irradiated on ice for 20 min with a 275 W sunlamp. Tris-HCl (pH 7.4) and EDTA were added to 20 mM and 1 mM respectively, the RNA extracted with 2-butanol and then ethanol precipitated. The RNA was recovered by centrifugation, resuspended in $H_2O$ and irradiated in the presence of photoreactive biotin as before. Biotinylated RNA was extracted twice in 2-butanol and ethanol precipitated.

Subtractive hybridization. cDNA to be used for subtractive hybridization was made by reverse transcribing 5 µg poly (A)+ RNA from A15 cells with 600 U M-MLV Superscript RT, 5 µg oligo $dT_{17}$ primer, 0.5 mM dNTPs, 40 U RNAse block (Promega) and 1× RT buffer (50 mM Tris-HCl pH 8.3, 75 mM KCl, 3 mM $MgCl_2$ and 10 mM dithiothretiol; DTT) in a 50 µl reaction volume for 60 min. at 37° C. RNA Templates were then subjected to alkaline hydrolysis in 0.2 M NaOH at 55° C. for 20 min. Following neutralization in 0.2 Tris-HCL (pH 7.9) and 0.2 M HCl, the cDNA was ethanol precipitated. The cDNA as then pelleted and resuspended in 1× HES buffer (50 mM HEPES pH 7.5, 2 mM DTA and 0.2% sodium dodecyl sulfate; SDS) and denatured at 98° C. for 10 min. A fivefold mass excess of biotinylated RNA was denatured at 75° C. for 5 min. after which cDNA and biotinylated RNA were combined, NaCl was added to a final concentration of 0.5 M and the hybridization carried out at 66° C. to a C.t of greater than 3000 (typically 24–36 h).

The hybridization mixture was then diluted 1:2 with 1× HE buffer (50 mM HEPES pH 7.5, 2 mM EDTA) and NaCl was added to give a final concentration 0.5 M. Unhybridized cDNA was recovered by adding 10 µg streptavidin (Gibco-BRL) (Sive and St. John, 1988, supra) and incubating at ambient temperatures for 10 min. after which the mix was P/C extracted twice with the organic phase being back extracted each time with an equivolume of 1× HE buffer. The pooled aqueous phase was then ethanol precipitated. The subtracted cDNA was then recovered by centrifugation and subjected to a second round of hybridization with a five-fold mass excess of biotinylated poly (A)+ RNA followed by streptavidin/P/C treatment and ethanol precipitation as described above.

Polymerase chain reaction (PCR) amplification of subtracted cDNAs. The cDNA was denatured in the presence of 1 µg random hexamers (Boehringer Mannheim) and then made double stranded with 150 µM dNTPs, 7.5 U DNA polymerase I in 50 mM Tris-HCl pH 7.5, 10 mM $MgCl_2$, 1 mM DTT and 50 µg/ml bovine serum albumin (BSA) at 14° C. for 4 h following which the cDNA was P/C extracted and ethanol precipitated. Double stranded cDNA was recovered by centrifugation and blunted with 1.5 U T4 DNA polymerase (Boehringer Mannheim), 330 µM dNTPs in 50 mM Tris-HCl (pH 8.0), 5 mM $MgCl_2$, 5 mM DTT and 50 µg/ml BSA at 37° C. for 30 min. The blunted cDNAs were then P/C extracted and ethanol precipitated.

An adaptor was synthesized, phosphorylated, and ligated to the pool of cDNAs to serve as PCR primer annealing sites for the amplification and radiolabeling of subtracted cDNAs. Oligonucleotide AD1 (5'-GAGGAATTCTCGAGCTCTA-GAC-3') (SEQ ID NO:3) was annealed to 5'-phosphorylated AD2 (5'-GTCTAGAGCTCGAGAAT-3') (SEQ ID NO:4) which yielded an adaptor containing EcoRI, XhoI, SacI and XbaI restriction enzyme sites and one blunt/phosphorylated end.

AD2 (10 µg) was phosphorylated with 20 U T4 polynucleotide kinase and 1 mM dATP in 60 mM Tris-HCl (pH 7.4), 15 mM Bn-mercaptoethanol and 10 mM $MgCl_2$ for 1 h at 37° following which the reaction was boiled for 5 min. An equimolar amount of AD2 was added and the mix was allowed to cool to ambient temperatures in a large volume of water for 1 h. Annealed adaptor was purified on a 15% polyacrylamide gel with 1× TBE buffer (0.1 M Tris-HCl, 0.083 M boric acid, 20 mm EDTA, H 8.0) and 670 ng was ligated to the pool of subtracted cDNAs with 5 U T4 DNA ligase nd 1.5 mM dATP in 66 mM Tris-HCl (pH 7.5), 5 mM $MgCl_2$ and 1 mM DTT overnight at 4° C. cDNAs grater than 400 bp were separated form unligated adaptors by passage through a S400 Sephacryl (Promega) column.

PCR was used to amplify the subtracted cDNAs from 1 µl of the S400 eluent. The PCR contained 0.2 mM dNTPs, 1 µM primer AD1, 1.25 U Taq polymerase (Boehringer Mannheim), 1× PCR buffer (10 mM Tris-HCL pH 8.3, 50 mM KCl, 5.5 mM $MgCl_2$ and 100 µg/ml gelatine) in a 50 µl reaction volume. Amplification conditions were as follows: 98° C. for 1 min., 55° C. for 1 min., 72° C. for 5 min. for two cycles and 95° C. for 1 min., 55° C. for 1 min., 72° C. for 5 min. for 13 cycles. To favor the amplification of long cDNAs, PCR products greater than 400 bp were recovered after 15 cycles by passage through a S400 Sephacryl column and 10 µl of the eluent was subjected to a further 15 cycles amplification using the protocol above. Following a total of 30 cycles a pool of subtracted-amplified cDNAs (sacDNAs) was generated which was either used for direct cloning via the restriction enzyme sites incorporated by the PCR primers, or for synthesis of a radiolabeled probe.

A PCR-labeled probe was then generated using 5 µl of sacDNA, 0.2 mM dGTP, 0.2 mM dTTP, 1 µM primer AD1, 1.25 U Taq polymerase, 1× PCR buffer and 50 µCi each of [α-$^{32}$P]dATP and [α-$^{32}$P]dCTP (3000 Ci/mmol) (Du Pont) using 15 cycles of the program above. The PCR labeled probe was purified form unincorporated radionucleotides by passage through a G-25 Sepharose spin column.

Screening the cDNA library. Approximately $1.2 \times 10^4$ plaques from the lambda ZapII A15 cDNA library were plated at 30,000 plaques/15 cm plate. Plaques were lifted onto replica Nitrocellulose filters (Schleicher and Schuell) and fixed by u.v. crosslinking (120,000 µJ/cm$^2$ at 254 nm). Filters were then prehybridized overnight and hybridized to sacDNAs under standard conditions. Positive plaques were picked and subjected to a secondary screen using the conditions described above. Bluescript, plasmids containing cDNA inserts were excised from isolated Zap II phase after secondary screening using the suppliers' recommended protocol (Stratagene).

Reverse Northern screening of isolated clones. cDNA clones were screened by the reverse Northern procedure in which each plasmid, immobilized on a nylon filter was probed with radiolabeled cDNA from, (1) FGF-4 transformed A15 cells growing in DMEM/10% CS, (2) quiescent NIH3T3 cells and (3) NIH3T3 cells growing in DMEM/10% CS. Plasmids (1 µg and 100 ng) were denatured in 0.2 M NaOH for 10 in. at 55° C., applied to triplicate Genescreen nylon filters (Du Pont) using a slot blot apparatus and fixed by u.v. crosslinking. Each set of filters was then prehybridized overnight at 42° C. in prehybridization solution with 250 µg/ml yeast tRNA and then hybridized in the same solution with radiolabeled cDNA. Radiolabeled cDNA was made by reverse transcribing 2 µg poly (A)+ RNA from cells 1, 2, and 3 above with 600 U M-MLV Superscript RT, 2 µg oligo dT$_{17}$ primer, 0.5 mM each of dCTP, dGTP and dTTP, 0.5 mM dATP, 150 µCi [α-$^{32}$P]dATP, 40 U RNAse block in 1× RT buffer for 60 min. at 37° C. Radiolabeled cDNA was separated from unincorporated radionucleotides by passage over a G-50 Sephadex column. Each set of filers were hybridized with an equivalent amount of radiolabeled probe (10$^6$ c.p.m./ml).

Sequencing. Sequencing was performed by the dideoxynucleotide chain termination method (Sanger et al., 1977, *Proc. Natl. Acad. Sci. USA*, 74:5643–5647) using 5 µCi/reaction [α-$^{35}$S]dATP (10 mCi/ml Du Pont), Sequenase (U.S.B. Corp.) and a conventional sequencing apparatus or fluorescent labeled nucleotides, Taq polymerase and the Applied Biosystems 373 DNA sequencer. Sequences of cDNAs were obtained using three approaches. Firstly, Sau3AI fragments were subcloned into the BamHI site of Bluescript and sequence with T3 and T7 primers. Secondly overlapping sequences were generated by creating nested 5'-deletions with exonuclease III and then sequencing with the T3 primer. And thirdly, specific primers were designed for sequencing internal cDNA sequences.

Northern analysis. RNA was electrophoresed on a 1% formaldehyde agarose gel, transferred overnight in 20× SSC to Genescreen-Plus nylon filters (Du Pont) and fixed by u.v. crosslinking. Filters were prehybridized, hybridized with radiolabeled cDNA probes and washed under standard conditions. To stimulate folliculogensis, immature mice (3 weeks) were injected subcutaneously with diethylstilbesterol (DES) or vehicle essentially as described previously (Guthridge et al., *Growth Factors*, 7:15 (1992)), and RNA was prepared from ovaries four days after stimulation.

Chromosome localization. C3H/HeJ-gld and Mus spretus (Spain) mice and [(C3H/HeJ-gld x Mus spretus) F1× C3H/HeJ-gld] interspecific backcross mice were bred and maintained as previously described (Seldin et al., 1988, *J. Exp. Med.*, 167:688–693). Mus spretus was chosen as the second parent in this cross because of the relative ease of detection of informative restriction fragment length variants (RFLV) in comparison with cross using conventional inbred laboratory strains. DNA isolated from mouse organs by standard techniques was digested with restriction endocleases and 10 µg samples were electrophoresed in 0.9% agarose gels. DNA was transferred to Nytran membranes (Schleicher & Schuell, Inc., Keene, N.H.), hybridized at 65° C. with probes labeled by the random primed method with [$^{32}$P]-dCTP, and washed under standard conditions. Gene linkage was determined by standard segregation analysis. Gene order was determined by analyzing all haplotypes and minimizing crossover frequency between all genes that were determined to be within a linkage group (Watson and Seldin, 1994, *Methods in Mol. Genet.* 5:369). This method resulted in determination of the most likely gene order (Bishop, 1985, *Genet. Epidemiol.* 2:349). Previous studies have defined the restriction fragment length variants (RFLVs) and chromosomal locations in this interspecific cross of the following reference loci used in these analyses: Tsha, Gabrr, Txn, 116, Qdpr, Taut, Rafl, Tcrb, Igk, Adral, D11Sell, Geg, and ThbsI (Taketo et al., 1994, *Genomics*, 21:251–253; Chang et al., 1994, *Development*, 12:3339–3353; Patel et al., 1995, *Genomics*, 25:314–317; Seldin et al., supra; Oakey et al., 1991, *Genomics*, 10:338–344; and Potts et al., 1993, *Biochem. Biophys. Res. Comm.*, 197:100–104; Watson et al., 1992, *Mammalian Genome*, 2:158–171).

Nuclear run-on. Cells were removed form culture plates by scraping with a rubber policeman and pelleted by centrifugation. The pellet was resuspended in NP-40 lysis buffer (10 mM Tris-HCL pH 7.4, 10 mM NaCl, 3 mM MgCl$_2$, 0.5% NP-40, 2 mM phenylmethylsulfonyl fluoride (PMSF)) at 4° C. The nuclei were pelleted, washed in 10 mM Tris-HCL pH 7.4, 10 mM NaCl, 3 mM MgCl$_2$, 2 mM PMSF and resuspended in 50 mM Tris-HCl pH 8.3, 5 mM MgCl$_2$ 0.1 mM EDTA, 40% glycerol. Run-on experiments were performed in a final volume of 200 µl (10$^7$ nuclein/reaction) containing 40 U RNAsin, 1 mM each of ATP, CTP and GTP, 100 µCi $^{32}$P-UTP (800 Ci/mmol), 1× run-on buffer (5 mM Tris-HCl pH 8.0, 2.5 mM MgCl$_2$, 150 mM KCl, 2.5 mM DTT) at 30° C. for 30 min. with constant mixing. The reaction was terminated by addition of 300 µl high salt buffer (0.5 M NaCl, 50 mM MgCl$_2$, 2 mM CaCl$_2$, 10 mM Tris-HCl pH 7.4) containing 100 U RNAse-free DNAase I and incubated for 4 min. at 30° C. SDS and proteinase K were added to final concentrations of 0.8% and 100 µg/ml respectively and incubated for a further 30 min. at 42° C. tRNA (100 µg) and 5 ml of 4M GIT were added and the labeled RNA was recovered by centrifugation (Chirgwin et al., supra). The RNA pellet was resuspended in 50% formamide, 1× MOPS pH 7.4, denatured at 65° C. for 10 min. and equivalent amounts were used to probe FIN plasmids immobilized on nitrocellulose filters (Micron Separatins Inc.).

Results

Isolation of FGF-inducible clones. A subtractive hybridization screen was developed to isolate FGF-4 inducible cDNAs. The A15 cell line derived form NIH3T3 cells transfected with a human genomic fragment of the FGF-4 gene was employed as the induced cell population (Delli Bovi and Basilico, 1987, supra). These cells constitutively express and secrete FGF-4. Ectopic expression of FGF-4 in A15 cells has been previously shown to induce several important hallmarks of transformation including morphological changes, proliferation in serum-free medium, growth in soft agar and the formation of solid tumors in nude mice (Talarico and Basilico, 1991 Mol. Cell Biol. 11:1138). Non-transformed NIH 3T3 cells constituted an uninduced cell population. Both cell populations were grown asynchronously in the presence of 10% serum in order to reduce the likelihood of isolating immediate early genes. A subtracted cDNA probe was generated by hybridization of A15 cDNA to an excess of biotinylated mRNA from NIH3T3 cells under stringent conditions for up to 36 h. Hybridized cDNA-mRNa sequences common to both cell populations were removed with the aid of streptavidin and organic extraction as described in Materials and Methods. The resulting subtracted probe was amplified and radiolabeled using PCR and used to screen a cDNA library derived from A15 cells.

A total of 145 positive clones were isolated and examined using a reverse-Northern screening procedure developed to a quantitate the expression of isolated cDNAs in A15 and NIH 3T3 cells. Isolated cDNAs were applied to triplicate filters using a slot blot apparatus and probed with $^{32}$P-labeled cDNA derived from either A15 cells, quiescent NIH3T3 cells, or growing NIH 3T3 cells. The comparative signal intensity for a particular clone obtained with the A15 cDNA probe and the NIH3T3 cDNA process derived from quiescent and growing cells was found to reflect the mRNA expression levels for the clone in each cell type. cDNAs encoding genes exhibiting, (1) A15 specific expression (FIN19), (2) elevated expression in A15 cells relative to either quiescent or growing NIH3T3 cells (FIN1, 3 and 4) and (3) similar expression in A15, quiescent NIH3T3 and growing NIH3T3 cells (clone A3-3) were found. Clones exhibiting stronger signals when probed with cDNA derived from A15 cells compared to NIH3T3 cells were selected for further analysis.

Of the 145 positive clones isolated, reverse-Northern analysis indicated that 45 (31%) encoded A15-specific transcripts, 34 (24%) encoded transcripts with elevated expression in A15 cells compared to either quiescent or growing NIH 3T3 cells and 66 (45%) encoded transcripts with the same or lower expression in A15 cells compared to NIH3T3 cells. Clones representing transcripts with A15 specific expression or elevated expression in A15 cells (79 cDNAs) were then screened for cross hybridization to yield a final pool of 21 unique clones. Due to the method of their isolation, these genes will be referred to as FGF-inducible (FIN) genes.

Sequence analysis of FIN cDNAs. Partial sequencing of the cDNA ends and searches of the GenEMBL databases using the FASTA algorithm (Pearson and Lipman, 1988, Proc. Natl. Acad. Sci. USA, 85:2444–2448) as well as the BLASTP program (Altschul et al., 1990, J. Mol. Biol., 215:403–410) revealed that 12 cDNAs represented previously isolated genes and nine were novel sequences. Clones FIN13–21 corresponded to novel genes. Sequencing of FIN13 and translation of a putative open reading frame (ORF) revealed that it would encode a protein of 392 amino acids with homology to the catalytic domain of several type 2C phosphatases. Type 2C phosphatases encode a family of cytoplasmic serine/threonine phosphatases that require divalent cations for activity.

Regulation of FIN genes in NIH 3T3 cells by growth factors. Northern blot analysis indicated that known genes FIN1–10 exhibited late induction following FGF-4 stimulation of quiescent NIH 3T3 cells. Maximal expression for FIN genes was typically 8–18 h following stimulation and clearly exhibited delayed kinetics compared to c-fos. Similar regulation of FIN1–10 was also observed following serum stimulation (data not shown).

In addition, the expression of FIN genes were generally higher in A15 cells than in growing NIH3T3 cells, although exceptions were observed such as with p63, where higher expression was observed in NIH3T3 cells. Expression of the retroviral transcripts FIN11 and FIN12 was observed in A15 cells but not NIH3T3 cells (data not shown).

Northern blot analysis of novel clones FIN13–17 also revealed late induction following stimulation with FGF-4. An essentially identical regulation of FIN13–17 genes was observed following serum stimulation (data now shown).

Regulation of FIN13 in PC12 cells. While FGF-4 has potent mitogenic activity for a range of mesenchymal cells including fibroblasts, it also capable of stimulating the differentiation of the PC12 pheochromocytoma cell line. Upon FGF (or nerve growth factor—NGF) stimulation, chromaffin-like PC12 cells differentiate to cells exhibiting many molecular and morphological characteristics of sympathetic neurons, including extension of neurites (Rydel and Greene, 1987, J. Neurosci., 7:3639–3653). PC12 cells were employed to examine the regulation of FIN13 in response to proliferative signals (serum) and differentiative signals (FGF-4/NGF). The outgrowth of neurites was only observed in FGF-4 or NGF treated PC12 cultures and greater than 90% of cells had extended neurite-like processes after 4 days.

Cells were starved for 48 h in 0.2% serum and then stimulated with either serum or FGF-4. Although PC12 cells do not become quiescent following growth factor withdrawal, a number of components of growth factor signal transduction pathways have been observed to be down-regulated (Gomez and Cohen, 1991, Nature, 353:170–173; Buchkovich and Ziff, 1994, Mol. Biol. Cell, 5:1225–1241). Serum stimulation of starved PC12 cells results in a modest induction of FIN13 transcripts with maximum expression after 6 h which, thereafter, decreased until 24 h. Similar regulation of FIN13 was observed when starved PC12 cells were stimulated with FGF-4 with maximum expression detected at 12 h which decreased until 96 h.

The weak expression of the novel FIN13 clone in PC12 cells compared to NIH 3T3 cells could imply a non-obligatory role for this genes in regulating cell growth. However, PC12 cells do not respond to serum starvation with a viable $G_0$ arrest. The lack of induction of FIN13 may therefore simply reflect the continual cell proliferation that occurs in the presence of low serum. On the other hand, the increased expression of cyclin D1 following FGF treatment indicates that induction of neuronal differentiation results in significantly increased expression of specific genes in PC12 cells. Thus the lack of, or very weak induction of most of the FIN genes following FGF (or NGF) treatment of PC 12 cells suggests that most of these genes are only induced following a proliferative stimulus.

Discussion

Central to the mitogenic activity of FGF-4 is its ability to initiate and maintain a genetic program that results in cell division. Through application of a subtractive hybridization procedure for the isolation of FGF inducible (FIN genes)

from the FGF-4 transformed A15 cell line, 21 cDNAs have been cloned. Dideoxy sequencing has revealed that FIN1–12 cDNAs encoded a variety of known transcripts/proteins including cyclin D1, a G-beta-like polypeptide, the HSP homologue $ER_p99$, non-neuronal alpha enolase, a lysosomal associated membrane protein LAMP-1, a heat shock binding protein p59, a protein of the endoplasmic reticulum-Golgi compartment p63, several mitochondrial transcript sand viral sequences. In addition, comparison of partial sequences of FIN13–21 to the GenEMBL databases indicated that these clones were unique and exhibited only limited, or no homology, to known sequences.

Analysis of the regulation of FIN genes in NIH 3T3 cells following growth factor stimulation showed that 17 clones encoded late-inducible genes, one clone encoded a gene down-regulated by growth factors and three clones encoded genes that were specifically expressed in A15 cells. The number of growth regulated clones isolated with this screen and their diverse nature emphasize the complex and highly regulated genetic program required to undergo cell division. Similar observations have been made by other investigators who have examined the complex regulation of gene expression by growth factors (Lanahan et al., 1992, *Mol. Cell. Biol.*, 12:3919–3929).

Although this work was originally initiated with the intent of isolating at least some genes specifically induced by FGF-4 and not by other growth factors, the fact that all FIN genes tested so far are also inducible by serum clearly indicates that the majority of the genes that have been identified are growth regulated. Signal transduction by growth factor and cytokine receptors has been so far shown to follow a limited number of pathways most of which appear to be shared by very different receptors (Hill and Treisman, 1995, *Cell*, 80:99–211). While, for example, the identification of the interferon/STAT signal transduction pathways appeared initially to be unique to interferons and some cytokines, recent results indicate that this pathway is also used by tyrosine kinase receptors such as the EGF receptor (Silvennoinen et al., 1993, *Science*, 261:1736–1739). In view of this, it is perhaps not surprising that the FIN genes are not FGF specific, and these findings further highlight one of the central questions in signal transduction, i.e., how do growth factors induce a specific cellular response? Indeed, some of the FIN genes could be specifically induced by FGFs in other cell types.

Due to its strong regulation in NIH 3T3 cells, and lack of identity with known sequences, FIN13 was selected for further analysis. The tissue distribution for FIN13 mRNA was restricted with strongest expression detected in only one tissue, the testis. Interestingly, testes tissue undergoes continual dynamic change involving cell proliferation and differentiation. In line with these results, FIN13 was also detected in mouse embryos.

The possible role of FIN13 in cell growth and differentiation was further investigated in PC12 cells. FIN13 exhibited a modest induction in PC12 cells in response to mitogenic stimulation (serum) and differentiative stimulation (FGF-4). PC12 cells, however, do not respond to serum starvation with a viable $G_0$ arrest, and thus the lack of induction of FIN13 expression may simply reflect the fact that this gene is already expressed under serum deprivation. The regulated expression of FN13 in NIH3T3 cells and quasiconstitutive expression in PC12 cells could imply that other mechanisms in addition to cell growth account for the regulation of this gene. On the other hand, this gene could be part of a proliferative response to growth factors, and as such does not have to be induced in tumor cells which express them constitutively. At any rate, these results indicate that most of the FIN genes are not induced during PC12 cells differentiation, and thus are likely to represent genes whose induction is specific for cell proliferation. While NIH3T3 and PC12 cells show a very similar immediate-early response to various growth factors (Chao, 1992, *Cell*, 68:995–997), these results highlight significant differences between the cell types in the late response induced following growth factor treatment.

Additional possibilities for the functional correlation of the novel FIN13 gene is raised by the chromosomal localization data (see infra). Of potential interest, the FIN13 gene mapped to a region of mouse chromosome 5 consistent with the position of the mouse luxate (lx) mutation. Penetrance of the lx phenotype is semi-dominant and dependent on genetic background. Homozygotes show preaxial polydactyly or oligodactyly of the hindfeet, reduction of the tibia, loss of a part of the femur and pubis, decrease in the number of presacral vertebrae, and anomalies of the urogenital system (Carter, 1951, *J. Genet.*, 50:277–299; Carter, 1953, *J. Genet.*, 51:441–457). Interestingly, the abnormalities of homozygotes can be traced back to day 10 embryos when FIN13 is highly expressed. The ability of FGF-4 to orchestrate passage through the cell cycle is contingent upon the induction of a complex genetic program that enables the synthesis of the necessary RNAs and proteins for cell division. Given its pleiotropic activities, FGF-4 is likely to be capable of transducing multiple genetic programs, the nature of which is likely to be determined by the identity of the stimulated cell. For example, the observed regulation of FIN13 mRNA in response to growth factors and its homology to the type 2C serine-threonine phosphatase family, makes it tempting to speculate that the FIN13 protein is involved in regulating reversible phosphorylation known to be important in growth factor signal transduction (Hunter, 1995, *Cell*, 80:225–236). These investigations into the FIN genes described in this study thus provide important insights into the mechanism by which FGF-4 and other growth factors exert their diverse biological activities on a variety of cell types as well as pointing the way to modulating cellular proliferation by intervening in the activity of these inducible genes and their encoded proteins, notably FIN13.

EXAMPLE 2

CHARACTERIZATION OF FIN13

Fibroblast growth factors (FGFs) are important for mediating a wide range of biological processes involving cell proliferation and differentiation in vivo. This Example sheds light on one of the molecular mechanisms by which these factors stimulate a biological response.

The possible mechanisms by which the FGFs exert their biological activity were addressed by identifying genes regulated by the FGFs (Example 1, supra). This Example shows that genes that are regulated by the FGFs in vitro are also regulated in vivo in tissues that are known to produce FGF, and characterizes a growth inhibitory function of one of the genes. A subtractive hybridization procedure was employed to isolate a number of cDNAs from the FGF-4 (K-FGF) transformed A15 cell line. The expression of corresponding A15 cell RNAs was induced following FGF-4 stimulation of murine NIH 3T3 cells. Thus, these cDNAs encode growth factor inducible genes and have been termed FIN (EGF-inducible) genes. Sequencing of these cDNAs revealed that several contained putative open reading frames (ORFs) that encoded novel proteins. One such clone, FIN13, encodes a novel type 2C serine/threonine phosphatase, which the studies described herein indicate is a possible negative regulator of cell growth.

Sequence Analysis of the FIN13 cDNA

The sequence of the FIN13 cDNA is shown in FIG. 1. Translation of the FIN13 cDNA revealed a single long ORF encoding for a protein of 392 amino acids Met=+1). The cDNA sequence flanking the putative translation initiation codon at 214, GCTACCATGA (SEG ID NO:5), is in good agreement with the consensus sequence for translation initiation in eukaryotic mRNA (GCC$^G/_A$CCAUGG)(SEQ ID NO:6). The 5'-end of the cDNA was confirmed by:1) sequence analysis of an additional 20 FIN13 cDNAs isolated from the A15 cDNA library; and 2) by a rapid amplification of cDNA ends-polymerase chain reaction (RACE-PCR) approach. The results obtained from these two independent methods suggest that the 5'-end of the FIN13 cDNA is as shown in FIG. 1 (SEQ ID NO:1) and the ATG codon at 214 would serve as a translation initiation codon. Northern blot analysis showed that the FIN13 cDNA detected a single mRNA species of approximately 2.1 kilobases (kb) in NIH 3T3 cells (FIG. 4), while the longest FIN13 cDNA isolated from the A15 library was 1.8 kb. This discrepancy could be due to an incomplete 3'-untranslated end. In fact, no consensus sequence for polyadenylation was observed adjacent to the 3'-poly A tail, possibly indicating internal priming of the oligo-dT during cDNA synthesis.

Analysis of the putative FIN13 amino acid sequence with Genbank revealed 3 distinct homology domains and a possible subcellular targeting motif (FIG. 2). An N-terminal domain of approximately 100 amino acids exhibited weak homology to a range of collagens including mouse alpha-2 (IV) collagen (29% identical over 104 amino acids and chicken alpha-3 (IX) collagen (29% identical over 108 amino acids). A central acidic box, rich in aspartic acid and glutamic acid residues (65% over 62 amino acids). A central acidic box, rich in aspartic acid and glutamic acid residues (65% over 62 amino acids), exhibited homology to a number of acidic proteins including several nuclear proteins and transcription factors. A C-terminal region exhibited high homology to the catalytic domain of several type 2C phosphatases from *S. cerevisiae* (46% identical), *C. elegans* (45% identical), rat (38% identical), rabbit (36% identical), and mouse (35% identical). Comparison of FIN13 to various serine/threonine kinases is shown in FIG. 3. Finally, a putative unclear translocation sequence (charged domain) similar to that of polyoma virus (VSRKRPRP) (SEQ ID NO:11) and (PKKKRKV) (SEQ ID NO:12) large T antigen was observed at the extreme C-terminal of FIN13 (SEQ ID NO:13).

The homology of FIN13 to type 2C phosphatases did not extend beyond the catalytic domain of these proteins and no significant homology was observed for other classes of phosphatases. Based on these data, FIN13 appears to encode a new member of this family of enzymes.

Regulation of FIN13 mRNA by Growth Factors

Northern blot analysis revealed that FIN13 mRNA was inducible by FGF-4 in NIH 3T3 cells (FIG. 4). A maximum induction of 6-fold following 18 h stimulation was observed. Similar induction of FIN13 mRNA was observed in response to serum. Stimulation of NIH 3T3 cells for 18 h with FGF-4 in the presence of 10 mg/ml of the protein synthesis inhibitor, cycloheximide, did not result in induction of FIN13 confirming that this cDNA encodes a late inducible gene. The effect of cycloheximide on the induction of FIN13 mRNA was evaluated as follows. NIH 3T3 cells were starved for 48 h in DMEM/0.5% CS and stimulated for 0, 0.5, and 12 h with 100 ng/ml FGF-4 in the absence (–CHX) or presence (+CHX) of 10 µg/ml of cycloheximide. Total RNA (10 µg) was examined by Northern analysis for the induction of FIN13 mRNA.

In order to determine whether the induction of FIN13 mRNA reflected an increased rate of transcription, a nuclear run-on experiment was performed. Nuclei were isolated from quiescent NIH 3T3 cells (Q) or NIH 3T3 cells stimulated for 18 h with FGF-4 (S) and se novo RNA synthesis was measured by $^{32}$P-labeling of nascent RNA chains. Transcriptional activation of FIN13 following growth factor stimulation was observed. Thus, these results indicate a transcriptional mechanism to account for the increased steady state levels of FIN13 mRNA observed in FIG. 4, although post-transcriptional mechanisms may also contribute.

Tissue Distribution of FIN13 mRNA

Northern analysis of the tissue distribution of FIN13 mRNA in adult mouse tissues was also performed. FIN13 cDNA detected a single highly expressed transcript in the testis with low level expression also detected in the kidney and ovary. The expression of FIN13 transcripts was also determined on whole mouse embryos from day 10.5 to day 15.5 post-coitus. FIN13 transcripts were elevated in mouse embryos at E10.5 and became down-regulated thereafter. FIN13 RNA is expressed in a range of mouse tissues undergoing proliferation, such as the pregnant uterus, the placenta, and ovaries stimulated to undergo folliculogensis with diethylostilbesterol. In addition, FIN13 mRNA is also expressed in three murine tumors (B16 melanoma, Lewis lung carcinoma and Bladder carcinoma) and the murine F9 embryonal carcinoma cell line. Induction of FIN13 by growth factors in cultured cells and its induction in diverse tissues undergoing proliferation could imply that FIN13 serves an important role in mediating the cellular response to growth factor.

The cellular localization of FIN13 transcripts has also been examined by in situ hybridization in mouse testis and embryos. Using a $^{35}$S-labeled FIN13 antisense RNA probe, the hybridization signal was localized to the seminiferous tubules in mouse testis. No significant signal was obtained with the sense probe control. FIN13 mRNA is most likely expressed in germ cells as no specific signal was obtained in testis of mutant white spotted (sp/sp) mice that lack germ cells but have normal interstitial cells as determined by several criteria. The intra-tubular compartment contains both germ cells which undergo a differentiation program that involves mitogenic and meiotic cell divisions to produce sperm cells and also somatic Sertoli cells which undergo proliferation. FIN13 expression did not appear to localize to germ cells at a particular stage of development possibly indicating that FIN13 serves some general role in cell proliferation/differentiation within the testis. In situ hybridization was also performed on mouse embryos using $^{35}$S-labeled FIN13 antisense and sense RNA probes. Hybridization signals in E10.5 and E12.5 day embryos indicated that FIN13 RNA is widely expressed in embryonic tissues with particularly high expression in the liver.

Mouse Chromosomal Localization and Fine Mapping

In order to determine the chromosomal location of the FIN13 gene, a panel of DNA samples from an interspecific cross that has been characterized for over 900 genetic markers throughout the genome was analyzed. The genetic markers included in this map span between 50 and 80 centi-morans on each mouse autosome and the X chromosome (Chr). Initially DNA from two parental mice [C3H/ HeJ-gld and (C3H/HeJ-GLD x Mus spretus)F$_1$] were digested with various restriction endonucleases and hybridized with the FIN13 cDNA probes to determine restriction fragment length variants (RFLVs) to allow haplotype analysis. The FIN13 gene was found to be located on the proximal end of mouse chromosome 5; (centromere) IL6—4.4 cM+/−1.9 cM—FIN13—11.4 cM+/−3.1 cM+/− dpr. FIN13 localized to the luxate (lx) locus on mouse chromosome 5. Penetrance of the lx phenotype is semi-dominant and dependent on genetic background. Homozygotes show paraxial polydactyly or oligodactyly of the hindfeet, reduction of the tibia, loss of a part of the femur and pubis, decrease in the number of presacral vertebrae, and anomalies of the urogenital system. Interestingly, the abnormalities of homozygotes can be traced back to day 10 embryos when FIN13 is highly expressed. The likely human homologous chromosomal localization for FIN13 is on Chr 4 at 4p 16.3–16.1.

EXAMPLE 3

EXPRESSION AND ACTIVITY OF FIN13

Material and Methods

Construction of expression plasmids. The FIN13 cDNA and its catalytic domain were cloned into pET28b(+) vectors (Novagen) by PCR for expression of full length polypeptide or the catalytic domain as a fusion protein with a polyhistidine tag. The complete ORF was amplified using oligonucleotides GAGAGGATCCCATGACTATTGAA-GAGCTGCTG (containing a BamHI site) (SEQ ID NO:14) and CTCTCGCGGCCGCGTCCCTCTTGGCCT-TCTTTTTG (containing a NotI site) (SEQ ID NO:15) and cloned after BamHI/NotI digestion into the BamHI/NotI site of pET28b(+) to give vector pET24-8-2-7 (pEThis-FIN13). This construction resulted in the expression of a FIN13 fusion protein containing both an N- and a C-terminal poly(6)-histidine tag with the pET28 a stop codon being utilized. A vector that contained the catalytic domain was constructed by digestion of pET24-8-2-7 with BamHI/ HindIII which removed the sequences encoding the collagen homology domain and the acidic box, and the linearized vector was relegated with a BamHI/HindIII adaptor to yield pEThis-FIN13-cat, which produced the catalytic domain of FIN13 (amino acids 195 to 392) with N- and C-terminal poly(6)-histidine tags.

For expression of FIN13 in mammalian cells, the FIN13 cDNA in Bluescript was subcloned into the pRK5 mammalian expression vector in several steps. A HgaI/blunted SpeI fragment of the original FIN13 cDNA was subcloned using a XhoI/HgaI adaptor made by hybridizing oligonucleotides with the sequence, 5'-TCGAGGCCACCATGACTATTGAAGAGCTGCT-GACGCGATAT-3' (SEQ ID NO:16) and 5'-TGCC-CATATCGCGTCAGCAGCTCTTCAATAGTCATGGTG-GCC-3' (SEQ ID NO:17) into the XhoI/EcoRV site of pMJ30 to give pMJFIN13. A blunted BglII/partial HindIII digested fragment was released from pMJFIN13 and subcloned into the HindIII/SmaI site of bluescript (KS) to give pBFIN13–15. pRKFIN13 was made by subcloning the ClaI/BamHI fragment from pBFIN13–15 into ClaI/BamHI site of pRK5. pRKmyc-FIN13 expressing FIN13 N-terminally fused to the myc epitope was made by sub-cloning hybridized oligonucleotides into the ClaI site of pRKFIN13. The sequence of the oligo for the sense strand was:

5'-CGATGCCACCATGGAACAGAAACTGATTTCC-GAAGAAGATCTGAT-3' (SEQ ID NO:18). Sequencing revealed that pRKmyc-FIN13 contained two copies of the myc epitope in-frame with, and N-terminal to, the FIN13 open reading frame. The construct expressing FIN13 under the control of the tet operon, pUHDFIN13, was made by subloning the XbaI/blunted ClaI FIN13 cDNA from pRK-FIN13 into the XbaI/blunted EcoRI site of pUHD10-3 (Gossen and Bujard, Proc. Nat. Acad. Sci. USA 89:5547–5551 (1992)). The open reading frames of all FIN13 expression constructs were confirmed by sequencing.

The FIN13 cDNA was isolated by KpnI and partial EcoRI digestion and cloned into the XmnI site of the pMal-c2 (New England Biolabs) vector in the correct orientation. This construction resulted in an in-frame fusion of the FIN13 sequence with the maltose binding protein. (MBP-FIN13).

Preparation of $^{32}$P-labelled casein. Casein (10 mg) (Sigma) was labelled with $^{32}$P using 10U of the catalytic subunit of cAMP dependent protein kinase (Sigma) in 50 mM Tris-HCl pH 7.0, 0.1 mM EGTA, 10 mM Mg-acetate, 0.1% β-mercaptoethanol, and 0.5 mCi of $^{32}$PγATP for 12 h at 30° C. The reaction mixture was then precipitated at 4° C. in 20% TCA. Labelled casein was recovered by centrifugation, the pellet washed 5 times in 100% acetone and resuspended in 50 mM Tris-HCl, 0.1 mM EGTA.

Phosphatase assay. The phosphatase activity of purified FIN13 expressed in bacteria as a fusion protein with N- and C-terminal His-tags was assessed in vitro using $^{32}$P-labelled casein as a substrate. For preparation of his-FIN13 and his-FIN13-cat from bacteria, the BL21 (DE3) strain transformed with PETHis-FIN13 or pETHis-FIN13-cat were induced with 0.2 mM IPTG for 2 h following which the cells were recovered by centrifugation, resuspended in column buffer (50 mM sodium phosphate, pH 8.0, 300 mM NaCl, 1 mM PMSF) and frozen overnight at −70° C. The bacteria were then lysed by sonication at 4° C. and the extract cleared by centrifugation. The supernatant was then adsorbed to Ni-NTA-agarose (Qiagen)at 4° C. for 1 h. The resin was then washed extensively in column buffer without PMSF and His-FIN13 or His-FIN13-cat were eluted using 25 mM Tris-HCl pH 7.2, 100 mM NaCl containing 0.2 mM imidazole (Sigma). In addition, the phosphatase activity of FIN13 expressed in HeLa cells was also determined in an immune complex using $^{32}$P-labelled casein as a substrate. For preparation of immune complexes of myc-FIN13, HeLa cells were transfected with 10 μg of pRKmyc-FIN13 or pRK5. Cells were lysed 24 h after transfection in lysis buffer (1 mM Na-phosphate pH 7.4, 100 mM NaCl, 1% TRITON X-100, 10 mM EDTA) also containing a protease/phosphatase inhibitor cocktail (1 mM PMSF, 1 μg/ml pepstatin, 1 μg/ml leupeptin, 1 μg/ml aprotinin, 10 mM Na-orthovanadate, 80 mM NaF, 80 mM β-glycerolphosphate, 10 μM okadaic acid). Cleared lysates (100 μg total protein) were immunoprecipitated with anti-myc monoclonal antibody (9E10) adsorbed to 30 μl protein G sepharose (Zymed) or anti-FIN13 antiserum adsorbed to 30 μl protein A sepharose (Zymed) for 1.5 h at 4° C. The anti-FIN13 polyclonal antiserum (630) was generated against the full length His-FIN13 expressed and purified from bacteria. The IPs were then washed 5 times with lysis buffer, once with 10 mM Tris-HCl pH 7.0, 100 mM NaCl and 5 mM MnCl$_2$, and twice with phosphatase reaction buffer (10 mM Tris-HCl pH 7.0, 0.1 mM EGTA, 10 mM DTT and 10 mM MnCl$_2$) containing 1 μM okadaic acid. Purified His-FIN13, His-FIN13-cat or myc-IPs were then examined for phosphatase activity by incubating the indicated FIN13 preparation in the presence of phosphatase reaction buffer containing $^{32}$P-labelled casein (1×10$^5$ cpm; approx. 1 μl) at 30° C. for up to 2 h. Okadaic acid (1 μM), poly L-lysine (20 μg/ml), protamine sulfate (20 μg/ml) were added where indicated and were pre-incubated with FIN13 preparations at 30° C. for 5 min prior to addition of the $^{32}$P-labelled substrate. All phosphatase assays performed with immunoprecipitated myc-FIN13 contained 1 μM okadaic acid. After incubation total protein was then precipitated by adding TCA to a final concentration of 20% (w/v) and insoluble material was pelleted by centrifugation. Inorganic $^{32}$P recovered in the supernatant was monitored by scintillation counting.

Transfection of cells. Cells were maintained in DMEM/ 10% calf serum as previously described in Examples 1 and 2, supra. NIH 3T3, Rat1 or HeLa cells were transfected for 12–19 h by CaPO$_4$ precipitation using standard procedures. For the isolation of stably transfected cell lines, cells were plated out 24 h after transfection in DMEM/10% calf serum containing 400 μg/nml G418 (Gibco-BRL) or 250 μg/ml hygromycin B (Calbiochem). Single cell originated clones were selected after 7–10 days. To establish cell lines that express inducible FIN13, NIH3T3 cells were firstly co-transfected with 5 μg of pUHD15-1 (construct expressing tTA) (Gossen and Bujard, 1992, supra) and 0.2 μg pRSVneo that contains the G418 resistance gene. After 2 weeks of G418 selection, colonies were picked and screened for the expression of tTA by transient transfection of a construct expressing luciferase under the control of the tet operon (pUHC13-3) as described by Gossen and Bujard (Gossen and Bujard, 1992, supra). Clones found to express inducible tTA in the luciferase assay were co-transfected with 5 μg pUHDFIN13 and 0.2kg pCEP4 that contains the hygromycin B resistance gene, in DMEM/10% calf serum containing 1 μg/ml tetracyclin (Sigma). Twenty four hours after transfection, cells were plated into medium containing 1 μg/ml tetracyclin, 250 μg/ml hygromycin B and 400 μg/ml G418. Medium was changed every 4-5 days and fresh tetracyclin (1 μg/ml) was added every day. Drug resistant clones were picked after 2-3 weeks and cultured using the same protocol.

COS-7 cells were transfected with 5 μg of pRKFIN using standard DEAE-Dextran protocols. Cells were harvested by scraping with a rubber policeman and the cytoplasmic fraction obtained by extraction in lysis buffer (10 mM Na$_2$HPO$_4$pH 7.5, 100 mM NaCl, 10 mM EDTA, 1% Triton X-100, 1 mM PMSF, 1 μg/ml pepstatin, 1 μg/ml leupeptin, and 5 μg/ml aprotinin). Nuclei were pelleted by centrifugation, and the supernatant recovered. The extracts were either examined directly by western blot for FIN13 or firstly immunoprecipitated using the antiserum to a protein-A Sepharose resin for 1.5 hours at 4° C. and then incubating the cell extracts from the transfected COS-7 cells with the resin also for 1.5 hours at 4° C. The resin was then washed 4 times in lysis buffer and the resin boiled in gel loading buffer and electrophoresed on to a 8% polyacrylamide gel for analysis by Western blot.

Western blot analysis. Cells were lysed in lysis buffer containing a protease/phosphatase inhibitor cocktail (see above). Equal amounts of lysates (determined by Bradford protein staining reagent; Biorad) were electrophoresed on an SDS-polyacrylamide gel and transferred at 40° C. to a nitrocellulose membrane (MSI). Equal loading was confirmed by staining in 0.2% Ponceau, 6% TCA. The membrane was blocked overnight at 4° C. in 5% BSA in PBS followed by incubation with primary and secondary antibodies for 1 h each at room temperature and finally developed with enhanced chemiluminescence (Amersham) using standard procedures. Anti-FIN13 polyclonal antibodies (630) were used at a dilution of 1:500. Anti-myc monoclonal antibodies (9E10 hybridoma supernatant) was used at 1:25.

Antisera were prepared using either purified MBP-FIN13 or His-FIN13. The results obtained in Western blots and immunoprecipitations were identical for both antisera. Results obtained from the anti-MBP-FIN13 are presented in this application. The immunization protocol is as follows: rabbits were injected with 100 μg of purified antigen/ Freund's adjuvant on day 0, followed by boosts at day 14, 21, and 49. Antisera were screened for anti-FIN13 reactivity and specificity using Western blot analysis. In one instance, antisera were used in Western blots directly at a 1:300 dilution without additional purification.

Effect of FIN13 expression on the growth of neomycin-resistant cells. NIH 3T3 cells were co-transfected with pRSVneo (0.2 μg) and either pRK5 or pRKFIN13 (5 μg), and neomycin-resistant transfectants were selected in G418 after plating. Cells were stained after 2 weeks in crystal violet. Whole cell extracts prepared 24 h following transfection or after 2 weeks selection in G418 were examined for the expression of FIN13 by Western blot analysis using the anti-FIN13 antiserum (630).

Growth curves of tetracyclin inducible cells. Cell lines found to demonstrate FIN13 inducible expression following tetracyclin removal were examined for their growth properties. Cells were plated in triplicate at 10000 cells/ml in 24 well plates in DMEM, 10% dialysed calf serum in either the presence or absence of 1 μg/ml tetracyclin. Cells were counted every day (Coulter counter) and media, with or without tetracyclin was changed every 2 days.

Bromodeoxyuridine (BrdU) incorporation. The effect of FIN13 expression on BrdU incorporation was determined in HeLa cells growing asynchronously in DMEM/10% calf serum. Cells were plated at 10000 cells/ml on coverslips and after 24 h were transfected with 10 μg of either pRKERK2-HA, CMVβ or pRKFIN13. Twenty four hours after transfection the medium was changed and the cells were incubated with BrdU labelling reagent (10 μl) for a further 12 h according to the suppliers instructions (Boehringer Mannheim). Following labelling, coverslips were rinsed in PBS and cells were fixed in 70% ethanol-50 mM glycine (pH 2.0) overnight at −20° C. Incorporated BrdU was detected with FITC-conjugated anti-BrdU (Boehringer Mannheim) by immunocytochemistry (see below).

Immunocytochemistry. Fixed cells on coverslips were washed twice in PBS and twice in PBS/0.02% BSA followed by incubation with the primary antibody diluted in PBS/ 0.02% BSA for 1 hour at 37° C. (anti-FIN13 polyclonal serum at 1:200, anti-HA monoclonal antibody 12CA5 acities at 1:200 or anti-β-galactosidase GAL40 monoclonal antibody at 1:500). After washing, coverslips were incubated in secondary antibody as above (anti-rabbit Texas red at 1:200, anti-mouse Texas red at 1:200)(Molecular Probes). The coverslips were washed again and then incubated in 200 μg/ml (1:500) FITC-conjugated anti-BrdU (Boehringer Mannheim) as above. Where noted, cells were also stained with 1 μg/ml bis-benzimide (Hoechst # 33342) in PBS. Coverslips were mounted and examined using a fluorescence microscope.

Fluorescence activated cell sorting (FACS). HeLa cells growing asynchronously in DMEM/10% calf serum were co-transfected with 5 mg of a plasmid expressing a humanized version of green fluorescent protein (GFP)

(pcDNA3hGFP) and 15 μg of either pRKERK2-HA, CMVβ or pRKFIN13. Thirty six hours or 60 h after transfection the cells (5–10×10⁶ cells) were washed, harvested by trypsinization and GFP expressing cells were recovered by FACS. Cells were then fixed in 80% ethanol at −20° C. overnight and recovered by centrifugation. The fixed cell pellet was then resuspended in 0.75 ml of PBS and DNA was stained with propidium iodide (Sigma) (200 μg/ml propidium iodide, 40 mM sodium citrate, pH 7.0) containing 100 μg/ml RNAase A (Sigma) at 37° C. for 2 h. Cells were examined for DNA content using a FACScan flow cytometer and the percentage of cells in G0/G1, S and G2/M was determined using ModFit software.

Results

Expression of FIN13. Labeled FIN13 was obtained from metabolic labelling of FIN13 with $^{32}$P-orthphosphate in pRK24-8-1 transfected NIH 3T3 cells. Cell extracts from these cells were immunoprecipitated using the 549 antiserum and both the 60kDKa and the 70 kDa forms of FIN13 were found to be labelled with $^{32}$P following analysis by polyacylamide gel electrophoroesis.

FIN13 fused to either the maltose binding protein or a histidine-tag were expressed in bacteria, purified and used to raise antibodies in rabbits. The specificity of one such antiserum was shown by detection of a single band of apparent molecular weight (Mr) 60 kDa by Western blot analysis with the 549 antiserum in either whole cell extracts of IPTG-induced bacteria transfected with a construct expressing FIN13 (pET-24-8-2-7) or in COS cells transfected with a FIN13 expression plasmid (pRK24-8-1). Immunoprecipitation with the 549 antiserum from FIN13 transfected COS cells followed by Western analysis also resulted in the detection of a single 60 kDa band. These results indicate that FIN13 is immunogenic, and the 549 antiserum is suitable for both Western analysis and immunoprecipitation of FIN13. Although the FIN13 cDNA is predicted to encode a protein of 42 kDa, both the bacterial and mammalian cells express FIN13 that migrates as a 60 kDa protein on a reducing and denaturing polyacrylamide gel. The reason for this anomalous migration behavior is not understood but may be, in part, due to the highly charged nature of the acidic box.

Overexpression of FIN13 in NIH 3T3 cells by transient transfection with the pRK24-8-1 vector results in the expression of the 60 kDa FIN13, as observed for COS cells, as well as an additional band with an apparent Mr of 70 kDa. NIH 3T3 cells were either transfected with the pRK24-8-1 FIN13 expression plasmid for up to 96 hours (transient) or cotransfected with RSV-neo and pRK24-8-1 and the neo-expressing colonies were selected in the presence of G418 (stable). Clones neo1 and neo2 were transfected with RSV-neo alone and served as controls. Cell extracts from transiently transfected cells or from expanded drug resistant clones were then subjected to direct Western analysis using the 549 antiserum. The bacterial his-FIN13 fusion protein was used as a positive control.

The 549 antiserum recognized a single growth factor inducible 70 kDa protein in non-transfected NIH 3T3 cells following stimulation with serum that had similar induction kinetics as the FIN13 mRNA. Furthermore, the 549 antiserum also detected a single 70 kDa protein with the same testis specific tissue distribution as the FIN13 mRNA. These results would suggest that the endogenous FIN13 protein is predominantly expressed as a 70 kDa protein and that transient overexpression in murine cells results in the appearance of a 60 kDa protein. The relationship between these two forms of FIN13 is currently under investigation. Preliminary results suggest that phosphorylation of FIN13 may be, in part, responsible for the observed differences in molecular weights of the 60 and 70 kDa forms of FIN13. Metabolic labeling of FIN13 transfected NIH 3T3 cells with $^{32}$P-orthphosphast followed by immunoprecipitation of FIN13 from cell extracts with the 549 antiserum indicates that both the 60 and 70 kDa forms of FIN13 are phosphorylated.

Figure 5:
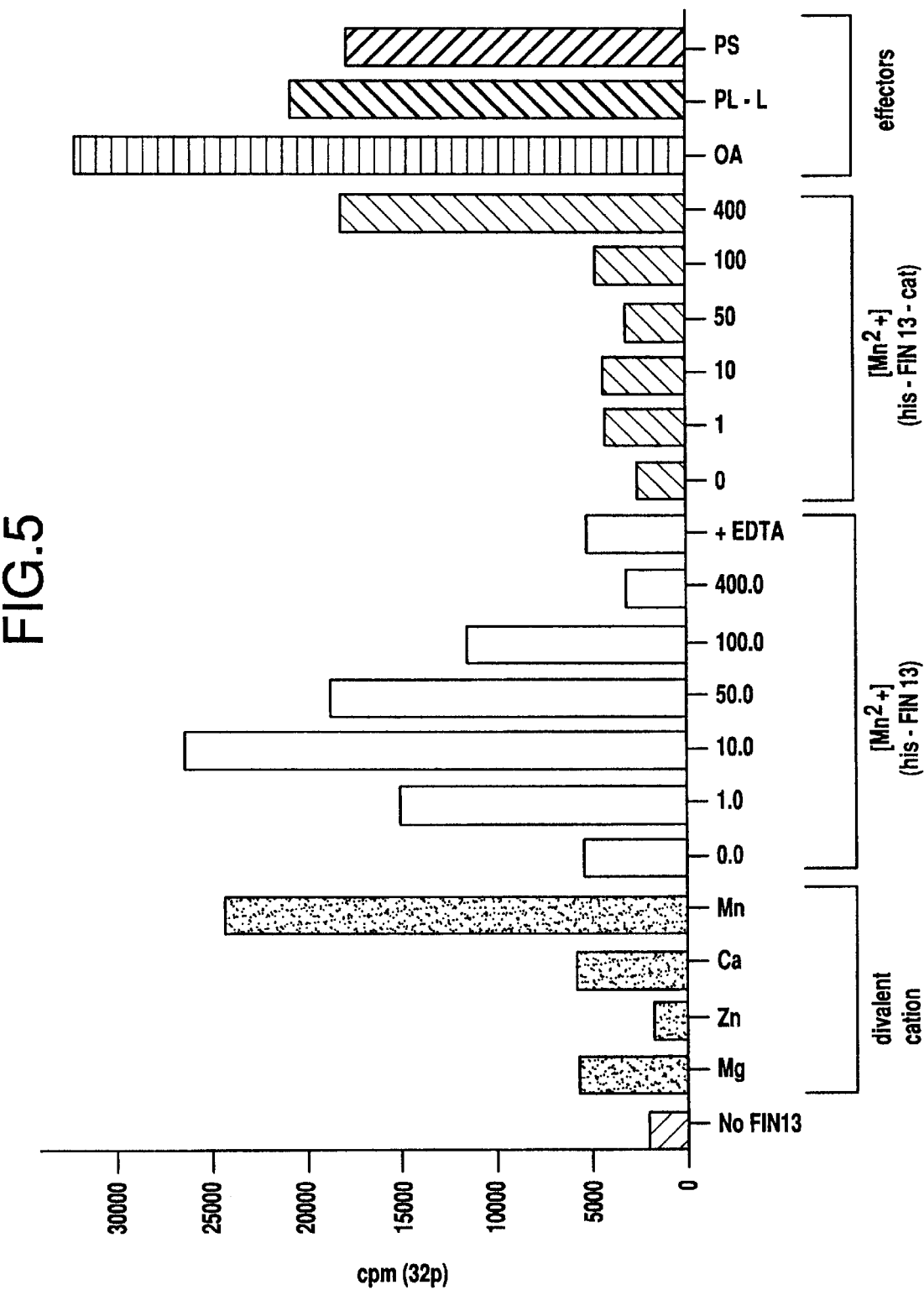
FIG. 5. Phosphatase activity of bacterially expressed FIN13. Purified his-tagged full length FIN13 (his-FIN13) or his-tagged catalytic domain FIN13 (his-FIN13-cat) were examined for their ability to dephosphorylate $^{32}$P-labelled casein in vitro as described in the Materials and Methods. Phosphatase assays were performed in the absence of his-FIN13 (No FIN13, open bar) or with his-FIN13 incubated in the presence of 10 mM of the indicated divalent cation. ($MgCl_2$, $ZnCl_2$, $CaCl_2$ or $MnCl_2$)(solid bars) or in the presence of the indicated mM concentrations of $MnCl_2$ (half-tone bars). +EDTA: indicates his-FIN13 incubated in the presence of 10 mM EDTA and 10 mM $MnCl_2$. his-FIN13-cat was incubated in the presence of the indicated mM concentrations of $MnCl_2$(cross-hatched bars). his-FIN13 was also incubated in the presence of 1 $\mu$M okadaic acid (OA), 20 mg/ml poly L-lysine (PL-L), 20 mg/ml protamine sulfate (PS). All incubations were performed for 1 h at 30° C.

Initial attempts at obtaining stable transfected cell lines that overexpress FIN13 proved difficult. Subsequent studies have indicated that overexpression of FIN13 may have a negative effect on cell growth. For example, co-transfection of NIH 3T3 or Balb/c 3T3 cells with a neo-expressing plasmid and the pRK24-8-2 vector resulted in a decreased number of G418 resistant colonies (selected in the presence of Geneticin for two weeks, followed by fixing and staining with crystal violet) when compared to the pRK-5 (no insert) vector control. Drug resistant colonies were expanded and examined for FIN13 expression levels by Western blot. One phenotype of a gene that inhibits growth is the inability of cells expressing high levels of the protein to expand. Although several clones were isolated that overexpressed the 70 kDa FIN13 relative to non-transfected clones, only a modest level of expression was observed in all clones examined. Nonetheless, the level of overexpression of FIN13, as determined by Western blot, correlated with a decreased growth rate. Clone 11-10 which expressed the highest levels of FIN13 had a doubling time of 20 h while non-transfected controls, neo2 and neo3, had doubling times of 16 h. These results indicate that FIN13 over-expression leads to slowed growth, growth arrest or cell death. Although FIN13 appears to be a negative regulator of cell growth, the presence of FIN13 mRNA and protein in growing cells would indicate that additional controls are likely to be important in regulating FIN13 activity. An inducible system for the overexpression of FIN13 is currently being employed to further investigate, in a more detailed manner, the mechanism by which FIN13 may regulate cell growth. FIN13 is a type 2C phosphatase localized in the nucleus. To determine whether FIN13 was a bonafide type 2C phosphatase, we examined the activity of purified FIN13 expressed in bacteria as a fusion protein with histidine tag (his-FIN13) in vitro. Type 2C phosphatases are characterized by their requirement for divalent cations and their insensitivity to the phosphatase inhibitor okadaic acid (Brautigan, Recent Progress in Hormone Research 49:197–214 (1994); Cohen and Cohen, *J Biol. Chem.* 264:21435–21438 (1989); Hunter, *Cell* 80:225–236 (1995)). his-FIN13 was able to dephosphorylate $^{32}$P-labelled casein in the presence of $Mn^{2+}$ ions with maximal activity obtained at 10 mM $MnCl_2$ (FIG. 5). No activity was observed in the presence of $MgCl_2$, $ZnCl_2$ or $CaCl_2$. Although other type 2C phosphatases have been reported as being active in the presence of either $Mn^{2+}$ or $Mg^{2+}$, his-FIN13 exhibited an absolute requirement for $MnCl_2$. The addition of 10 mM EDTA(+EDTA) to the phosphatase assay abolished activity. We are uncertain whether the restricted requirement for $MnCl_2$ stems from the bacterial expression of his-FIN13 or whether this activity is a feature unique to FIN13. The catalytic domain of FIN13 (his-FIN13-cat) exhibited poor phosphatase activity at 10 mM $MnCl_2$, but activity was detectable at 400 mM. Thus, it would appear that while the catalytic domain alone demonstrates phosphatase activity at high $MnCl_2$ concentrations, other domains are also important for activity or protein conformation, at least in the bacterially expressed FIN13. As expected, the activity of his-FIN13 was not inhibited by the addition of okadaic acid. The presence of a highly charged acidic domain in FIN13 led us to examine the effect of highly charged basic molecules on phosphatase activity. Neither poly L-lysine nor protamine sulfate significantly altered his-FIN13 activity.

The phosphatase activity of FIN13 immunoprecipitated (IP) from transfected HeLa cells was also examined. HeLa cells were transfected with a construct expressing FIN13 N-terminally tagged with a myc epitope (pRKmyc-FIN13). myc-FIN13 was immunoprecipitated from HeLa cell extracts with 9E10 (anti-myc monoclonal antibody) or 630 (anti-FIN13 polyclonal antiserum), the IP washed extensively and then either used for Western analysis or examined in a phosphatase assay for its ability to dephosphorylate $^{32}$P-labelled casein in vitro. IPs using either 9E10 or 630 followed by Western analysis using the 630 antiserum resulted in the detection of a single band of about 60 kDa in pRKmyc-FIN13 transfected cells (FIG. 6A). FIN13 expressed in bacteria or in NIH3T3 cells also has an apparent Mr of 60 kDa (data not shown and FIG. 8). Although the predicted Mr of FIN13 is 42 kDa, the anomalous migration of FIN13 on a polyacrylamide gel could be due to the highly charged acidic box. Nonetheless, both 9E10 and 630 detect the same 60 kDa band in cells transfected with a FIN13 expression construct confirming the specificity of the antibodies. IPs were then examined for phosphatase activity. All assays were performed in the presence of 1 mM okadaic acid. myc-FIN13 immunoprecipitated from HeLa cells with either 9E10 or 630 exhibited phosphatase activity in vitro (FIG. 6B). No significant phosphatase activity was observed in 9E10 IPs from control pRK5 transfected cells. In addition, EDTA (10 mM) abolished the observed FIN13 activity in 9E10 IPs. On the other hand, a reduced but significant phosphatase activity was detected in 630 IPs from pRK5 transfected cells. This activity could be due to the IP of endogenous FIN13 by the 630 antiserum, although this antiserum (raised against murine FIN13) does not appear to recognize any endogenous FIN13 protein in the western blots (FIG. 6A, see below). Protein phosphatase 2A, which is a serine threonine phosphatase belonging to the type 2A family and is okadaic acid sensitive (Mann et al., *Biochim. Biophys. Acta* 1130:100–104 (1992)) was used as control. As expected, the activity of PP2A, was abolished in the presence of okadaic acid (FIG. 6C).

Indirect immunnunofluorescence of pRKmyc-FIN13 transfected HeLa cells was performed to determine the subcellular localization of FIN13. In line with its C-terminal putative nuclear translocation signal, FIN13 was found localized using the 630 antibodies almost exclusively in the nucleus as shown by co-localized fluorescence of the DNA binding Hoechst 33342 stain. Identical localization was observed using the 9E10 antibody and omission of the primary antibody resulted in no significant fluorescence (data not shown). FIN13 was also found localized in the nucleus of HeLa, NIH 3T3 and COS-7 cells transiently transfected with pRKFIN13 (data not shown). The morphology of the nuclei of FIN13 expressing cells was somewhat abnormal, with nuclear enlargement. Hoechst staining was more diffuse compared to non-transfected cells. Expression of FIN13 for more than 48 h was frequently associated with a number of more severe morphological abnormalities such as nuclear vesiculation, nuclear membrane breakdown and nuclear condensation.

The effect of FIN13 expression on cell growth. As FIN13 was isolated as a growth factor-inducible gene and is expressed in vivo in tissues undergoing proliferation, we decided to investigate the effects of FIN13 expression on cell growth. In order to generate stable cell lines expressing FIN13, NIH 3T3 cells were co-transfected with a neomycin resistance plasmid (pRSVneo) and a construct expressing FIN13 under the control of a constitutive CMV promoter (pRKFIN13). After 2 weeks of drug selection it was evident that the number of colonies in the pRKFIN13 transfections was reduced relative to the number of colonies in the control pRK5 transfections. A similar reduction in the number of drug-resisitant colonies following transfection with pRK-FIN13 was also observed for RAT-1 and HeLa cells (data not shown). Furthermore, while FIN13 expression was clearly detectable by Western analysis 24 h post-transfection, no FIN13 was detected in pRKFIN13 transfected pools after two weeks of drug selection. Repeated attempts to isolate clones expressing FIN13 were not successful indicating that constitutive expression of FIN13 was causing either growth arrest or cell death.

Cells Transiently Transfected with FIN13 are Blocked in the Cell Cycle. We have utilized a transient transfection approach to examine the effect of FIN13 expression on DNA synthesis and cell cycle progression. Asynchronously growing HeLa cells were plated on coverslips and transfected with constructs expressing either control proteins ERK2 (pRKERK2-HA) or β-galactosidase (CMVb) or the FIN13 expressing construct, pRKFIN13. ERK2 is expressed as a nuclear protein in HeLa cells in the presence of 10% serum (Chen et al., *Mol. Cell. Biol.* 12:915–927 (1992)) while β-galactosidase is predominantly cytoplasmic. Twenty four hours after transfection, the medium was changed and cells were labelled for 12 hours with BrdU. The cells were then fixed and examined for, (1) ERK2-HA expression using the anti-HA 12Ca5 antibody, (2) for β-galactosidase expression using the GAL40 antibody or, (3) FIN13 expression using the 630 anti-FIN13 antiserum. BrdU incorporation was detected using FITC-conjugated anti-BrdU antibodies.

While non-transfected cells, ERK2-HA and β-galactosidase expressing cells were able to incorporate BrdU, strong inhibition of BrdU incorporation was observed for FIN13 over-expressing cells. While greater than 70% of cells expressing either ERK2-HA or β-galactosidase were observed to incorporate BrdU, only 10–17% of FIN13 expressing cells were observed to incorporate BrdU (Table 1). These data suggested that cells over-expressing FIN13 become blocked in the cell cycle and fail to synthesize DNA. The inhibition was presumably not due to a non-specific cytotoxic effect resulting from protein over-expression as the expression of another nuclear protein (ERK2-HA) or β-gal CMV did not significantly inhibit BrdU incorporation.

TABLE 1

Effect of FIN13 expression on Brd incorporation.[a]

| construct | total positive cells[b] | BrdU positive cells[c] | % BrdU incorporation[d] |
|---|---|---|---|
| pRKERK2-HA | 366 | 260 | 71 |
| βGALCMV | 395 | 347 | 87 |
| pRKFIN13 | 394 | 36 | 10 |
| pRKERK2-HA | 379 | 291 | 77 |
| βgalCMV | 350 | 276 | 79 |
| pRKFIN13 | 365 | 62 | 17 |

Figure 7E:
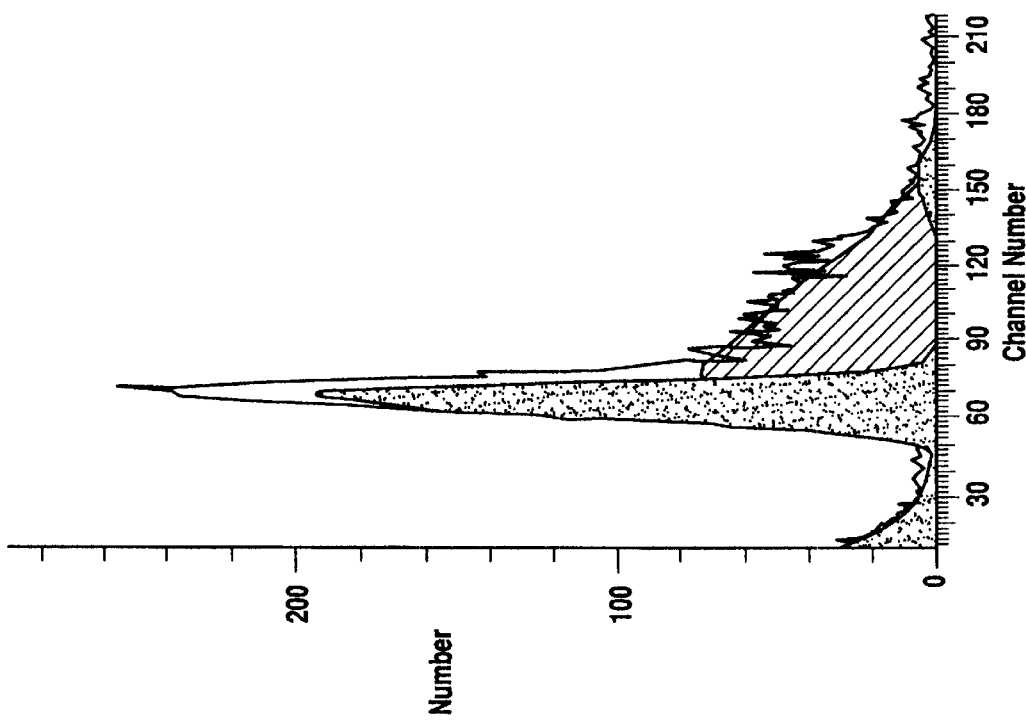
FIG. 7. Flow cytometric analysis of FIN13 expressing cells. HeLa cells were co-transfected with pcDNA3hGFP and either (A) pRKERK2-HA, (B) βCMV, or (C) pRK-FIN13. Sixty hours following transfection, cells were harvested and sorted for GFP-positive cells by FACS. Recovered cells were fixed, stained with propidium iodide and analyzed for DNA content by flow cytometry. Flow cytometry of tetracycline-regulated clone sp8.2 following culture in the presence (D) or absence (E) of 1 mg/ml of tetracyclin for 24 h is also shown.

[a]Data are form two independent experiments of transfection in HeLa cells.
[b]Cells scored positive for expression of either ERK2-HA, β-galactosidase or FIN13.
[c]Cells expressing ERK2-HA, β-galactosidase or FIN13 that had incorporated BrdU.
[d]Cells in c as a percentage of the total cells in b Although these studies indicated that DNA synthesis was blocked in FIN13 expressing cells, it was not clear at which point(s) in the cycle cells were arrested. To further investigate the nature of the cell cycle block, we examined the effect of FIN13 expression on cell cycle distribution by fluorescence activated cell sorting (FACS). HeLa cells were transiently co-transfected with a reporter construct expressing green florescent protein (pcDNA3-hGFP) together with constructs expressing either ERK2 (pRKERK2-HA), β-galactosidase (CMVb) or FIN13 (pRKFIN13). Cells were then harvested either 36 h or 60 h following the transfection and GFP-positive cells were recovered by FACS, fixed and stained with propidium iodide. Cells were then examined for DNA content by flow cytometry. Cells harvested 60 h following transfection with ERK2HA or β-galactosidase expression constructs exhibited similar cell cycle distribution (FIG. 7A and B, Table 2). However, pRKFIN13 transfected cells exhibited accumulation of cells in G1 and early S, accompanied by depletion of cells in G2/M (FIG. 7C, Table 2). HeLa cells harvested 36 h after transfection exhibited qualitatively the same cell cycle distribution. These results indicate that FIN13 overexpression causes cell cycle arrest in G1 and early S phases.

TABLE 2

Effect of FIN13 expression on cell cycle distribution.[a]

| construct | G0/G1 | S[b] | | G2/M |
|---|---|---|---|---|
| | 1N | 1–1.5N | 1.5–2N | 2N |
| pRKERK2-HA[c] | 65 | 12 | 10 | 13 |
| βgalCMV[c] | 58 | 12 | 12 | 18 |
| pRKFIN13[c] | 48 | 31 | 17 | 4 |
| sp8.2(+tet)[d] | 50 | 22 | 20 | 8 |
| sp8.2(+tet)[d] | 41 | 36 | 19 | 3 |

Figure 7D:
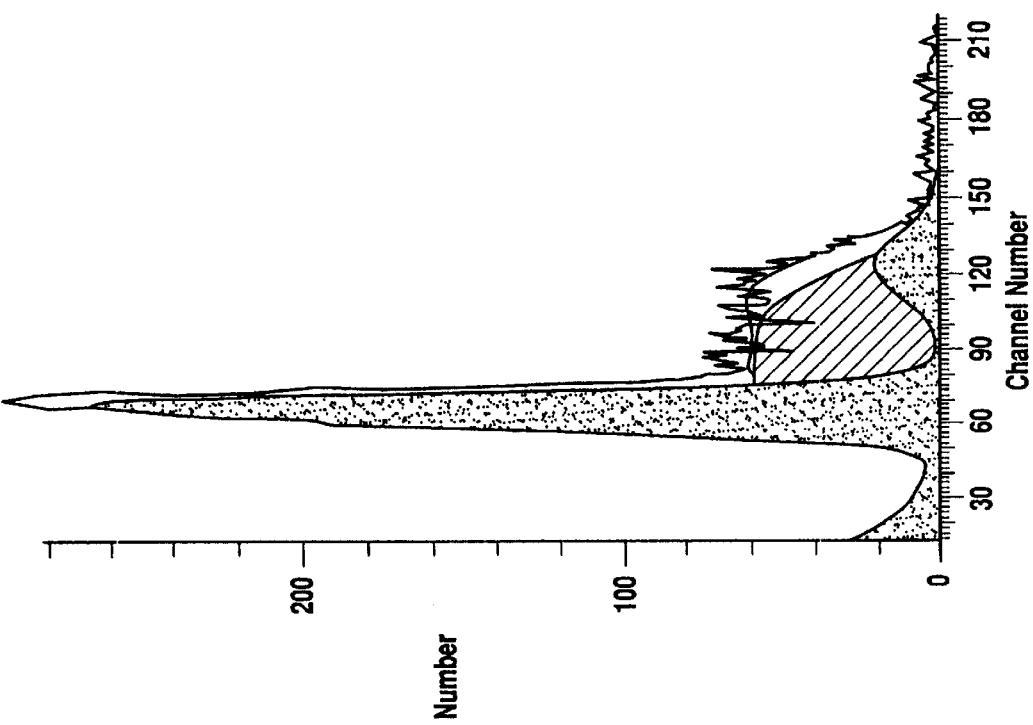

[a]All values are percentages as determined by ModFit software.
[b]S-phase was divided into early-S(1–1.5N DNA) and late-S(1.5–2N DNA).
[c]HeLa cells transfected with the indicated plasmids, from the profiles shown in FIG. 7A, B, and C.
[d]Tetracycline-regulated NIH3T3 clone from the profiles shown in FIG. 7D and E.

Inducible Expression of FIN13 also inhibits Cell Cycle Progression. To examine in more detail the cell cycle block induced by FIN13 expression we utilized the tetracycline-regulated expression system for the isolation of NIH3T3 cell lines that expressed FIN13 under the control of an inducible promoter. This inducible system employs a transactivator (tTA) that binds the tet operon upstream of a minimal promoter only in the absence of tetracycline to activate the expression of downstream sequences (Gossen and Bujard 1992, supra). In the presence of the antibiotic, ligand induced conformational change to tTA prevents binding to the tet operon and the tTA-dependent expression unit is turned off. Thus stable cell lines doubly transfected, firstly with a construct that onstitutively expresses tTA and secondly with a construct containing the tet operon/minimal promoter upstream of the FIN13 cDNA, will induce expression of FIN13 following removal of tetracycline.

Figure 8A:
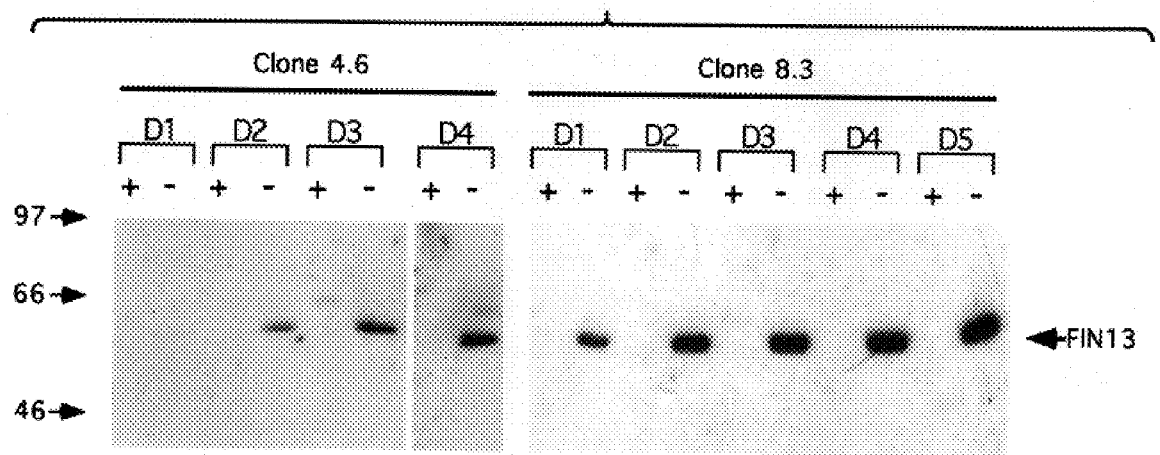
FIG. 8. Effect of induction of FIN13 expression on the growth rates of NIH 3T3 cells. Clones 4.6 and 8.3 were plated on day 0 at 10000 cells/ml in the presence (+) or absence (–) of 1 mg/ml tetracyclin and harvested for Western blot analysis and cell counting. (A) Cells were harvested daily (D1–D5) and extracts examined by Western blot using the 630 antiserum for FIN13 expression as described in the Materials and Methods. Protein concentrations were determined by Bradford assay and equal loading and transfer were confirmed by ponceau staining. Molecular weight in kDa is indicated on the left. (B) Growth rates of clones exhibiting FIN13 inducible expression. Triplicate cell counts were obtained daily (Coulter counter) until cells became confluent (4 days for clone 4.6 and 5 days for clone 8.3). Mean number of cells is plotted on a log scale versus time.

Eight inducible clones derived from 3 independent tTA-expressing NIH3T3 cell lines were studied. None of the inducible clones isolated showed detectable levels of leaky FIN13 expression in the off-state (FIG. 8 and data not shown). Shown in FIG. 8A is the Western blot analysis for two clones exhibiting inducible FIN13 expression. While clone 8.3 demonstrated strong and sustained expression, clone 4.6 exhibited weaker induction with slower onset kinetics. Both clones exhibited reduced growth rates following FIN13 induction (–tet) and the growth inhibition correlated with the level of FIN13 expression (compare FIGS. 8A and 8B). Although there was no observable effect on cellular morphology of clone 8.3 after 2 days, widespread cell death was evident by day 5 (data not shown), while clone 4.6 did not show significant levels of cell death.

Despite repeated efforts, we were not able to maintain FIN13-inducible cell lines in culture for more than 2–4 weeks. Of the 8 clones isolated, all lost inducible expression. Examination of this phenomenon by immunocytochemistry with anti-FIN13 antibodies revealed that the percentage of cells exhibiting inducibility became reduced over time. In all tetracycline-regulated clones examined, detectable FIN13 induction was completely lost after 4 weeks in culture (data not shown). Although Western blot analysis indicated that the tetracycline system offered good inducibility of FIN13 with no detectable expression in the off-state (+tet) (FIG. 8A), a number of observations suggested that a low level of leaky expression in the presence of tetracycline resulted in the instability of inducible cell lines. Firstly, all inducible clones exhibited slower growth rates even in the off-state (+tet) than the parental cells, and clones exhibiting inducible expression grew slower than non-inducible clones (data not shown). Secondly, it was consistently observed that following loss of inducible expression (and presumably also loss of leaky expression in the off-state), the growth rates of isolated clones increased, returning to rates comparable to that of the parental cells. Together, these observations argue that even low levels of constitutive FIN13 expression may exert a strong negative effect on cell growth. Attempts to prevent loss of inducible FIN13 expression by increasing the amount of tetracycline in culture media or increasing the frequency of tetracycline addition were not successful.

Although inducible expression was lost in clones 4.6 and 8.3 prior to cell cycle analysis, we were able to examine the cell cycle distribution of a clone which was induced to express FIN13 by withdrawing tetracycline shortly after removing cells from the frozen stocks. The data obtained with the sp 8.2 NIH 3T3 tetracylin-regulated clone, that had maintained FIN13 inducibility (determined by immunofluorescence) for a sufficient period of time to allow analysis of DNA content by flow cytometry are shown in FIGS. 7D and E. The data show that while the non-induced population had a cell cycle distribution of approximately 50% of cells in G1, 40% in S and 10% in G2 phases, the induced cell population showed virtually no cells in G2, with an increase in cells with an S phase DNA content (Table 2). Most importantly, cells were not distributed evenly throughout the S-phase but accumulated preferentially in early S. The similarity in cell cycle distribution due to induction of FIN13 expression to that observed in transiently transfected HeLa cells (FIGS. 7A, B, and C) is striking.

Discussion

In this study we have identified a new gene, termed FIN13, which encodes a type 2C phosphatase that is able to negatively regulate cell proliferation causing cell cycle arrest in G1/S. While its expression in normal adult tissues appears to be largely restricted to the testis, the present study indicates that FIN13 expression is induced in a range of tissues undergoing proliferation including the embryo, uterus at pregnancy, placenta, and ovaries of sexually immature mice following stimulation of folliculogenesis with diethylstilbesterol.

The induction of FIN13 mRNA in cultured cells in response to growth factors as well as its induction in a number of tissues undergoing proliferation would imply that FIN13 may serve a function related to cell growth. To investigate this possibility, we attempted to make stable cell lines that over-expressed FIN13. However, it was observed that transfection of either NIH 3T3, Rat-1 or HeLa cells with a FIN13 expression construct resulted in a decreased number of colonies compared to control transfections. In addition, ectopic FIN13 expression was undetectable in all clones isolated, further indicating that selection against FIN13 expression was a prerequisite for the proliferation and expansion of drug-resistant clones. Together, these results indicate that FIN13 was causing either cell cycle arrest or cell death. Using the tetracycline-inducible system (Gossen and Bujard, 1992, supra) for regulated FIN13 expression in NIH 3T3 cells, it was found that the induction FIN13 expression resulted in reduced cell growth. The reduced growth rate of clone 4.6 and 8.3 in the absence of significant cell death, even after 48 h of FIN13 induction, would argue that the primary effect of FIN13 was not to induce programmed cell death. Furthermore, while cell death was observed in clones expressing higher levels of FIN13 (clone 8.3), the delay in onset (>48 h) would indicate that it was most likely a secondary consequence of a non-viable arrest/delay in cell cycle progression.

Further attempts to analyze the effect of FIN13 expression on cell cycle progression using the tetracycline-inducible system were hampered due to the high rate at which tetracycline-regulated expression was lost. Clones that initially exhibited regulated FIN13 expression rapidly lost inducibility after 2–4 weeks in culture, presumably due to selective pressure against a low level of leaky expression in the off-state (+tet). The rapid loss of inducible expression has also been observed for other gene products that are toxic or negatively regulate cell growth, including p16 and p53. Therefore we employed an alternative transient transfection approach to examine the effect of FIN13 expression on the cell cycle. In these experiments, FIN13 expression was found to inhibit DNA synthesis in HeLa cells. Furthermore, co-transfection of HeLa cells with expression constructs for GFP and FIN13, followed by recovery of GFP-positive cells by FACS and analysis of the sorted cells for DNA content by flow cytometry, revealed that FIN13 expression caused G1/S arrest when compared to cells co-transfected with expression constructs for GFP and either ERK2-HA or β-galactosidase. A strikingly similar pattern of cell cycle arrest was observed in the SP8.2 tetracycline-regulated NIH3T3 clone. It was observed both in HeLa and NIH3T3 cells that while some cells clearly became arrested in G1 and failed to enter S, entry was not completely blocked, with cells also arresting in early S phase. These results are consistent with a direct but partial block in the initiation of DNA synthesis. Such a block would cause the majority of cells to accumulate at the G1/S boundary, and in early S-phase, and concomitantly result in a very small proportion of cells in the late S-phase, as these cells would have a higher probability of completing S (Table 2). On the other hand, the observed cell cycle distribution of FIN13 overexpressing cells could also be due to a partial block to S-phase progression, resulting from the reduced availability of substrate or enzymes necessary for DNA synthesis. FIN13 may also interfere with particular processes which are active both in late G1 and early S and thus cell cycle arrest occurs in a stochastic manner within this window. Regardless, over-expression of FIN13 can block cell cycle progression in both G1 and S while passage through G2/M appears to be unaffected.

A number of proteins have been identified as negative regulators of cell growth. The tumor suppressor genes constitute one such class of proteins and have been found to cause either cell cycle arrest following over-expression or to contribute, through loss of function mutations, to uncontrolled cell growth (Massague, and Weinberg, *Current Opinion in Genetics and Development* 2:228–232.(1992)). For example, over-expression of the p53 gene in a number of transformed cell lines causes apoptosis or cell cycle arrest in G1 (Chen et al., *Genes Dev.* 10:2438–2451 (1996); Diller et al., *Mol. Cell. Biol.* 10:5772–5781 (1990)). Loss of function mutations in both copies of the p53 gene have been found to lead to uncontrolled cell growth and neoplasia (Massague and Weinberg, 1992, supra). Genes encoding extracellular factors involved in growth inhibition signals such as transforming growth factor β (TGFβ) and leukaemic inhibitory factor have also been described (Massague and Weinberg, 1992, supra). TGFb causes cell cycle arrest in a number of cell types and this system has proved invaluable for studying the mechanism by which growth inhibitory signals are transduced (Reynisdottir et al., *Genes and Dev.* 9:1831–1845 (1995)). Another group of proteins involved in the negative regulation of cell growth are the inhibitors of cyclin-dependent kinases (Cdk) (Sherr, *Cell*, 79551–555 (1994)). Progression through the cell cycle is tightly controlled by the kinase activity of a series of Cdks. The Cdks are subject to positive regulation by activating phosphorylation/dephosphorylation events as well as through association with cyclins. Negative regulation of Cdks is achieved through inhibitory phosphorylation/dephosphorylation events and also the association with a number of Cdk inhibitors. Altering the balance of Cdk activity by over-expression of the Cdk inhibitor, $p_{21}^{wafl/cipl}$, has been found to cause cell cycle arrest (Givol et al., *Oncogene*, 11:2609–2618 (1995)). Another point in the mitogen signaling pathway that can be negatively regulated is at the level of mitogen activated protein (MAP) kinase. Over-expression of MAP kinase phosphatase-1 (MKP-1), which is proposed to inactivate MAP kinase by dephosphorylation, blocks entry into S phase in fibroblasts (Bondello et al., *Oncogene*, 10:1895–1904 (1995); Sun et al., *Cell*, 75:487–493 (1993)).

It would appear somewhat counter-intuitive that a mitogenic growth factor would induce the expression of a gene that in turn negatively regulates cell growth. Indeed, such a proposal is probably quite simplistic in regard to the true physiological function of FIN13. It should be noted that the ability of FIN13 to inhibit cell growth was observed under conditions of unregulated expression and/or over-expression and thus it is possible that this activity does not entirely reflect the physiological activity of the protein. Nevertheless, there are a number of important precedents in which growth factor inducible genes have been established as negative regulators of cell growth. For example, while $p_{21}^{wafl/cipl}$ appears to negatively regulate growth factor signaling by inhibiting Cdk activity, Mitchieli et al. (*Cancer Res.* 54:3391–3395 (1994)) have reported that $p21^{wafl/cipl}$ is growth factor inducible in fibroblasts. Elevated levels of $p_{21}^{wafl/cipl}$ would represent a threshold that growth factor signaling through cyclin-Cdk complexes must overcome, and may represent a mechanism by which premature entry into S phase is prevented (Mitchieli et al., 1994, supra). MKP-1, also an immediate-early growth factor inducible gene product, can block S phase entry when over-expressed (Bondello et al., 1995, suipra; Sun et al., 1993, supra). Over-expression of the growth factor-inducible dual-specificity phosphatase gene, erp, has also been found to negatively regulate cell growth, however, the physiological significance of this remains unknown (Noguchi et al., *Mol. Cell. Biol.* 13:5195–5205 (1993)).

An important question arising from the present studies concerns the possible physiological targets of FIN13 and the mechanism by which it causes cell cycle arrest. One possible explanation is that over-expression of FIN13 is toxic due to widespread non-specific dephosphorylation of nuclear proteins. While this possibility cannot be ruled out, one might expect that cells would arrest at multiple points in the cell cycle and that cell death would be more evident. This was clearly not the case with FIN13. Furthermore, the observed instability of the tetracycline inducible clones, even under conditions in which expression of exogenous FIN13 was biochemically undetectable, argues in favor of the hypothesis that low levels of unregulated expression of FIN13 are sufficient to inhibit cell growth. It is therefore possible that constitutive expression of FIN13 at an inappropriate time in the cell cycle causes arrest. Finally, the cell cycle arrest observed following over-expression of FIN13 could be due to constitutive dephosphorylation of physiological targets important in driving cells through G1/S. We propose that FIN13 is induced in response to growth factors and is important in regulating G1/S events. While perhaps normally acting as a cell cycle brake to ensure against constitutive positive signals and uncontrolled cell proliferation, over-expression of FIN13 alters the balance between positive and negative signals causing G1/S arrest.

An additional consideration in regard to the inhibition of cell growth by FIN13 is that the mechanism by which the activity of FIN13, or indeed other type 2C phosphatases, are regulated in vivo is unknown (Brautigan, *Cancer Biol.* 6:211–217 (1995); Cohen and Cohen, 1989, supra; Hunter, 1995, supra). Because of the strong negative effect on cell growth, we predict that the biological activity of FIN13 would be normally tightly regulated in vivo. Overexpression or unregulated expression are likely to uncouple FIN13 from its normal regulatory control resulting in a constitutive negative signal that causes G1/S arrest. Furthermore, FIN13 is itself a phosphorylated protein (data not shown) and phosphorylation could contribute to the regulation of FIN13 activity. The isolation of FIN13 mutants that are either catalytically inactive, or in which the catalytic activity is anomalously regulated is important for understanding the mechanism by which FIN13 causes cell cycle arrest.

It is becoming increasingly apparent that cell proliferation should be viewed as being controlled by a series of mutually entwined positive and negative signals that enable faithful replication of cellular DNA and mitosis (Cohen and Cohen, 1989, supra; Hunter, 1995, supra; Murray, *Current Opinion in Cell Biology* 6:872–876 (1994); Schlessinger and Ulrich, *Neuron* 9:383–391 (1993); Sherr, 1994, supra). An imbalance between the relative contribution of positive and negative signals due to over-expression of a particular protein may alter growth characteristics, as observed for FIN13.

EXAMPLE 4

ISOLATION OF A HUMAN FIN13 cDNA

Isolation of the human cDNA for FIN13 is achieved by low stringency hybridization-screening of a human cDNA library. Conditions would involve hybridization of a labelled cDNA at 50° C. in 50% formamide, 5× SSC (1× SSC= 0.15M NaCl, 0.015M sodium citrate pH 7.0), 5× Denhardt's solution (50×=1% Ficoll-400, 1% polyvinylpyrilidone-360, 1% BSA), 50 mM sodium phosphate (pH 7.0), 0.1% SDS and 350 µg/ml sonicated salmon sperm DNA, followed by washing the filters in 1× SSC, 0.1% SDS at 50° C.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A purified nucleic acid molecule encoding a fibroblast growth factor (FGF)-inducible FIN13 serine/threonine phosphatase which hybridizes to the DNA sequence of FIG. 1 (SEQ ID NO:1) under stringent conditions, wherein said stringent conditions comprise 40% formamide, 6× SSC and a $T_m$ of about 60° C., or a fragment of said purified nucleic acid molecule having at least 30 contiguous nucleotides.

2. A purified nucleic acid molecule comprising the DNA sequence of FIG. 1 (SEQ ID NO:1), or fragments thereof comprising at least 30 contiguous nucleotides in the coding region.

3. A purified nucleic acid molecule which encodes a fibroblast growth factor (FGF)-inducible FIN13 serine/threonine phosphatase comprising an amino acid sequence of FIG. 1 (SEQ ID NO:2), fragments thereof comprising at least 10 contiguous amino acid residues, or a conjugate thereof.

4. A purified nucleic acid molecule encoding a fibroblast growth factor (FGF)-inducible FIN13 serine/threonine phosphatase, wherein said FIN13 comprises a first domain, said first domain comprising amino acid residue numbers 1 through 100 of the amino acid sequence of FIG. 1 (SEQ ID NO:2), an acidic box domain comprising amino acid residue numbers 108 through 169 of FIG. 1 (SEQ ID NO:2), and a serine/threonine phosphatase domain comprising amino acid residues 174 through 352 of the amino acid sequence of FIG. 1 (SEQ ID NO:2), or a fragment of said purified nucleic acid molecule having at least 30 contiguous nucleotides.

5. The purified nucleic acid molecule of claim 4 having a nucleotide sequence as depicted in FIG. 1 (SEQ ID NO:1) from nucleotide 214 to nucleotide 389.

6. The purified nucleic acid molecule of claim 4 which encodes a fragment of FIN13 comprising amino acid residue numbers 174 to 352 of the amino acid sequence of FIG. 1 (SEQ ID NO:2).

7. The purified nucleic acid molecule of claim 4 which encodes a fragment of FIN13 comprising amino acid residue numbers 1 to 100 of FIG. 1 (SEQ ID NO:2).

8. The purified nucleic acid molecule of claim 4 which encodes a fragment of FIN13 comprising amino acid residue numbers 108 to 169 of FIG. 1 (SEQ ID NO:2).

9. The purified nucleic acid molecule of claim 4 which is DNA.

10. A recombinant DNA expression vector comprising the purified nucleic acid molecule of claim 9, wherein the purified nucleic acid molecule is operatively associated with an expression control sequence.

11. A transformed host cell comprising the DNA vector of claim 10.

12. A recombinant virus comprising the DNA vector of claim 10.

13. The recombinant virus of claim 7 selected from the group consisting of a retrovirus, herpes simplex virus (HSV), papillomavirus, Epstein Barr virus (EBV), adenovirus, and adeno-associated virus (AAV).

14. A method for producing a FIN13 comprising culturing the transformed host cell of claim 11 under conditions that provide for expression of the FIN13.

15. The method according to claim 14 wherein the host cell is a bacterium.

16. The method according to claim 14 wherein the host cell is a mammalian cell.

* * * * *